(12) United States Patent
Kriesel et al.

(10) Patent No.: US 11,046,482 B1
(45) Date of Patent: Jun. 29, 2021

(54) ADHESIVE VISCOELASTIC POLYMER AND ITS USE IN LIGHTING APPARATUS

(71) Applicant: Tak Logic LLC, Ettrick, WI (US)

(72) Inventors: Matthew Wayne Kriesel, Melrose, WI (US); Troy Bradley Goodenough, Mindoro, WI (US)

(73) Assignee: Tak Logic, LLC, Ettrick, WI (US)

( * ) Notice: Subject to any disclaimer, the term of this patent is extended or adjusted under 35 U.S.C. 154(b) by 0 days.

(21) Appl. No.: 16/141,736

(22) Filed: Sep. 25, 2018

Related U.S. Application Data

(63) Continuation-in-part of application No. 15/731,815, filed on Aug. 7, 2017, which is a continuation of application No. 14/999,722, filed on Jun. 20, 2016.

(60) Provisional application No. 62/231,004, filed on Jun. 22, 2015.

(51) Int. Cl.
| | |
|---|---|
| *B65D 25/04* | (2006.01) |
| *B05D 1/02* | (2006.01) |
| *B65D 33/06* | (2006.01) |
| *A61B 50/33* | (2016.01) |
| *A01K 97/06* | (2006.01) |
| *A61B 50/30* | (2016.01) |
| *A61B 50/00* | (2016.01) |
| *C08G 18/10* | (2006.01) |
| *C08G 18/36* | (2006.01) |
| *C08G 18/48* | (2006.01) |

(52) U.S. Cl.
CPC ............. *B65D 25/04* (2013.01); *A01K 97/06* (2013.01); *A61B 50/33* (2016.02); *B05D 1/02* (2013.01); *B65D 33/06* (2013.01); *A61B 2050/002* (2016.02); *A61B 2050/3008* (2016.02); *C08G 18/10* (2013.01); *C08G 18/36* (2013.01); *C08G 18/4825* (2013.01); *C08G 18/4829* (2013.01)

(58) Field of Classification Search
CPC .......... B65D 25/04; B65D 33/06; B05D 1/02; A61B 50/33; A61B 2050/3008; A61B 2050/002; A01K 97/06; C08G 18/10; C08G 18/4825; C08G 18/4829; C08G 18/36

See application file for complete search history.

(56) References Cited

U.S. PATENT DOCUMENTS

| | | |
|---|---|---|
| 3,507,071 A | 4/1970 | Bryson |
| 5,677,413 A | 10/1997 | Barksby et al. |
| 5,864,001 A | 1/1999 | Masse et al. |
| 6,588,511 B1 | 7/2003 | Kriesel et al. |
| 6,673,409 B1 | 1/2004 | Wheatley |
| 6,896,065 B2 | 5/2005 | Kriesel et al. |
| 7,041,719 B2 | 5/2006 | Kriesel et al. |
| 7,125,602 B2 | 10/2006 | Wheatley |
| 7,252,867 B2 | 8/2007 | Wheatley |
| 7,910,188 B2 | 3/2011 | Wheatley |
| 7,923,088 B2 | 4/2011 | Wheatley |
| 8,110,269 B2 | 2/2012 | Wheatley |
| 8,110,270 B2 | 2/2012 | Wheatley |
| 8,302,213 B2 | 11/2012 | Kriesel |
| 9,974,342 B1 | 5/2018 | Kriesel |
| D880,950 S | 4/2020 | Kriesel et al. |
| 10,681,830 B1* | 6/2020 | Goodenough ........ G06F 3/0416 |
| 10,717,582 B1 | 7/2020 | Goodenough |
| 10,807,767 B1 | 10/2020 | Kriesel et al. |
| D902,584 S | 11/2020 | Kriesel et al. |
| 2004/0191446 A1 | 9/2004 | Kriesel |
| 2004/0200623 A1 | 10/2004 | Kriesel |
| 2006/0272367 A1 | 12/2006 | Kriesel |
| 2006/0287147 A1 | 12/2006 | Kriesel |
| 2008/0005929 A1 | 1/2008 | Hardy et al. |
| 2008/0026658 A1 | 1/2008 | Kriesel |
| 2008/0250729 A1 | 10/2008 | Kriesel |
| 2009/0042676 A1 | 2/2009 | Kriesel |
| 2010/0048754 A1* | 2/2010 | Abraham ................ C08L 75/04 521/174 |
| 2010/0170139 A1 | 7/2010 | Zhou |
| 2012/0222457 A1 | 9/2012 | Kriesel et al. |
| 2015/0053583 A1 | 2/2015 | McCormick et al. |

FOREIGN PATENT DOCUMENTS

JP     2006296699 A  * 11/2006

\* cited by examiner

*Primary Examiner* — Rabon A Sergent
(74) *Attorney, Agent, or Firm* — Bryan R. Rosiejka

(57) ABSTRACT

A lighting apparatus is provided including at least one light adhered to a releasably adhesive viscoelastic polymer component. The light may be disposed upon, or at least partially disposed within, the viscoelastic polymer. The viscoelastic polymer component has a unique adhesiveness and cohesiveness, which allows the lighting apparatus to be releasably adhered to a variety of objects. Upon release of the lighting apparatus from an object, the viscoelastic polymer component leaves substantially no residue remaining on the object. The lighting apparatus can then be re-adhered to the object with substantially the same degree of adhesiveness as when originally adhered. In addition, a variety of articles can be adhered to the lighting apparatus, as desired.

47 Claims, 15 Drawing Sheets

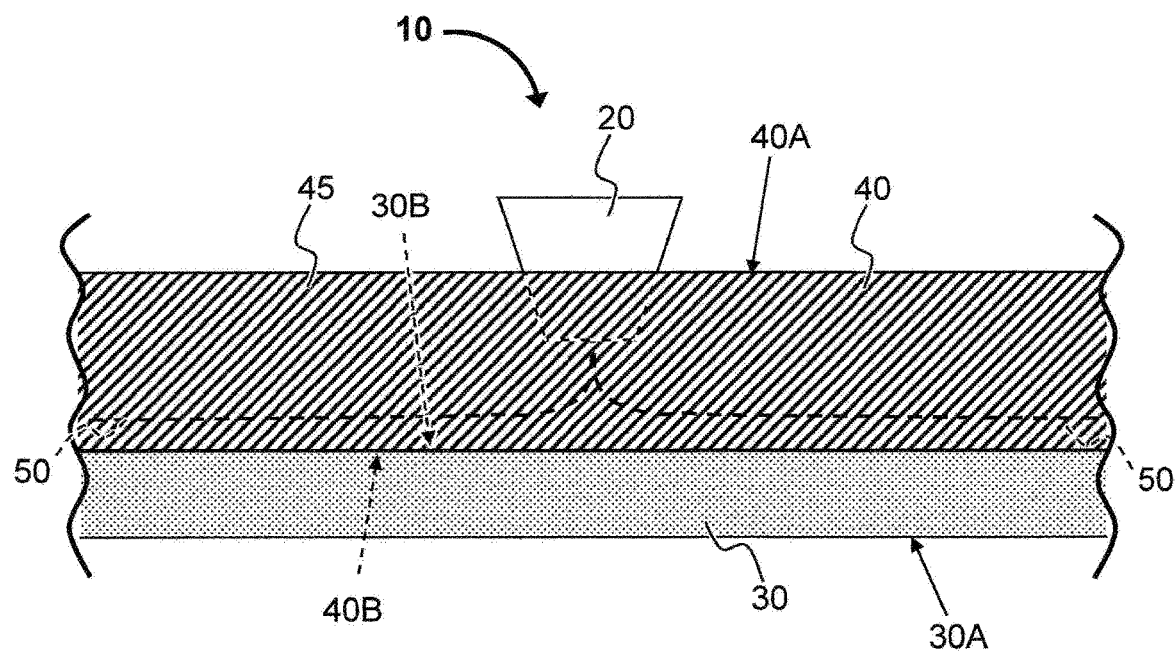
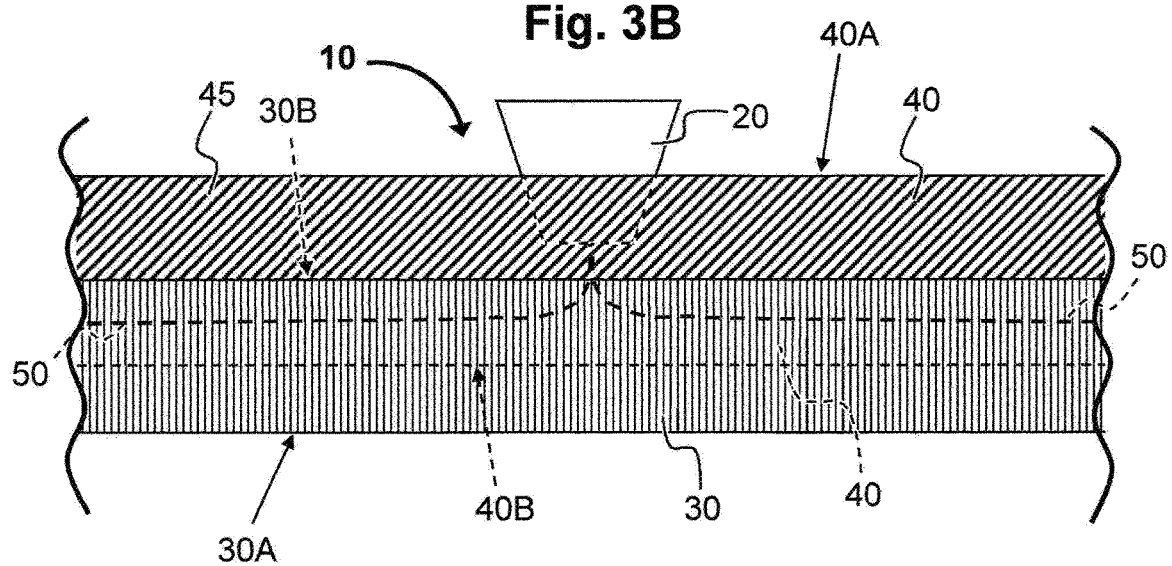

ADHESIVE VISCOELASTIC POLYMER AND ITS USE IN LIGHTING APPARATUS

CROSS-REFERENCE TO RELATED APPLICATIONS

This application claims priority to U.S. patent application Ser. No. 15/731,815 filed in the United States Patent and Trademark Office on Aug. 7, 2017, which is a Continuation-in-Part of U.S. patent application Ser. No. 14/999,722 filed in the United States Patent and Trademark Office on Jun. 20, 2016, which is a Nonprovisional application of Provisional U.S. Patent Application No. 62/231,004 filed in the United States Patent and Trademark Office on Jun. 22, 2015, all of which applications are hereby incorporated in their entirety herein in a manner that is consistent herewith.

TECHNICAL FIELD

The present disclosure relates to lighting means. More particularly, the present invention relates to lighting apparatus comprising highly cohesive and adhesive thermoset viscoelastomeric polymer components, capable of adhering the lighting apparatus to a variety of objects, and further capable adhering a variety of articles thereto.

BACKGROUND

In virtually all aspects of life, lighting is required. For example, locations such as dark or confined spaces, and items such containers (e.g., tackle boxes, toolboxes, pill boxes, cosmetic containers, etc.), drawers, cabinets, closets and the like, often contain areas which lack sufficient lighting for the human eye to adequately discern the contents therein. As a result, a user must blindly feel around such spaces in hopes that a desired item is randomly grasped. Unfortunately, such a process often fails, which can cause feelings of frustration. Alternatively, a user must utilize an external source of lighting, such as by utilizing a lighting means (e.g., a flashlight); or by installing a relatively expensive, complex, and permanent electrical light system; or by physically carrying the item to a location having greater, sufficient lighting; and the like.

Thus, there is a need for a portable lighting apparatus that can be optionally permanently or releasably installed as desired at a desired location upon a dark space item. There is also a need for a lighting apparatus that is relatively simple to install upon a dark space item, and can be releasably removed therefrom, as desired. There is also a need for a lighting apparatus that is relatively less expensive and/or less complex than a conventional permanent electrical light system. There is also a need for a light source that can releasably adhered at the location of the dark space item and optionally repositioned repeatedly as desired, without loss of adhesiveness. There is a further need for a lighting apparatus which leaves substantially no residue upon removal from an object.

In addition, it is often desirable to utilize various articles when located in areas having insufficient lighting, such as in dark spaces, within dark items, and/or during nighttime hours. Such articles can include, but are not limited to, tools (e.g., screwdrivers, wrenches, etc.), fishing equipment (e.g., fishing lures, bobbers, etc.), camping equipment (e.g., eating utensils, tents, etc.), hygienic articles (e.g., toothbrushes, razors, etc.), cosmetic articles (lipstick, mirrors, etc.), keyboards, reading materials, and the like. Unfortunately, in order to adequately utilize such articles, a user must either move them to a location having sufficient lighting provided by an external source (e.g., permanent electrical lighting, a gas lantern, a campfire, a flashlight, etc.), or otherwise wait until daytime hours. Thus, there is a need for a lighting source which can illuminate an article, and therefore eliminate the need for changing to a different location having a more adequate light source, or inefficiently waiting until the lighting becomes adequate.

In addition, conventional external sources of light can be relatively complex, can generate undesirable heat, and/or can be relatively energy inefficient. Thus, there is a further need for a lighting apparatus which emits low temperature and/or requires low power, as compared to such conventional external sources of light.

In addition, conventional external sources of light often require the user to physically hold onto them, requiring the use of one hand or other body part, for example, therefore rendering it unavailable for the present task (e.g., requiring the user to function with only the other hand). Thus, there is also a need for a lighting apparatus which is self-adhering to an object, leaving a person's relevant body parts available for completing the task.

In addition, conventional adhesives (such as double-sided adhesive tape) tends to leave a reside of adhesive on the surface of an object upon removal of such conventional adhesives. Thus, there is also a need for lighting apparatus comprising double-sided adhesive component that leaves substantially no residue on the surface of an object upon removal of the lighting apparatus from the object.

In addition, conventional attachment means (e.g., double-sided adhesive tapes, glues, mechanical fasteners) are typically considered to be relative permanent fasteners, and thus cannot be readily re-used, at least not without a substantial loss in adhesiveness of the fastener. Therefore, there is also a need for a lighting apparatus comprising an attachment component that is releasable, and which can be refastened without a substantial loss of adhesiveness.

In addition, conventional lighting means tend to be relatively permanent when mounted upon an object at a particular location. Thus, when the lighting needs change within a darkened space, adjustment of the lighting location is typically not practicable. Therefore, there is also a need for a lighting apparatus that can be releasably adhered to an object in a darkened space, and that can be relatively easily removed and re-positioned within the darkened space to meet changing lighting needs.

SUMMARY

In response to the problems and/or needs discussed above, the invention of the present disclosure solves at least one or more of such problems and/or needs.

In some aspects, a low power and/or low temperature light (e.g., a light-emitting diode ("LED"), ultra-violet ("UV") light, etc.), or plurality thereof, can be combined with an adhesive viscoelastomer product which provides a viscoelastic polymer component of the present invention, to form an inventive portable, self-adhesive lighting apparatus, which can be permanently or releasably adhered to an object and/or to which an article can be releasably adhered thereto.

In some aspects, the inventive lighting apparatus can be relatively simple to install upon a dark space item, and can be releasably removed therefrom, as desired. In other aspects, the inventive lighting apparatus can relatively less expensive and/or less complex than a conventional permanent electrical light system. In still other aspects, the inventive lighting apparatus can be releasably adhered at the location of a dark space item and optionally repositioned repeatedly as desired, without substantial loss of adhesiveness. In yet other aspects, the inventive lighting apparatus can leave substantially no residue upon removal from an object.

In some aspects, the inventive lighting apparatus can illuminate an article, and therefore eliminate the need for changing to a different location having a more adequate light source, or inefficiently waiting until the lighting becomes adequate. In other aspects, the inventive lighting apparatus can emit low temperature and/or requires low power, as compared to conventional external sources of light. In still other aspects, the inventive lighting apparatus can be self-adhering to an object, leaving a person's relevant body parts available for completing a task.

In some aspects, the inventive lighting apparatus comprises a double-sided adhesive component that leaves substantially no residue on the surface of an object upon removal of the lighting apparatus from the object. In other aspects, the inventive lighting apparatus comprises an attachment component that is releasable, and which can be refastened to an object without a substantial loss of adhesiveness. In still other aspects, the inventive lighting apparatus can be releasably adhered to an object in a darkened space, and can be relatively easily removed and re-positioned within the darkened space to meet changing lighting needs.

In some aspects, the inventive lighting apparatus can include a switch. In some further aspects of such embodiments, the switch can be a manual switch. In other aspects, the switch can be an automatic switch.

In some aspects, the light(s) can be at least partially encapsulated into the adhesive viscoelastic polymer component, adhered onto a surface of the viscoelastic polymer component, and/or combinations thereof.

In some aspects, the inventive adhesive viscoelastomer can be formed into a thermoset substrate, such as a coating, sheet, film, inlay, strip, pad, and the like, and/or combinations thereof, having unique cohesive and adhesive properties. In further aspects of such embodiments, the inventive cohesive and adhesive substrate herein can compositionally possess an adhesive attraction of at least about 300 grams of force per square centimeter ($g_f/cm^2$) of contact area as ascertained by the Adhesiveness & Cohesiveness Test (e.g., having a constant test speed pulling force needed to separate the substrate from a 1.76 cm$^2$ circular nickel plated test probe at 20° C.). In some aspects, the inventive viscoelastic polymer comprises less than 50-percent by weight (50 wt %) epoxidized vegetable oil.

In preferred embodiments, a lighting apparatus comprises at least one light and a viscoelastic polymer adhered to the at least one light.

In some further aspects, the viscoelastic polymer is prepared by thermosetting a reaction media comprising a substantially uniform admixture of:
 a) an isocyanate polymer precursor,
 b) about 35-percent to about 55-percent by weight of the admixture of polyols, and
 c) an effective amount of plasticizer containing less than about 50-percent by weight of the admixture of an epoxidized triglyceride plasticizer,
where the polyols comprise straight chain linking diols and cross-linking triols, each having repetitive oxygen-containing functional groups at a weight ratio of diols to triols ranging from about 7:13 to about 13:7. In further aspects, the effective amount of plasticizer is sufficient to provide an adhesiveness of the resultant viscoelastic polymer of at least about 300 $g_f/cm^2$ as measured by the Adhesiveness & Cohesiveness Test.

In some aspects, the lighting apparatus comprises a viscoelastic polymer that is adhered to at least one light either via adhesive bonding of the viscoelastic polymer to the at least one light, or via chemical bonding by thermosetting a reaction media in situ to form the viscoelastic polymer onto the at least one light. In other aspects, the lighting apparatus comprises a viscoelastic polymer which compositionally possesses sufficient adhesiveness and cohesiveness to adhere the lighting apparatus to an object at a stabilized position and to release the lighting apparatus by an applied force sufficient to overcome an adhesive attraction of the viscoelastic polymer to the object.

In some aspects, the lighting apparatus comprises at least one light that is a low power light, a low temperature light, or combination thereof. In other aspects, a lighting apparatus comprises at least one light and a viscoelastic polymer adhered to the at least one light, where the viscoelastic polymer at least partially encapsulates the at least one light.

In some aspects, the lighting apparatus comprises an electrical connector. In other aspects, the lighting apparatus comprises a switch. In still other aspects, the lighting apparatus comprises a support structure.

In some aspects, the lighting apparatus a lighting apparatus comprises at least one light, a viscoelastic polymer adhered to the at least one light, and a support structure, where the at least one light and the support structure form a lighting assembly.

In some aspects, a lighting apparatus comprises at least one light and a viscoelastic polymer adhered to the at least one light, where the viscoelastic polymer exhibits an adhesiveness of at least about 300 $g_f/cm^2$ as measured by the Adhesiveness & Cohesiveness Test. In other aspects, the viscoelastic polymer exhibits an adhesiveness of at least about 500 $g_f/cm^2$ as measured by the Adhesiveness & Cohesiveness Test. In still other aspects, the viscoelastic polymer exhibits an adhesiveness of between about 300 $g_f/cm^2$ and 2200 $g_f/cm^2$ as measured by the Adhesiveness & Cohesiveness Test. In yet other aspects, the viscoelastic polymer exhibits an adhesiveness of between about 500 $g_f/cm^2$ and 1200 $g_f/cm^2$ as measured by the Adhesiveness & Cohesiveness Test without evidencing any substantial change in the adhesiveness after at least about four (4) weeks.

In some aspects, a lighting apparatus comprises at least one light and a viscoelastic polymer adhered to the at least one light where the viscoelastic polymer exhibits antimicrobial properties.

In some aspects, a lighting apparatus comprises at least one light and a viscoelastic polymer adhered to the at least one light where the viscoelastic polymer comprises a thermoset reaction product of a thermosetting reaction media comprising:
 a) a cross-linked thermoset structure obtained by reacting:
  1) about 4-percent to about 7-percent by weight of a diisocyanate prepolymer;
  2) about 10-percent to about 35-percent by weight of a straight chain producing polyether diol; and
  3) about 25-percent to about 35-percent by weight of a polyether triol;
where the weight ratio of the polyether diol to the polyether triol ranges from about 7:13 to about 13:7; and b) from about 20-percent to about 55-percent by weight of a plasticizer uniformly and cohesively dispersed throughout the reaction product, wherein the plasticizer comprises:
  1) about 0-percent to less than about 50-percent by weight of an epoxidized triglyceride and
  2) about 0-percent to about 40-percent by weight of an ester plasticizer;
where the total amount of plasticizer in the reaction product ranges from about 20-percent to about 48-percent by weight of the reaction product with the plasticizer being cohesively bound within the reaction product to provide a viscoelastic polymer having an adhesion release strength of at least about 300 g/cm² as measured by the Adhesiveness/Cohesiveness Test.

In some aspects, a lighting apparatus comprises at least one light and a viscoelastic polymer adhered to the at least one light where the viscoelastic polymer comprises a cohesive and adhesive thermoset viscoelastomeric reaction product formed from a thermosetting reaction media comprising:
  a) about 10-percent to about 35-percent by weight of a polyether diol;
  b) about 25-percent to about 35-percent by weight of a polyether triol;
  c) about 4-percent to about 7-percent by weight of an diisocyanate prepolymer; and
  d) about 20-percent to less than about 50-percent by weight of an epoxidized triglyceride oil;
where the weight ratio of the polyether diol to polyether triol ranges from about 7:13 to about 13:7, and where the thermosetting reaction media has been cured by a catalytic amount of a curing catalyst.

In further aspects, the epoxidized triglyceride oil comprises an epoxidized soybean oil in an amount ranging from about 42-percent to about 48-percent by weight of the total reaction media weight. In other further aspects, the weight ratio of polyether diol to polyether triol ranges from about 2:3 to about 3:2. In still other further aspects, the polyether diol and polyether triol each have a molecular weight ranging from about 1000 to about 8000 consisting essentially of either an ethylene or a propylene ether linkage. In yet other further aspects, the polyether diol and the polyether triol comprise a sequenced oxyalkylene polyols grouping selected from a polyoxyethylene and a polyoxypropylene grouping, the polyether diol and the polyether triol each have a molecular weight ranging from about 3000 to about 6000, and the epoxidized triglyceride oil consists essentially of an epoxidized soybean oil. In still other further aspects, the epoxidized triglyceride oil is vegetable oil ranging from about 25 parts to about 45 parts by weight, and the thermosetting reaction media further comprises from about 10-percent to about 40-percent by weight of a polyalkylene ester polyester. In yet other further aspects, the substrate is chemically bonded to a surface area of the at least one light by thermosetting the reaction media in situ upon the surface area.

In some aspects, a lighting apparatus comprises at least one light and a viscoelastic polymer adhered to the at least one light, where the viscoelastic polymer comprises:
  a) about 3-percent to about 8-percent by weight of an isocyanate precursor polymer;
  b) about 20 parts to about 40 parts by weight of a straight chain producing polyoxyalkylene diol;
  c) about 20 parts to about 40 parts by weight of a cross-linking polyoxyalkylene triol;
  d) about 0-percent to less than about 50-percent by weight of an epoxidized triglyceride; and
  e) greater than about 5-percent by weight of an ester plasticizer.

In further aspects, cross-links caused by polymerization of the cross-linking polyoxyalkylene triols are separated by intervening straight chain bridging polymerizates provided by the straight chain producing polyoxyalkylene diol, and the weight ratio of polyoxyalkylene diol to polyoxyalkylene triol ranges from about 3:2 to about 2:3. In other further aspects, the polyoxyalkylene diol and the polyoxyalkylene triol each comprise an alkylene grouping of either an ethylene group or a propylene group. In still other further aspects, the molecular weight of the polyoxyalkylene diol and the polyoxyalkylene triol range from about 3000 to about 6000.

In some aspects, a lighting apparatus comprises at least one light and a viscoelastic polymer adhered to the at least one light where the viscoelastic polymer comprises:
  a) about 3-percent to about 10-percent by weight of an isocyanate precursor polymer;
  b) about 10-percent to about 35-percent by weight of a polyether diol having a molecular weight of at least about 1000;
  c) about 10-percent to about 40-percent by weight of a polyether triol having a molecular weight of at least about 1000; and
  d) about 20-percent to less than about 50-percent by weight of a plasticizer;
where the weight ratio of polyether diol to polyether triol ranges from about 7:13 to about 13:7, and the polyether diol provides sufficient straight chain linkage to permit a cohesive loading of an effective amount of plasticizer within the thermoset viscoelastomeric reaction product to provide an adhesion release strength of the viscoelastic polymer of at least about 300 g/cm² as measured by the Adhesiveness & Cohesiveness Test.

In some aspects, a lighting apparatus comprises at least one light and a viscoelastic polymer adhered to the at least one light where the viscoelastic polymer comprises:
  a) about 30 parts to about 50 parts by weight of an isocyanate prepolymer;
  b) about 150 parts to about 200 parts by weight of a polyether diol;
  c) about 150 parts to about 200 parts by weight of a polyether triol;
  d) about 200 parts to about 240 parts by weight of plasticizer;
  e) about 1 part to about 3 parts by weight of a bismuth-based catalyst; and
  f) 0 parts to about 20 parts by weight of a UV stabilizer;
where the diol to triol weight ratio ranges from about 7:13 to about 13:7, and the plasticizer comprises from about 150 parts to about 180 parts by plasticizer weight of epoxidized soybean oil and about 40 parts to about 70 parts by plasticizer weight of dibutal sebecate.

In further aspects, the viscoelastic polymer further comprises from about 0 parts to about 2 parts by weight of a pigment. In other further aspects, the isocyanate prepolymer is 4,4-methylenediphenyl diisocyanate-based prepolymer.

In some aspects, a lighting apparatus comprises at least one light and a viscoelastic polymer adhered to the at least one light where the viscoelastic polymer has a thickness ranging from about 1.5 mm to about 25 cm.

The invention also includes methods for making an inventive lighting apparatus having at least one light adhered to an inventive viscoelastic polymer.

In some preferred embodiments, a method for preparing a lighting apparatus having a sufficient stable adhesiveness and cohesiveness to retain to, and to release from, an object, comprises:

a) providing a light
    b) providing a power source;
    c) providing a switch electrically connected to the light and the power source;
    d) providing an uncured thermoset viscoelastomeric reaction product of a thermosetting reaction media comprising:
        1) about 10-percent to about 35-percent by weight of a polydiol;
        2) about 25-percent to about 35-percent by weight of a polytriol;
        3) about 4-percent to about 7-percent by weight of an isocyanate prepolymer; and
        4) about 42-percent to less than about 50-percent by weight of an epoxidized vegetable oil;
    e) coating at least a portion of the light with the uncured thermoset viscoelastomeric reaction product;
    f) curing the thermoset viscoelastomeric reaction product in situ to form a lighting apparatus comprising a viscoelastic polymer;

where the viscoelastic polymer is bonded to the light to form the lighting apparatus.

In some further aspects of such embodiments, the thermosetting reaction media further comprises an effective amount of a thermosetting catalyst for curing into the viscoelastic polymer. In other further aspects, the method further comprises placing the lighting apparatus in contact with an object, such that the viscoelastic polymer is adhesively engaged and releasably secured to the object. In yet other further aspects, the method further comprises placing an article in contact with the lighting apparatus.

In some aspects, a method of forming a lighting apparatus-container combination comprises:

a) providing a lighting assembly comprising a light, an electrical connector, and a switch;
    b) providing a container;
    c) positioning the lighting assembly in contact with a first location within the container;
    d) providing a thermosetting reaction media by combining a first solution comprising about 1-percent to about 10-percent by weight of an isocyanate prepolymer and about 20-percent to less than about 50-percent by weight of a plasticizer, with a second solution comprising about 10-percent to about 40-percent by weight of a polydiol and about 10-percent to about 40-percent by weight of a polytriol;
    e) mixing the first solution with the second solution to form an uncured viscoelastic polymer;
    f) coating at least a portion of the of the lighting assembly and a least a portion of the first location of the container with at least a portion of the uncured viscoelastic polymer;
    g) allowing the uncured viscoelastic polymer to cure to form a lighting apparatus adhered to the first location of the container, to form a lighting apparatus-container combination.

In some further aspects, the ester plasticizer is an ester of a sebecate plasticizer. In other further aspects, the second solution further comprises about 0.5-percent to about 5.0-percent of a UV stabilizer. In still other further aspects, the second solution further comprises less than about 1.0-percent of a pigment. In yet other further aspects, the second solution has a polydiol to polytriol weight ratio of about 3:2 to about 2:3. In yet further aspects, the polydiol and the polytriol are polyethers. In still other further aspects, the polydiol and polytriol each comprise an alkylene grouping selected from the group consisting of an ethylene group or a propylene group.

In some further aspects, the switch is substantially free of viscoelastic polymer. In other further aspects, the allowing of the uncured viscoelastic polymer to cure forms a viscoelastic polymer component of the lighting apparatus having a thickness of at least about one (1) millimeter. In still other further aspects, the container is selected from a tackle box, a toolbox, a pillbox, an ammunition box or a cosmetic container.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects and advantages of the present invention will become better understood with regard to the following description, appended claims and accompanying drawings where:

FIG. 3A is a partial side view showing a lighting apparatus of the present invention having a lighting assembly in contact with an inventive viscoelastic polymer component;

FIG. 3B is a partial side view showing a lighting apparatus of the present invention having a lighting assembly partially encapsulated within an inventive viscoelastic polymer component;

Figure 7A:
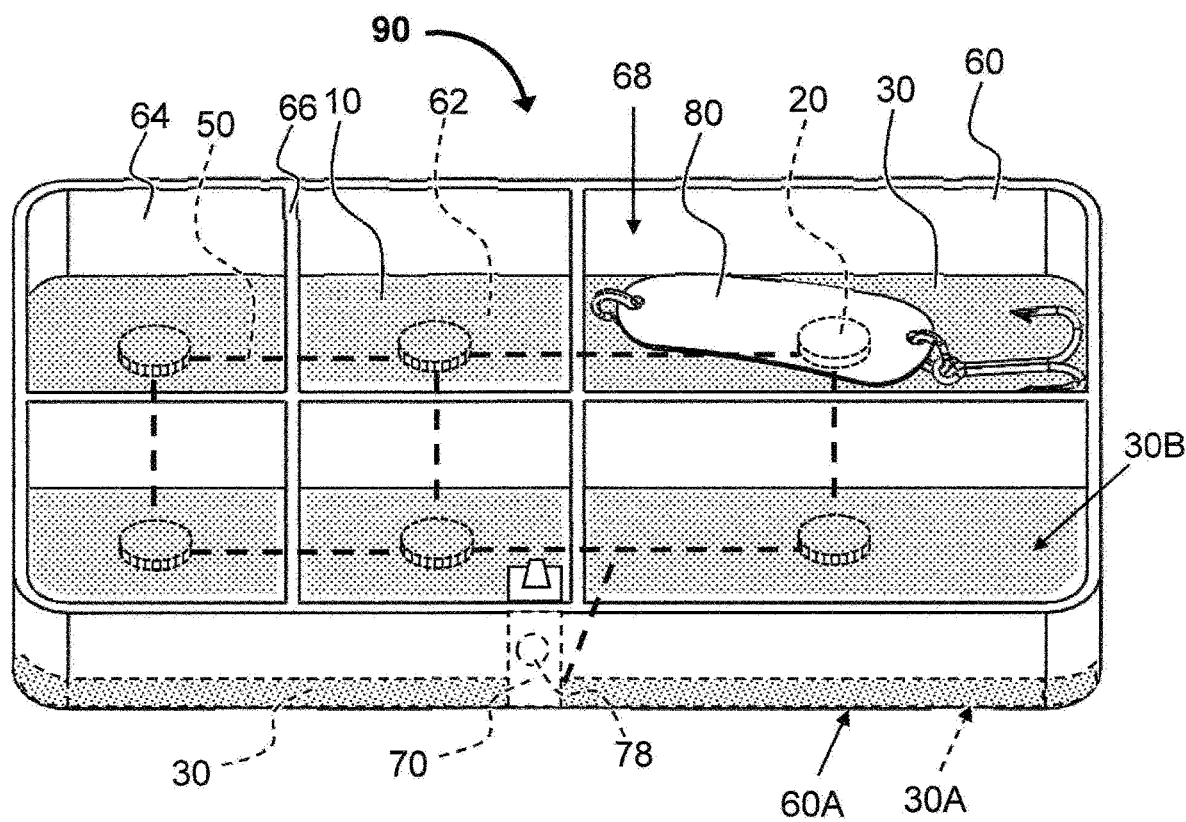
FIG. 7A is a perspective view showing a lighting apparatus of the present invention comprising a viscoelastic polymer component, wherein the first surface of the viscoelastic polymer component is adhered to an object in the form of a bottom wall of a tackle box, and wherein an article in the form of a fishing lure is adhered to the second surface of the viscoelastic polymer component.
Figure 7B:
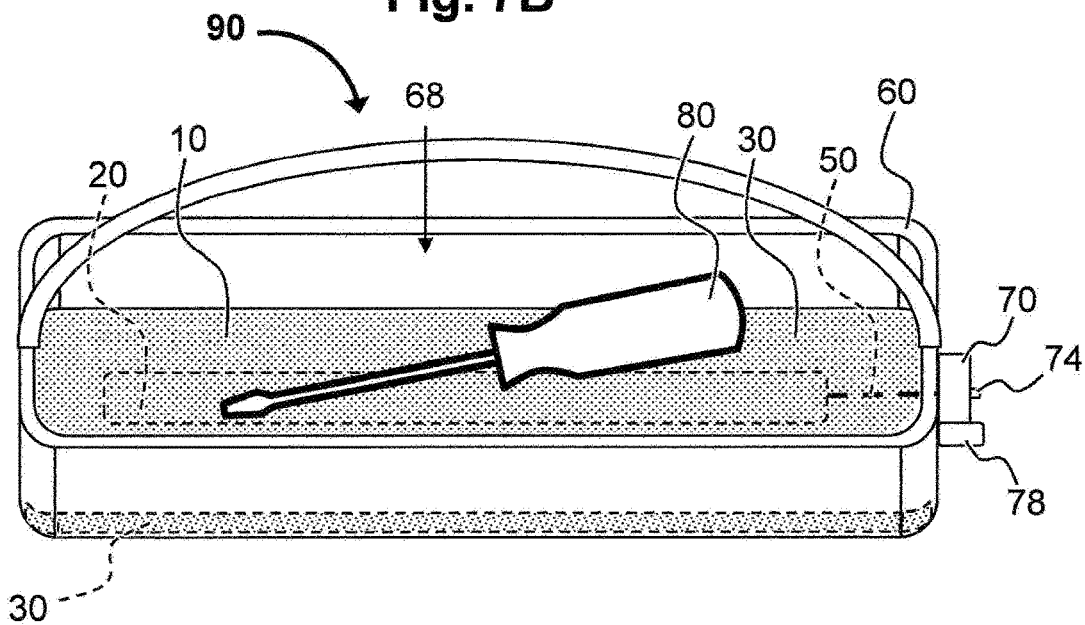
FIG. 7B is a perspective view showing a lighting apparatus of the present invention comprising a viscoelastic polymer component, wherein the first surface of the viscoelastic polymer component is adhered to an object in the form of a bottom wall of a toolbox, and wherein an article in the form of a screwdriver tool is adhered to the second surface of the viscoelastic polymer component.
Figure 7C:
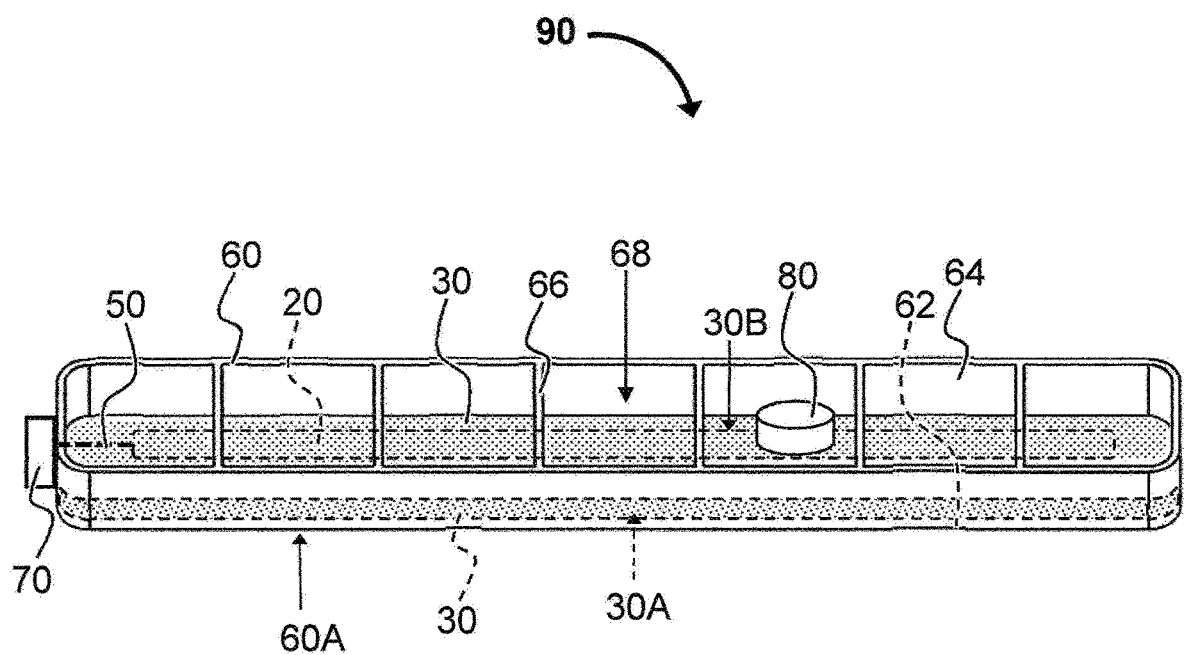
Figure 8:
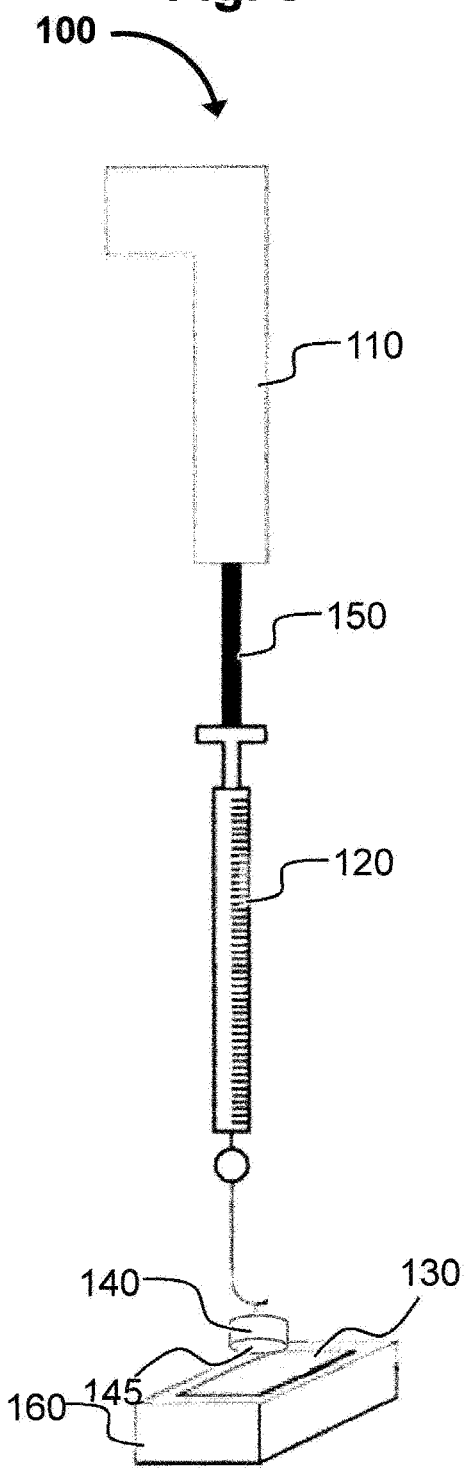

FIG. 7C is a perspective view showing a lighting apparatus of the present invention comprising a viscoelastic polymer component, wherein the first surface of the viscoelastic polymer component is adhered to an object in the form of a bottom wall of a pill box, and wherein an article in the form of a medicine tablet is adhered to the second surface of the viscoelastic polymer component; and FIG. 8 is a front perspective view showing a testing apparatus for the Adhesiveness & Cohesiveness Test.

Repeated use of reference characters in the present specification and drawings is intended to represent the same or analogous features or elements of the present invention.

Test Methods

Time Sensitivity Test

An uncured admixture (such as prepared in accordance with Example 1 below) is spread evenly at a uniform four (4) mm thickness upon a polyvinylchloride apron and allowed to cure into the desired thermoset viscoelastomeric reaction product. The resulting reaction product film is then cut into test panel patch sizes for testing using the testing apparatus depicted in FIG. 8 with the testing procedure being conducted in accordance with the Adhesive & Cohesive Test procedure set forth below, and further performing the optional time dependent properties procedures set forth therein.

Adhesiveness & Cohesiveness Test

Referring to FIG. 8, the illustrated testing apparatus 100 is utilized for testing the adhesive and cohesive properties of various different inventive viscoelastic polymers of the present invention. The test apparatus 100 includes a motor driven actuator 110 (similar to that of a standard remote controlled electric garage door opener, such as a Model 3265, available from The Chamberlain Group, Inc., having a place of business located in Elmhurst, Ill. 60126, U.S.A.). The actuator 110 includes a reversible constant speed motor (2.7 cm/sec which is occluded from view) serving to drive a remotely controlled reciprocating test probe 150 connected to a measuring scale 120 to measure adhesiveness, which is the amount of applied force (in grams) needed to separate each viscoelastic polymer test sample 130 from a polished nickel cylinder 140 having a 1.76 $cm^2$ contact surface area 145, thus providing measurements in units of grams-force per square centimeter ($g_f/cm^2$). A testing platform 160 of a laterally movable form is utilized to provide a solid flat level surface which allows for repositioning of the test sample 130 to provide an accurate repetition of the test results for each tested sample. The testing platform 160 may thus be repositioned to provide a repetition of an untested portion of the test sample 130 for further testing. Accordingly, adhesiveness is measured as the average of ten (10) repetitions upon untested portions of a single viscoelastic polymer sample 130.

The testing procedure is also useful for determining the cohesiveness of the viscoelastic polymer test sample 130. This is accomplished by observing and noting the presence or absence of viscoelastic polymer residue from each viscoelastic polymer test sample 130 upon the test cylinder surface 145 after separating the cylinder 140 from the sample 130. The cylinder surface 145 should be cleaned of any residue between each repetition, and the cohesiveness is measured as the average amount of residue over ten (10) repetitions upon untested portions of a single insert sample 130.

In addition, additional testing can include the application of pressure to the cylinder 140 when in contact with a viscoelastic polymer test sample 130. By measuring the adhesiveness and cohesiveness of each test sample 130 under differently applied sample application pressures, the adhesive and cohesive effects from applying such different adhesive pressures can likewise be determined.

Similarly, adhesion separation differences or changes measured over timed sequence intervals can also be determined so as to provide adhesive data upon a viscoelastic polymer sample's 130 adhesion stability. The test procedure can also be utilized to provide adhesion data upon short interval adhesion increases following an initial adhesive attachment of the cylinder surface 145 to the test sample 130. Differences in adhesiveness between pressure and non-pressure applied test probe over timed intervals can also be determined.

Continuing with FIG. 8, the following more detailed methodology can be used to test adhesiveness and cohesiveness of various test samples 130:

1. Scope
    1.1. This method measures the level of tackiness (adhesiveness) exhibited by adhesive materials and the stability (cohesiveness) of such materials, optionally taking into account time dependent and/or pressure dependent adhesive properties.
    1.2. This test is designed for use with materials that exhibit adhesive properties, but may also be used with materials not explicitly classified as adhesives, including but not limited to materials having adhesive-like properties.
    1.3. Units—The tested values of adhesiveness are based upon grams-force per square centimeter ($g_f/cm^2$) of the force needed to separate the surface 145 of a polished nickel cylinder 140 having a contact surface area of 1.76 $cm^2$ from the test sample 130.
2. Terminology
    2.1. As used herein, the term "adhesive-like" refers to having a sticky quality akin to an adhesive, but derives its sticky quality from molecular structure that forms a molecular attraction (rather than chemical bonded properties) which is releasable from adhered objects without leaving behind residue (i.e., cohesiveness). The test can be applied to an inventive viscoelastic polymer test sample 130, which additionally may be washed with a mild detergent and water to restore its stickiness when dirty.
    2.2. As used herein, the term "tackiness" refers to the adhesiveness quality of feeling sticky to the touch.
    2.3. As used herein, the term "time dependent adhesive" refers to a material in which adhesive strength increases according to duration of the contact time with a contacting surface. Such characteristic is distinctive from pressure sensitive adhesives since no substantial pressure is required to achieve the increased adhesive strength after initial contact.
3. Summary of Test Method Using the Testing Apparatus Depicted in FIG. 8
    3.1. A viscoelastic polymer sample 130 to be tested is secured (generally via the sample's self-adhesive properties) to the testing platform 160.
    3.2. The testing probe 150 of the apparatus 100 is lowered to place the surface 145 of the cylinder 140 onto the sample 130.
    3.3. The surface 145 of the cylinder 140 of the apparatus 100 remains in contact with the viscoelastic polymer test sample 130 for a designated time period.
    3.4. The cylinder 140 of the apparatus 100 is then raised from the sample 130 via the reciprocating probe 150 at a constant speed of 2.7 cm/sec to measure the force in grams required to separate the cylinder surface 145 from the sample 130, as indicated by the measuring scale 120.
    3.5. The measured separating force (adhesiveness) is then calculated and recorded in units of $g_f/cm^2$. In addition, the contacting surface 145 of the cylinder 140 is observed and the amount of residue attached thereto (if any) is recorded to determine cohesiveness. (Note: the surface should be cleaned if residue is present prior to further testing.)
    3.6. Steps 3.1-3.5 are then repeated on untested portions of the sample 130 so as to obtain a total of ten (10) tests per sample, which are then averaged to yield a final result.
    3.7. Optionally, steps 3.1-3.6 can then be repeated over designated contact time intervals so as to determine the time dependent properties of the tested sample 130.
    3.8. Optionally, steps 3.1-3.6 can then be repeated over designated applied pressures so as to determine the pressure dependent properties of the tested sample 130.
4. Apparatus
    4.1. The testing apparatus 100 is illustrated in FIG. 8. Alternative materials and configurations to those stipulated may be used as long as they achieve comparable performance and meet the performance stipulations outlined in Section 4.2 below. Key elements of the apparatus include:
        4.1.1. A reciprocating mobile actuator 150 is responsible for lowering and raising the cylinder 140 onto the material sample 130 at a constant speed of 2.7 cm/sec.
        4.1.2. The scale 120 measures the amount of force in grams required to separate the contact surface 145 of the cylinder 140 from the test sample 130.
        4.1.3. The contact surface 145 of the cylinder 140 is the sole contacting surface with the tested sample 130. The contact surface 145 of the cylinder 140 is a circular polished nickel probe having a total contact surface area of 1.76 $cm^2$.
        4.1.4. The testing platform 160 provides a solid, level surface for accurate test results and secures the tacky test material sample 130 for testing. This platform 160 is laterally movable so as to allow for repositioning of the sample 130 for multiple testing.
    4.2. Regardless of the specific components used:
        4.2.1. The mobile actuator (test probe) 150 must raise and lower the cylinder 140 at a constant speed of 2.70 cm/second.
        4.2.2. The accuracy of the test, the testing apparatus 100 and scale 120 must measure force in grams with an accuracy resolution of five-percent (5%) or better.
        4.2.3. Except for optional pressure applied tests, a constant pressure of 20.0 grams for the duration of the test must be applied by the free-hanging, weighted cylinder 140.
    4.3. The test procedure is conducted at ambient temperatures of 18° C. to 24° C. and most commonly at 21° C.
5. Calibration
    5.1. Prior to first use and at subsequent reasonable testing intervals afterwards, the speed rate of the actuator 150 is monitored to ensure consistency within the standard outlined in Section 4.2.1.
    5.2. Prior to first use, the accuracy of the scale 120 should be verified against a known weight and adjusted or zeroed accordingly.

6. Procedure
   6.1. Assemble the testing apparatus 100.
   6.2. Secure a sample 130 of material to be tested to the testing platform 160, ensuring that the platform 160 (20 gram weight of the platform 160) does not lift free during testing.
   6.3. Lower the testing cylinder 140 onto the test material 130, ensuring even contact between the contact surface 145 and the test material 130, and that the testing scale 150 is neither pulling nor applying pressure to the cylinder 140.
   6.4. Allow the surface 145 of the cylinder 140 to remain in contact with the material sample 130 for the duration of the predetermined contact period.
   6.5. Continue the test by raising the surface 145 of the cylinder 140 from the test material 130.
   6.6. Record the amount of gram-force as measured by the scale 150 needed to separate the surface 145 of the cylinder 140 from the test material 130.
   6.7. Reset the scale 150.
   6.8. Reposition the testing platform 160 so that a fresh (untested) area of the sample 130 is tested by the apparatus 100.
   6.9. Clean the surface 145 of the cylinder 140 after each testing with a lint free cloth.
   6.10. Repeat steps 6.2-6.9 to obtain a total of ten (10) measurements.
   6.11. Optionally repeat steps 62-6.10 for each duration of testing to determine time dependent properties (at timed intervals 15 seconds, 30 seconds, 5 minutes, 10 minutes and 15 minutes).
   6.12. Optionally repeat steps 62-6.10 for each duration of testing to determine pressure dependent properties (by applying incremental predetermined pressures to the cylinder 140).
7. Calculation and Interpretation of Results
   7.1. Calculate the adhesiveness for each of the ten (10) test sample 130 measurements by dividing the force ($g_f$) required for each sample 130 by the contact surface area 145 of the cylinder 140 (1.76 cm$^2$), and then calculate the average of the ten (10) adhesiveness measurements to established a final adhesiveness value. The average tested value is given in the amount of gram-force per square centimeter ($g_f$/cm$^2$) representing the required force to separate the surface 145 of the cylinder 140 from the material sample 130, which serves as a measurement of sample tackiness (adhesiveness).
   7.2. Calculate the cohesiveness for each of the ten (10) observed residue quantities, and then calculate the average of the ten (10) quantities to established a final cohesiveness value. A lower cohesiveness value can be more desirable than a higher value (e.g., wherein a lower value indicates less residue transferred to the contacting surface 145 of the cylinder 140 than a higher value).
   7.3. Repeat steps 7.1 and 7.2 for all iterations tested.

Definitions

It should be noted that, when employed in the present disclosure, the terms "a" and "an" are intended to mean "at least one" of any stated features, elements, integers, steps, components, or groups, etc. and are not intended to be limited to only one of such features, elements, integers, steps, components, or groups, etc. thereof, except where specifically stated as such. In addition, use of the phrase "at least one" is not intended to render other uses of the terms "a" or "an" to be limited to only one of a feature, element, integer, step, component, or group, etc.

It should be noted that, when employed in the present disclosure, the terms "comprises," "comprising" and other derivatives from the root term "comprise" are intended to be open ended terms that specify the presence of any stated features, elements, integers, steps, components, or groups, etc., and are not intended to preclude the presence or addition of one or more other features, elements, integers, steps, components, or groups, etc. thereof.

As used herein, the terms "adhesive" and "adhesiveness" refer to the bonding strength or adhesive release strength of the inventive viscoelastic polymer of the present disclosure to an object or article. The inventive viscoelastic polymer possesses an unexpectedly superior stabilization and a powerful adhesiveness which is releasable from an object or article by a counteracting force overcoming its adhesiveness. Adhesiveness is measured herein according to the Adhesiveness & Cohesiveness Test.

As used herein, the term "article" refers to an element which can be attached to the inventive viscoelastic polymer component (typically the second surface thereof) of the lighting apparatus of the present disclosure.

As used herein, the terms "cohesive" and "cohesiveness" refer to the ability of the inventive viscoelastic polymer of the present disclosure to retain its structural integrity when subjected to separating or peeling forces. The viscoelastic polymer cohesive attributes are further reflected by its tensile strength, adhesive separation from an object or article without leaving any viscoelastomer residue, and its elasticity. Cohesiveness is measured herein according to the Adhesiveness & Cohesiveness Test.

As used herein, the term "component" refers to an element of the inventive lighting apparatus of the present disclosure.

As used herein, the term "element" refers generally to any of a component of the inventive lighting apparatus of the present disclosure, an object or item, and/or an article.

As used herein, the term "object" and "item" refer to an element generally having a surface upon which the viscoelastic polymer component (typically the first surface thereof) of the inventive lighting apparatus of the present disclosure can be attached.

As used herein, the phrase "other lighting apparatus components" refers to components of the inventive lighting apparatus of the present invention excluding the viscoelastic polymer component.

As used herein, the term "substrate" refers to a prefabricated layer (e.g., a film, a sheet, a pad, etc.) generally having a first planar surface and an opposing second planar surface distal to the first planer surface.

These terms may be defined with additional language in the remaining portions of the specification.

DETAILED DESCRIPTION

The invention is generally directed to improved lighting apparatus. The invention may be better understood with reference to the Figures.

With reference to FIGS. 1A-7C, there is provided pursuant to this invention a unique lighting apparatus 10 equipped to uniquely releasably adhere to objects or items 60 at a fixed and stabilized emplacement position. This unique lighting apparatus 10 generally comprises a light 20 in combination with a unique adhesive and cohesive thermoset viscoelastomeric polymer 30, typically having a first adhesive surface 30A, and an opposing second adhesive surface 30B distal to the first surface 30A. The light 20, and optionally other components of the lighting apparatus 10 can be disposed upon the first surface 30A, the second surface 30B, and/or at least partially within the viscoelastic polymer 30 component. In some preferred aspects, the first surface 30A can adhesively adhere, or bond by thermosetting, to an object 60 positioned to contact and engage the first surface 30A upon which the lighting apparatus 10 is emplaced, and/or an article 80 can adhesively adhere to the second surface 30B upon which such article 80 is emplaced. In further aspects of the invention, the lighting apparatus 10 can comprise a variety of additional optional components including, but not limited to, substrates 32, support structures 40, electrical connectors 50, etc.

It has been unexpectedly discovered that the inventive adhesive and cohesive thermoset viscoelastic polymers 30, and substrates 32 thereof, create powerful and unique intermolecular adhesive and cohesive forces in what appears to be a localized intrinsic adhesive polarity charge or attraction, which in turn provides an unexpectedly superior adhesion efficacy when used as a lighting apparatus 10. Compositionally, the adhesive and cohesive thermoset viscoelastic polymers 30 effectively serve to stabilize and immobilize the lighting apparatus 10 against dislodgement from an object 60 until intentionally manually removed from the object 60 upon which it has been adhered to. The lighting apparatus 10 needs only an object 60 of either a solid (i.e., rigid) or flexible construction in order to adhere at a stabilized emplacement position since the exceptional adhesive and cohesive viscoelastomeric properties of the viscoelastic polymer 30 component serve to effectively restrain the lighting apparatus 10, which has been adhesively placed upon an object 60, against any further movement.

Referring now to FIGS. 1A-1E, the lighting apparatus 10 of the present disclosure comprises at least one light 20. Any type of light 20 may be suitable for the invention including, but not limited to, light emitting diodes ("LED's"), ultraviolet ("UV") lights, infra-red lights, luminescent lights, fluorescent lights, halogen lights, xenon lights, solar lights, phosphorescent lights, and the like, and/or combinations thereof. In some preferred embodiments, the light 20 is in the form of a bulb (see e.g., FIG. 1A), though it need not be.

In some aspects, the lighting apparatus 10 can include a light 20 that requires relatively low power (such as an LED or UV light, as compared to a higher power luminescent light exhibiting generally equivalent lumens, for example). In other aspects, the lighting apparatus 10 can include a light 20 that emits relatively low heat (such as such as an LED or phosphorescent, as compared to a luminescent light exhibiting generally equivalent lumens, for example). In still other aspects, the lighting apparatus 10 can include a light 20 that requires low power and exhibits low heat. In yet other aspects, the lighting apparatus 10 can comprise a plurality of lights 20, at least one of which is preferably a low power and/or low heat light.

Figure 1A:
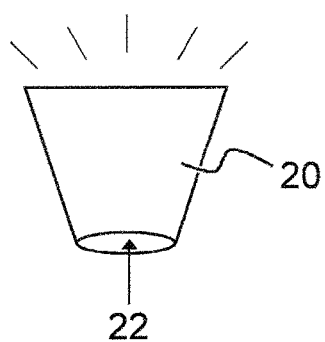
FIG. 1A is a perspective view showing an exemplary light.
Figure 1B:
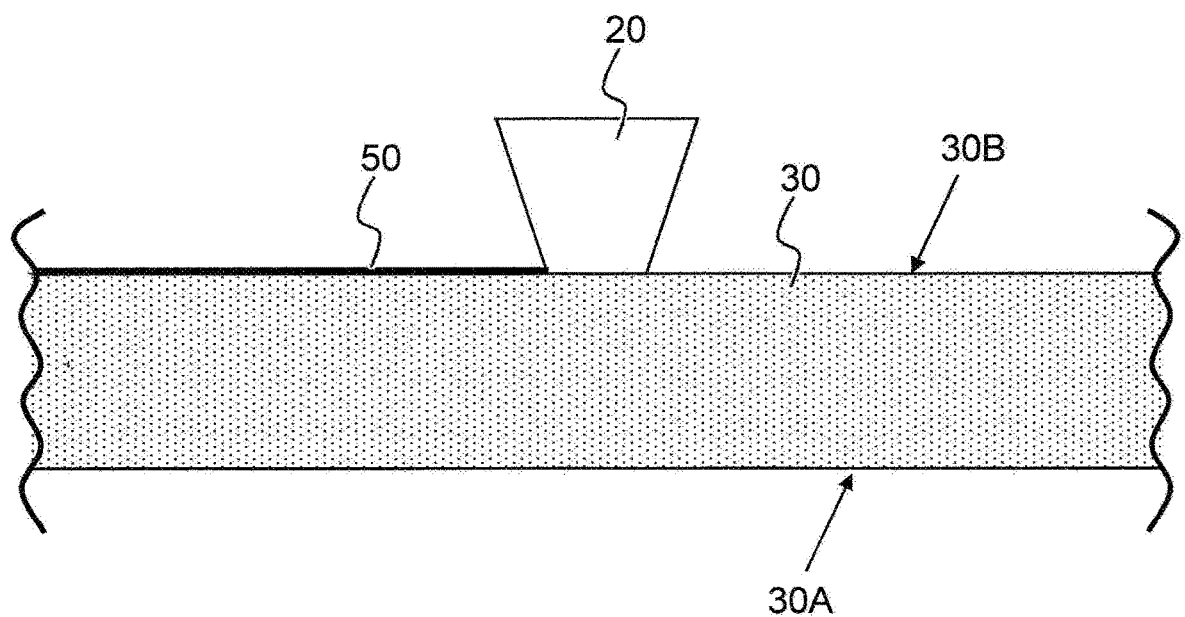
FIG. 1B is a partial side view showing a lighting apparatus of the present invention comprising a light having an optional electrical connector attached thereto disposed upon an inventive viscoelastic polymer component.
Figure 1C:
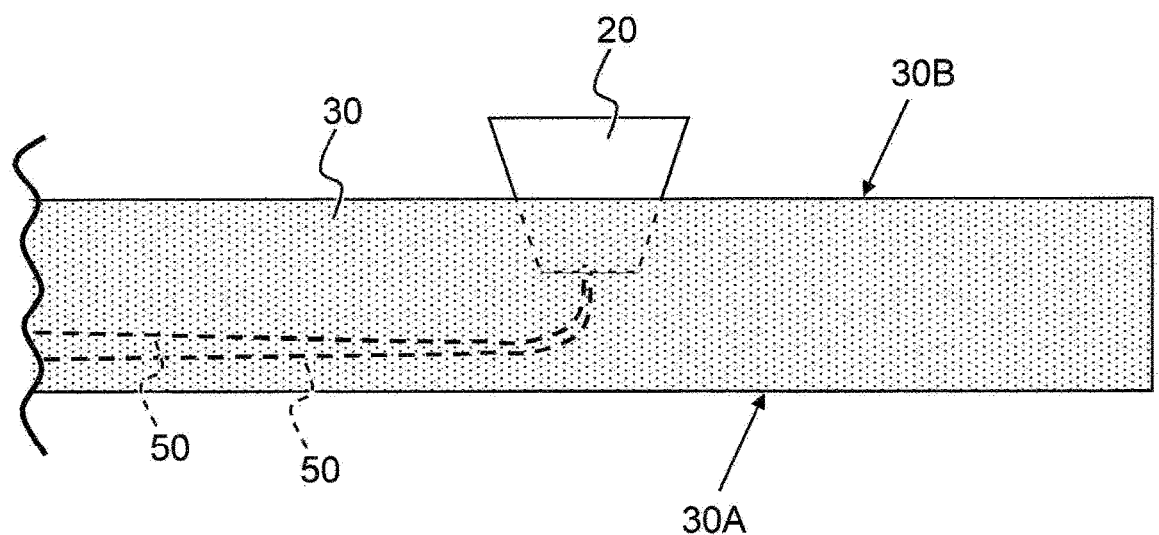
FIG. 1C is a partial side view showing a lighting apparatus of the present invention comprising a light having optional electrical connectors attached thereto and being partially encapsulated within an inventive viscoelastic polymer component.
Figure 1D:
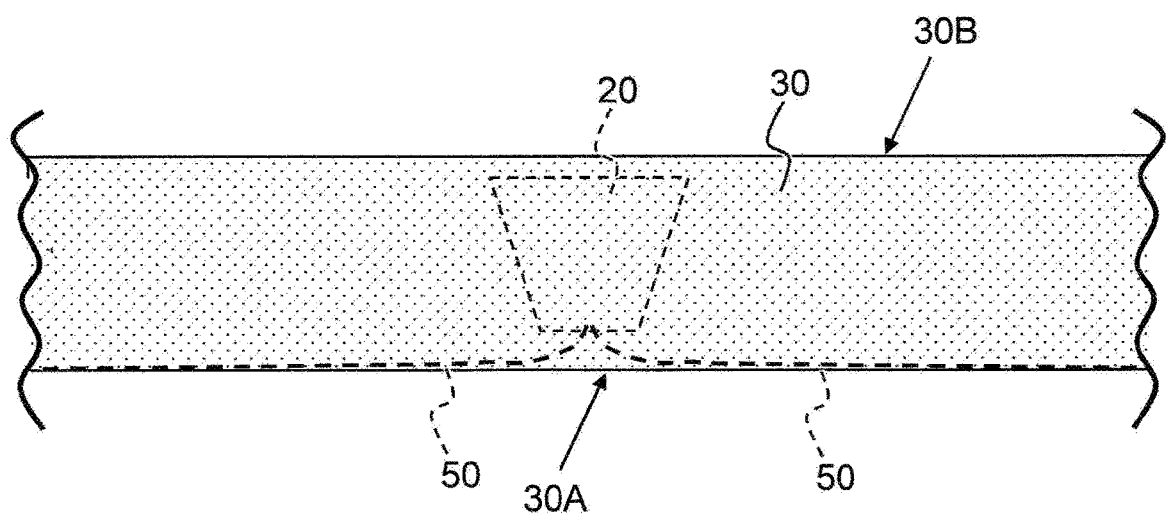
FIG. 1D is a partial side view showing a lighting apparatus of the present invention comprising a light having optional electrical connectors attached thereto and being fully encapsulated by a translucent inventive viscoelastic polymer component.
Figure 1E:
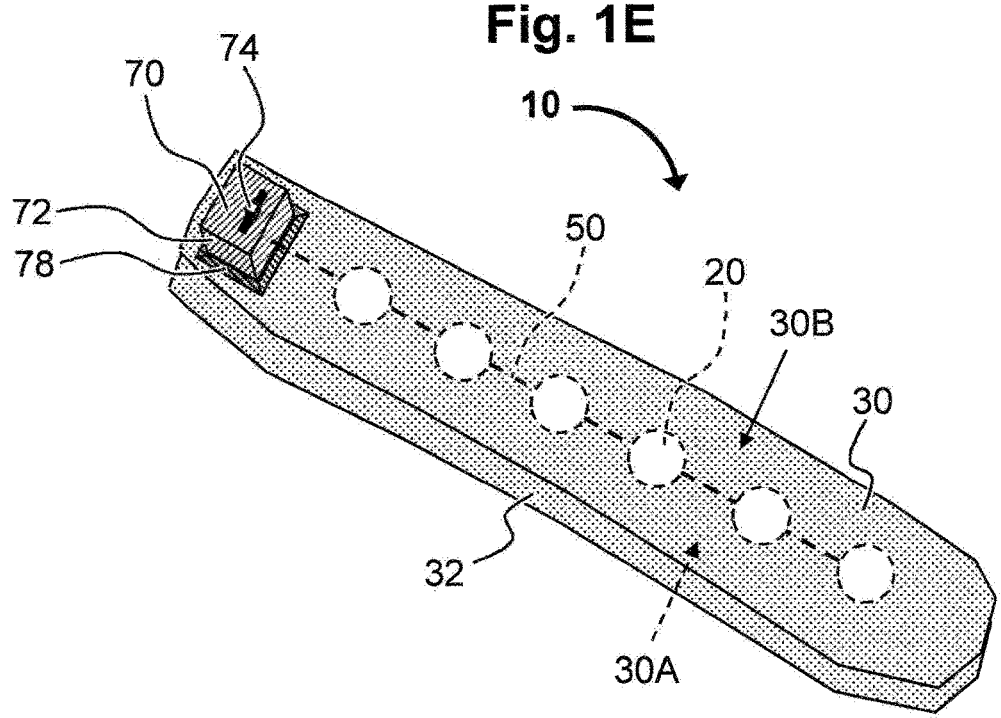
FIG. 1E is a perspective view showing a lighting apparatus of the present invention comprising a plurality of lights having optional electrical connectors attached thereto wherein the plurality of lights are disposed within an inventive viscoelastic polymer component in the form of a substrate.
Figure 2A:
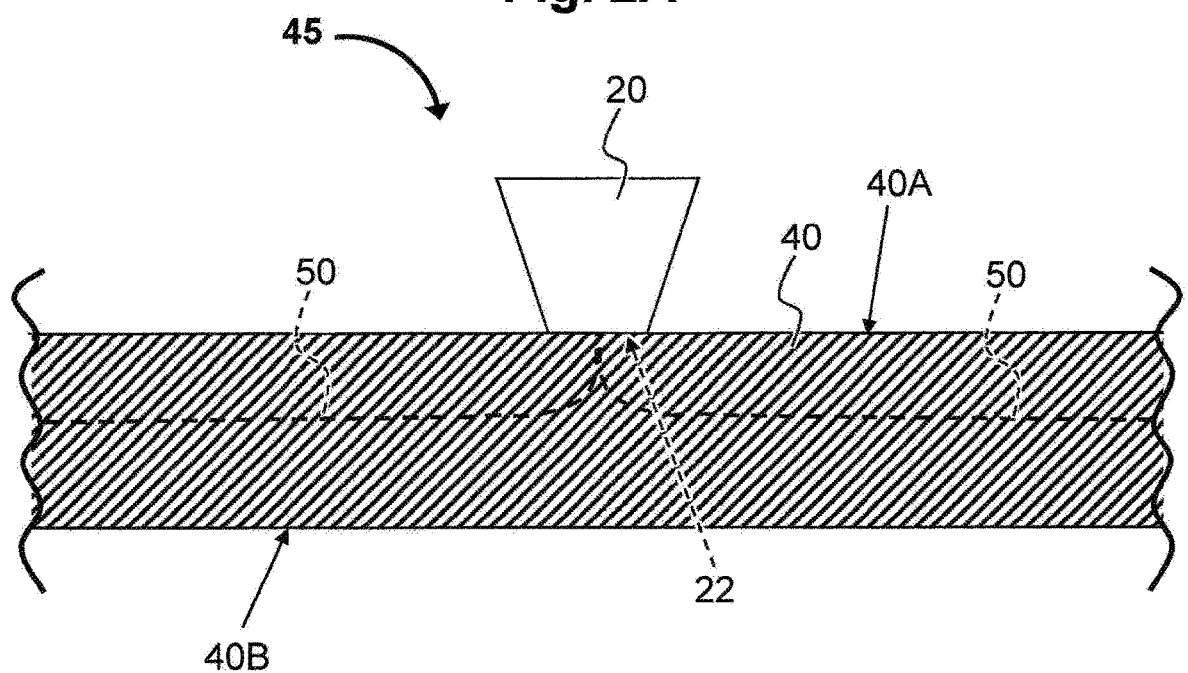
FIG. 2A is a partial side view showing a support structure disposed upon the bottom surface of a light and having optional electrical connectors attached thereto to form a lighting assembly.
Figure 2B:
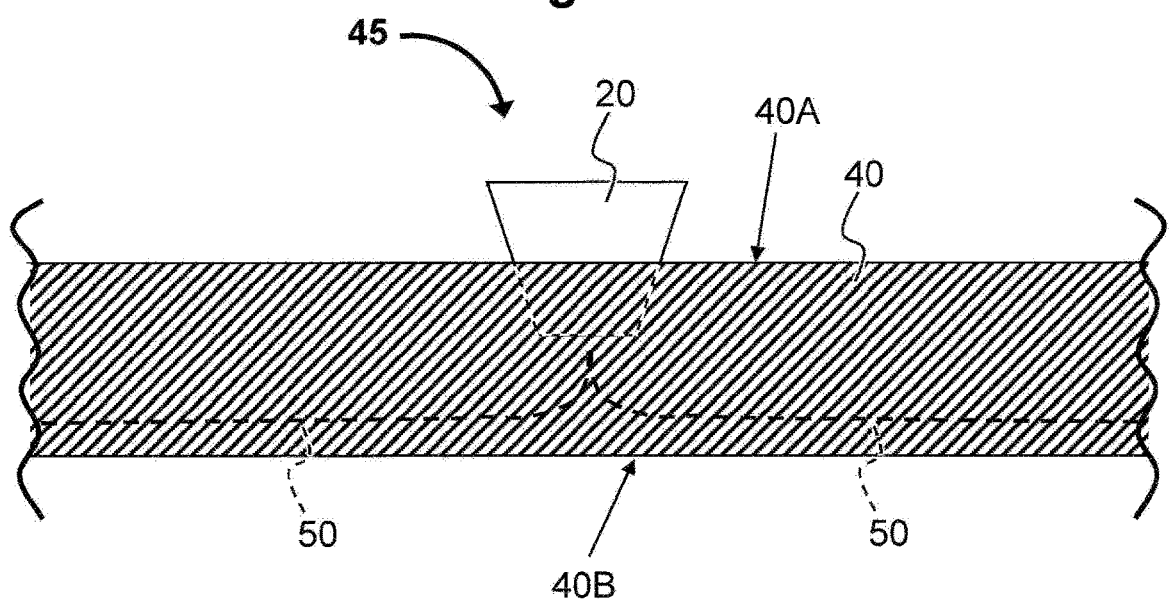
FIG. 2B is a partial side view showing a light partially encapsulated within a support structure and having optional electrical connectors attached thereto to form a lighting assembly.
Figure 2C:
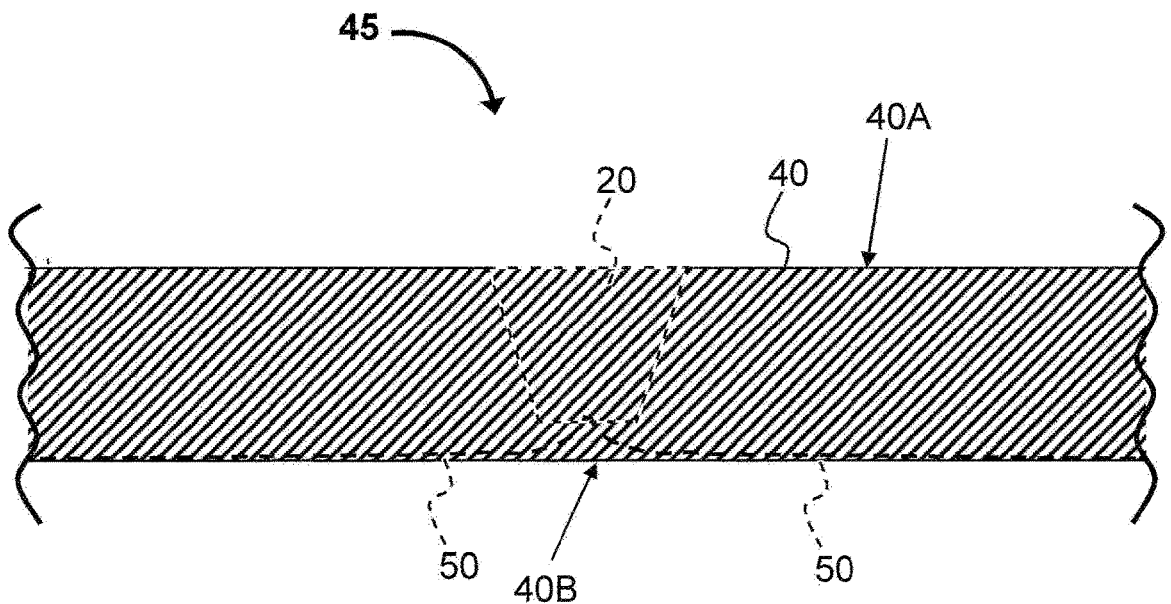
FIG. 2C is a partial side view showing a light substantially encapsulated within a support structure and having optional electrical connectors attached thereto to form a lighting assembly.

In some aspects, the light(s) 20 can be at least partially encapsulated into the viscoelastic polymer 30 (see e.g., FIGS. 1C and 1D). In other aspects, the lights(s) 20 can be releasably adhered, or permanently bonded, onto a surface of the viscoelastic polymer 30 (see e.g., FIG. 1B). In still other aspects, the lighting apparatus 10 can include combinations thereof.

In some aspects, the light(s) 20 can be connected (e.g., electrically connected) to a power source 78. In some such aspects, the light 20 can be self-powering (i.e., having a built-in power source). In other such aspects, the light 20 may require an external power source (i.e., a power source that is separate and/or located a distance away from the light 20). In such embodiments, it may be desirable that the lighting apparatus 10 further comprise an optional electrical connector 50 (e.g., wire, filament, conductive tape, conductive printing, etc.) which connects the light 20 to the external power source. In embodiments having a plurality of lights 20, it may be desirable that one or more optional electrical connectors 50 is utilized to connect at least some of the plurality of lights 20 to a power source 78 that is external. Such plurality of lights 20 connected to a power source via an optional electrical connector(s) 50 may be wired in a series and/or in a parallel configuration, as desired. However, it should be understood that the invention is not limited to a single power source. Rather, the invention can comprise a plurality of the same or different power sources, each electrically connected to one or more lights 20 as desired, without departing from the scope of the invention.

In some aspects having an optional electrical connector 50, such optional electrical connector 50 can be in the form of a live connector disposed upon and/or within the viscoelastic polymer 30 component of the lighting apparatus 10. In other aspects, the optional electrical connector 50 can include an at least partial covering, such as an insulator. In such aspects, the electrical connector 50 and covering can be in the form of a core and sheath arrangement, wherein the electrical connector 50 serves as the core, and the covering serves as the sheath.

In some aspects, the light(s) 20 of the inventive lighting apparatus 10 can be connected to an optional switch 70. In some further aspects of such embodiments, the switch 70 can be a manual switch, such as a toggle or push button switch, for example. In other aspects, the switch 70 can be an automatic switch. For example, one suitable automatic switch can work similarly to a light switch commonly found in current large appliances (e.g., refrigerators, ovens, etc.), such that when a door or lid is shifted from a closed position to an open position, the switch closes a circuit to activate the light(s) 20 of the lighting apparatus 10. In other examples, a suitable automatic switch can be activated via a motion detector, such as those commonly utilized in security lighting, for example. Other manual and automatic switches as will become apparent to those skilled in the art are also suitable for the inventive lighting apparatus 10 without departing from the scope of the invention.

Figure 3C:
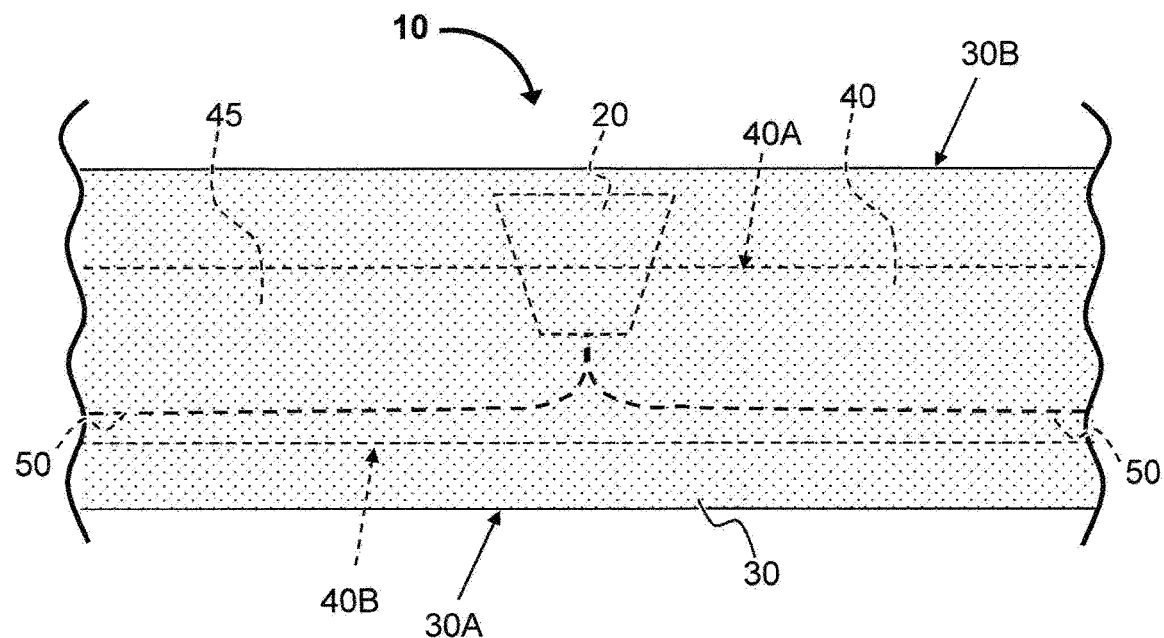
FIG. 3C is a partial side view showing a lighting apparatus of the present invention having a lighting assembly fully encapsulated by an inventive viscoelastic polymer component.
Figure 4:
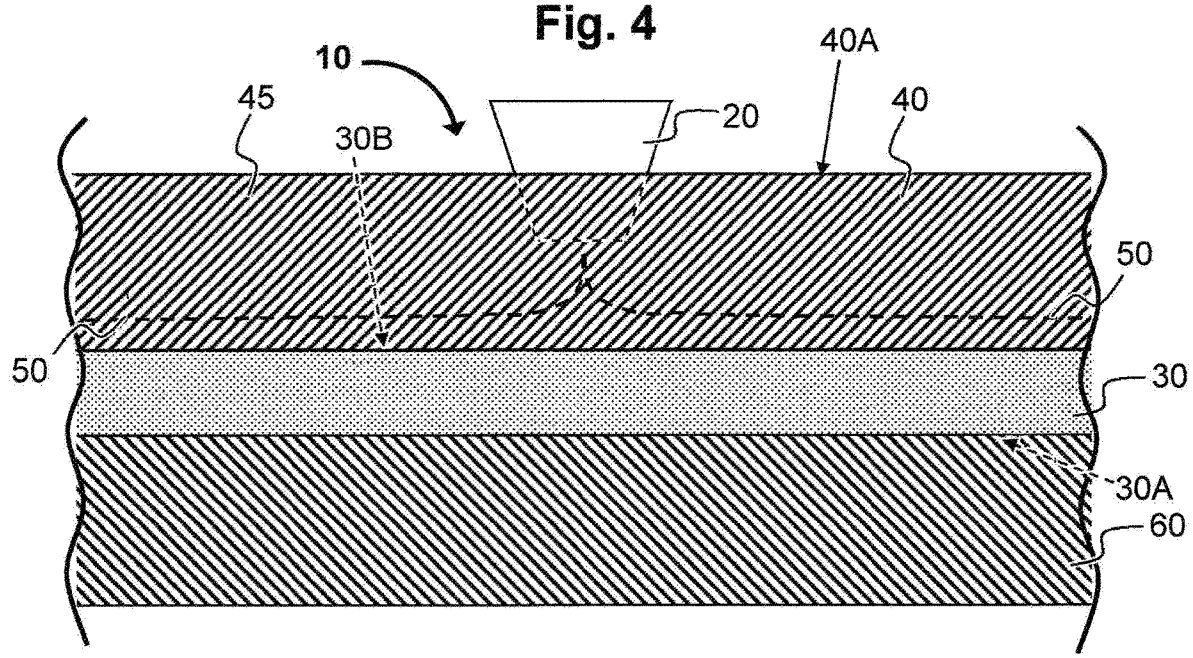
FIG. 4 is a partial side view showing a lighting apparatus of the present invention having a lighting assembly in contact with the second surface of an inventive viscoelastic polymer component, and wherein the first surface of the viscoelastic polymer component is attached to an object.

Referring now to FIGS. 2A-2D, in some aspects, the lighting apparatus 10 can further comprise and optional support structure 40. Such optional support structure 40 can support the light(s) 20 within the lighting apparatus 10, such as to provide protection to the light(s) 20, electrical connectors 50, etc.; maintain the position of the light(s) 20, electrical connectors 50, etc.; and the like. Accordingly, the support structure 40 may be designed to secure one or more components of the lighting apparatus 10, such as lights 20, electrical connectors 50 and/or switches 70, for example, to form a lighting assembly 45. In some aspects, one or more of the lighting apparatus 10 components (typically excluding the viscoelastic polymer 30 component) can be disposed at least partially within (i.e., at least partially encapsulated by) the support structure 40 (see e.g., FIGS. 2C and 2D). In other aspects, one or more of the lighting apparatus 10 components can be disposed upon a surface 40A,40B of the support structure 40 (see e.g., FIG. 2B). In still other aspects, the lighting apparatus 10 components can be disposed as a combination thereof. With reference to FIGS. 3A-3C, in addition, such a lighting assembly 45 can be disposed at least partially within (i.e., at least partially or fully encapsulated), or disposed onto a surface 30A,30B of, the viscoelastic polymer 30 component to form the lighting apparatus 10 of the present invention. With reference to FIG. 4, such lighting apparatus 10 comprising a lighting assembly 45 can further be adhered to an object 60. Likewise, and an article 80 can be adhered to such a lighting apparatus 10 comprising a lighting assembly 45.

Returning now to FIGS. 1B-1E, the lighting apparatus 10 of the present disclosure further comprises a product of a thermosetting reaction media which can be cured to form a flexible viscoelastic polymer 30 component having unique adhesive and/or cohesive properties. For example, in some preferred embodiments, the viscoelastic polymer 30 can have an adhesiveness of at least about 300 grams-force per square centimeter ($g_f/cm^2$), such as at least about 400 $g_f/cm^2$, or at least about 500 $g_f/cm^2$, or greater, as measured by the Adhesiveness & Cohesiveness Test (further described above).

Within the vast field of thermoset viscoelastomers, these newly discovered thermoset viscoelastomers used to form the viscoelastic polymer 30 component have been found to possess surprisingly superior cohesiveness and adhesiveness, rendering them most effective for use with the releasable lighting apparatus 10 herein. The unique efficacy provided by the inventive lighting apparatus 10 fitted with the inventive viscoelastic polymer 30 leverages the unique adhesiveness and cohesiveness which the viscoelastic polymer 30 compositionally and intrinsically provides to the lighting apparatus 10. Furthermore, it has been observed that the lighting apparatus 10 possesses an exceptional stability against any substantial adhesive and cohesive change over prolonged usage time periods (e.g., six (6) weeks or more). Moreover, it has also been observed that the viscoelastic polymer 30 of the lighting apparatus 10 uniquely provides antimicrobial properties (discussed further below). Accordingly, such attributes of the lighting apparatus 10 as described herein set it apart from any other lighting apparatus.

Within the field of adhesive and cohesive materials, it has been discovered herein that there exists a very limited class of thermoset viscoelastomeric reaction products which meet the necessary prerequisite properties for use as the inventive viscoelastic polymer 30 as provided herein. Some unique attributes most suitable for use include, but are not limited to:

1. a viscoelastic polymer 30 comprising a first surface 30A having a releasable adhesiveness which can tenaciously cling onto an adhered component of the lighting apparatus 10 (e.g., light 20 and/or optional electrical connector 50 and/or optional support structure 40, etc.) and/or to the surface of an object 60, but will cleanly and cohesively release from the adhered element without flaking or leaving residue upon application of a counterforce sufficient to overcome the adhesive attraction between the viscoelastic polymer 30 and the adhered element;

2. a viscoelastic polymer 30 comprising a second surface 30B having a releasable adhesiveness which can tenaciously cling onto an adhered component of the lighting apparatus 10 (e.g., light 20 and/or optional electrical connector 50 and/or optional support structure 40, etc.) and/or to an article 80 placed thereupon, but will cleanly and cohesively release from the adhered element without flaking or leaving residue upon application of a counterforce sufficient to overcome the adhesive attraction between the viscoelastic polymer 30 and the element;

3. a soft textured viscoelastic polymer 30 which serves to embed an adhered light 20 (and/or optional electrical connector 50 and/or optional support structure 40, etc.) upon or within its polymeric structure;

4. a viscoelastic polymer 30 of a substantially uniform cohesiveness throughout its entire compositional makeup providing a relatively high tensile strength which permits an adhesive embedding of a light 20 (and/or optional electrical connector 50 and/or optional support structure 40, etc.) with a substantially clean cohesive separation therefrom when removed;

5. a viscoelastic polymer 30 of a substantially uniform cohesiveness throughout its entire compositional makeup providing a relatively high tensile strength which permits an adhesive attachment to an object 60 and/or article 80 with a substantially clean cohesive separation when removed from the object 60 and/or article 80;

6. an adhesive viscoelastic polymer 30, which upon use, may be cleansed of adhering contaminates that adversely affect its adhesive efficacy without substantially diminishing the adhesiveness of the viscoelastic polymer 30;

7. a substantially stable viscoelastic polymer 30 which retains a substantially stable degree of adhesiveness and/or chemical bond to an attached light 20 (and/or optional electrical connector 50 and/or optional support structure 40, etc.);

8. a substantially stable viscoelastic polymer 30 which retains a substantially stable degree of adhesiveness and/or chemical bond when attached to a light 20 (and/or optional electrical connector 50 and/or optional support structure 40, etc.) over prolonged usage periods (e.g., six (6) weeks or more);

9. a substantially stable viscoelastic polymer 30 which retains a substantially stable degree of adhesiveness and/or chemical bond when attached to an object 60 over prolonged usage periods; and 10. a viscoelastic polymer 30 which has an adhesive adherence to a light 20 (and/or optional electrical connector 50 and/or optional support structure 40, etc.), an object 60 and/or an article 80 of at least about 300 $g_f/cm^2$, as measured by the Adhesiveness & Cohesiveness Test procedure;

In preferred embodiments, the inventive viscoelastic polymer 30 compositionally possesses a tenacious adhesiveness and cohesiveness in the form of a highly localized adhesive attraction to a light 20 (and/or optional electrical connector 50 and/or optional support structure 40, etc.) or an article 80 placed upon the viscoelastic polymer 30, as well as to objects 60 upon which the viscoelastic polymer 30 is applied thereto. Normal usage is typically effectuated by a slight pressing of such light 20 (and/or optional electrical connector 50 and/or optional support structure 40, etc.) against the first surface 30A or second surface 30B of the viscoelastic polymer 30 component of the lighting apparatus 10, which in turn, causes an indentation and embedding of the light 20 (and/or optional electrical connector 50 and/or optional support structure 40, etc.) within the viscoelastic polymer 30, along with a concomitant increase in overall interfacial contact area (due to the encapsulating effect of the indentation) and an apparent localized intermolecular adhesiveness therebetween. Similarly, normal usage is further typically effectuated by a slight pressing of the first surface 30A of the lighting apparatus 10 against an object 60, which in turn, causes an adherence of the interfacial contact area of the first surface 30A of the viscoelastic polymer 30 and the object 60, along with an apparent localized intermolecular adhesiveness therebetween. In addition, any surface aberrations on the object 60 can cause indentations and embedding of the aberrations within the viscoelastic polymer 30, along with a concomitant increase in overall interfacial contact area (due to the encapsulating effect of the indentation). Similarly, normal usage can be further typically effectuated by a slight pressing of an article 80 against the second surface 30B of the lighting apparatus 10, which in turn, causes an indentation and embedding of the article 80 within the viscoelastic polymer 30, along with a concomitant increase in overall interfacial contact area (due to the encapsulating effect of the indentation) and an apparent localized intermolecular adhesiveness therebetween. Accordingly, soft textured adhesive elastomers (e.g., soft rubber type cohesives) and particularly thermoset viscoelastomers which possess the aforementioned prerequisitial adhesiveness and cohesiveness properties, along with release attributes, may be utilized for this purpose.

For the purpose of conciseness, the invention will be generally described herein where a component of the lighting apparatus 10 (other than the viscoelastic polymer 30 itself) can be disposed on either the first surface 30A, the second surface 30B, or at least partially within the interior structure of the viscoelastic polymer 30 component; where the first surface 30A of the viscoelastic polymer 30 component can be disposed upon an object 60 (further defined above); and where an article 80 (further defined above) can be disposed upon the second surface 30B of the viscoelastic polymer 30 component. However, it should be understood that any element (i.e., a component of the lighting apparatus 10, an object or item 60, and an article 80) can be disposed upon the first surface 30A, the second surface 30B, or at least partially or entirely within the viscoelastic polymer 30 component of the lighting apparatus 10, without departing from the scope of the invention.

Due to the fluid flow characteristics of the thermoset viscoelastomeric reaction product under stress and its thermoset structure, the polymeric materials most suitably useful to produce the viscoelastic polymer 30 of the inventive lighting apparatus 10 include those commonly referred to as viscoelastomers. The thermoset viscoelastomeric reaction products and suitable resulting viscoelastic polymers 30 for use herein broadly embrace a class of thermoset viscoelastomeric reaction products characterized as having a sufficient pliable character to embed lighting apparatus 10 components (lights 20, electrical connectors 50, support structures 40, etc.) within its contacting surface area and a sufficient adhesive and cohesive attraction to tenaciously adhere other lighting apparatus 10 components placed upon the viscoelastic polymer 30 component's surface 30A, in addition to having a sufficient pliable character which allows the lighting apparatus 10 to generally mold to the shape of an object 60 in contact with its first surface 30A, having sufficient adhesive and cohesive attraction to tenaciously adhere to such object 60 when the lighting apparatus 10 is placed thereupon, while also remaining substantially intact upon removal of the lighting apparatus 10 from the object 60.

Particularly effective as an inventive viscoelastic polymer 30 herein is a novel class of thermoset viscoelastomeric reaction products which unexpectedly possess a releasable but highly powerful adhesive and cohesive efficacy. Molecularly, the thermoset viscoelastomeric reaction products appear to possess superior intermolecular adhesiveness and cohesiveness which renders the viscoelastomeric reaction product uniquely adaptable for use as the viscoelastic polymer 30 component in the lighting apparatus 10 herein. The creation of such unique thermoset viscoelastomeric reaction products and the viscoelastic polymer 30 resulting therefrom compositionally involves providing a viscoelastomeric molecular structure which is cured beyond its glass transition state, and which significantly contributes towards an increase in adhesive tack as exerted by the viscoelastic polymer 30 upon an element coming into contact with its strong adhesive surface. This effect may be accomplished by creating a thermosetting reaction media which compositionally favors the development of a highly adhesive and cohesive thermoset viscoelastomeric reaction product for use as the viscoelastic polymer 30 component. Upon mixing and curing the reaction media, the resulting thermoset viscoelastomeric reaction product provides not only unexpectedly superior adhesive and cohesive attraction properties, but also other unique attributes which are significantly beneficial to the lighting apparatus art. It is believed that the molecular makeup and unique adhesive and cohesive attributes of the viscoelastic polymer 30 will, upon engagement of an element (i.e., other lighting apparatus 10 components and/or objects 60 and/or articles 80), provide an interfacing surface characterized as having apparent surface asperities and/or protuberances which effectively allows for an increase in the total area of contact between the viscoelastic polymer 30 and any such elements. This phenomena, in combination with a powerful adhesiveness, as well as an embedding of elements within the viscoelastic polymer 30 structure (e.g., as due to viscoelastomeric properties) results in an unexpectedly powerful adhesive bonding and restraint of such elements to the viscoelastic polymer 30. In general, the adhesive bonding of an element to the viscoelastic polymer 30 may actually be substantially greater than the gravitational forces exerted upon such element itself, as evidenced by an adhesive retention of an element by the viscoelastic polymer 30 even when the adhered element is rotated to an upside-down, gravity-defying position.

In some preferred embodiments of the present invention, the reaction media can comprise a cross-linked elastomeric constituent (e.g., triols), a straight chain elastomeric constituent (e.g., diols), a hardener, an effective amount of plasticizer, and a catalyst. For example, a non-limiting, exemplary viscoelastic polymer 30 of the inventive lighting apparatus 10 can be derived from a thermoset viscoelastomeric reaction product formed by selectively preparing a thermosetting precursor reaction media which provides a properly configured carbamate thermoset linkage (e.g., urethane) for the thermoset viscoelastomer. In general, the applicable thermosetting polyurethane precursor mixes for preparing the viscoelastic polymer 30 will typically include a balanced amount of a polyol prepolymers (e.g., diols and triols), reacted with a ring-opening species of a hardener (e.g., amines, amides, mercaptans, anhydrides, polycyanates such as a diisocyanate, etc.), combined with a plasticizer (e.g., polarized plasticizer), reacted in the presence of a catalyst, along with suitable reaction conditions (e.g., reaction temperatures, etc.). The ratio of polyol reactants, hardeners, catalyst, reaction temperatures, etc. are pre-selected with an appropriate balance given to the diol and triol reactants to molecularly create the appropriate cross-linkage and linear linkage needed in combination with selective plasticizers and amounts thereof to provide the unique stability, adhesiveness and cohesiveness of the thermoset viscoelastomeric reaction product for the viscoelastic polymer 30. Thus, the thermosetting reactants are chosen so as to avoid an undesirable high degree of cross-linkage and a corresponding high glass transition temperature. Accordingly, reaction conditions and reactants which favor a more linear, adhesive and cohesive viscoelastomeric thermoset backbone structure receptive to polar plasticizer loading are particularly well suited for use in providing the viscoelastic polymer 30 herein. In contrast, the use of reactants, catalysts, reaction temperatures, etc. resulting in excessively cross-linked thermoset polymers without sufficient straight chain polyether bridging between the cross-linkages are generally unsuitable to create the desired adhesiveness and cohesiveness for the unique thermoset viscoelastomeric reaction product and the viscoelastic polymer 30 derived therefrom.

In one non-limiting, exemplary embodiment, the desired flexibility, adhesive and/or cohesive characteristics can be achieved for a viscoelastic polymer 30 of the lighting apparatus 10 of the present invention via utilizing a reaction media containing about 15 parts to about 30 parts by weight of a two-functional polyether polyol (i.e., polyether diol) (e.g., ELASTOCAST C-4057, available from BASF Corporation, having a place of business located in Ludwigshafen, Germany), about 15 parts to about 35 parts by weight of a three-functional polyether polyol (i.e., polyether triol) (e.g., ELASTOCAST C-4018, available from BASF Corporation), about 4 percent to about 10-percent by weight (4 wt %-10 wt %) of methylene diphenyl diisocyanate based glycol prepolymer (e.g., ELASTOCAST TQZ-P23, available from BASF Corporation, or ISONATE 2181 and/or RUBINATE 1790, each available from Dow Chemical having a place of business located in Midland, Mich., USA), an epoxidized soybean oil (commonly referred to in the trade as ESO) plasticizer in an amount ranging from about 25-percent to less than about 50-percent by weight (25 wt %-50 wt %) of the total reaction media weight, and a catalytic amount of suitable catalyst (e.g., bismuth (3+) neodecanoate—such as COSCAT 83, available from Vertellus Specialties having a place of business located in Zeeland, Mich., USA) typically at a catalytic concentration ranging from about 0.1-percent to about 0.6-percent by weight (0.1 wt %-0.6 wt %) of the total reaction media weight.

In preferred embodiments, the viscoelastic polymer 30 comprises a carefully measured amount of cross-linked and straight chain linkage structures. Traditionally, polyurethanes are generally formed by reacting a polyol with an isocyanate, usually a di- or polyisocyanate such as the aromatic isocyanates (e.g., typically a diphenylmethane diisocyanate-MDI or toluene diisocyanate-TDI) and aliphatic isocyanates such as hexamethylene diisocyanate (HDI) or isophorone diisocyanate (IPDI) in a prepolymer form which serves as the polyurethane isocyanate reactant in a reaction media which may contain an epoxidized vegetable oil as the major reaction media component. The reactant components include the isocyanate prepolymers reacted diols and triols polyoxyalkylene polyol prepolymers, such as polyethers, having terminal hydroxyl groups (e.g., polyoxyethylene and/or polyoxypropylene diols and triols) typically of a molecular weight greater than about 1000.

In essence, the diols and triols useful in preparing the thermoset reaction products of a desired polymerizate structure are derived from oxygen containing hydrocarbyl diols and triols of a molecular weight of at least about 1000 and include repetitive oxygen containing functional groups, such as provided by the polyester and polyether groupings. It is believed that, due to the oxygen electron scavenging effect to satisfy its 2-s orbital needs, these repetitive internal oxygen-containing groupings, when sandwiched between cross-linkages, provide countless polarized enclaves for uniformly hosting corresponding massive polarized plasticizer concentrations within the polymeric structure to collectively create a synergistic cohesive and adhesive effect thereupon. Although the aforementioned viscoelastomeric reaction media primarily centers about viscoelastomers prepared from thermosetting reaction media incorporating a balanced cross-linkage triol and diol ratio with the cyano reactant in the presence of a sufficient amount and type of plasticizer to provide the desired adhesive and cohesive viscoelastic polymer 30, it is contemplated herein that this technology may also apply to other thermoset viscoelastomeric producing reaction products having a properly balanced cross-linked molecular structure separated by a proper amount of straight chain polyoxy linkages and polarity in the presence of sufficient adhesive contributing plasticizer to yield a viscoelastic polymer 30 derived from the resultant thermoset viscoelastomeric reaction product having a comparable stable cohesiveness, adhesiveness and releasability, without departing from the scope of the invention.

When utilizing ether polyols herein, the basic molecular structure of the thermoset reaction product typically requires a controlled cross-linked structure by balancing the dihydroxy to trihydroxy polyalkylene oxide ratio to create a thermoset viscoelastomer having a sufficient quantum of straight chain polyether linkages. The polar oxygen rich diol reactant serves to separate, and becomes sandwiched between, the cross-linking triol polymerizate linkages. The effective reduction in cross-linkage does not change its thermoset viscoelastomeric classification since its viscoelastomeric properties are retained. It is believed that the controlled thermoset structure permeating the reaction mass creates a controlled polar density of cross-linked polyethers interspersed amongst straight polyether chain bridges to provide a unique labyrinth structure which apparently provides an appropriate polarity and allows for an effective loading of the necessary adhesive and cohesive contributing factors which include the use of plasticizer, such as those commonly known in the trade as plastic plasticizers.

Polyols of a relatively high molecular weight can effectively serve as thermoset viscoelastomeric cross-linking and straight chain building components for the intertwining thermoset viscoelastomeric polymeric structure, which when properly balanced, provide a plasticizer-friendly viscoelastomeric polymeric structure of a well-balanced straight and cross-linked linkages of an appropriate polymerizate configuration and molecular polarity for plasticizer loading. On a reactant weight percentage basis, the diols are generally recognized as being less effective than the polyols (i.e., triols) in producing shock absorbing polymeric structures, but are extremely effective herein in creating the desired viscoelastomeric polymeric structure necessary for plasticizer loading and imparting the desired unique adhesiveness, cohesiveness and release characteristics for the viscoelastic polymer 30 of the lighting apparatus 10. A judicious diol to triol balance enables a balanced proportion of polarized plasticizing components to effectuate the superior adhesiveness and cohesiveness within the carefully structured thermoset reaction product structure. To achieve the desired plasticizing adhesive and cohesive efficacy for the viscoelastic polymer 30, the straight chain diol precursors are typically of a relatively high molecular weight as may be provided by a polyether sequence, which at increased reaction media concentration, creates a more linear thermoset polymeric polyoxy structure while also serving to lessen the cross-linkage density. In general, the desired plasticity and flexibility, along with desired polarity, adhesiveness and cohesiveness may be accordingly effectively effectuated via interpolymerizing the proper amounts of the thermosetting higher molecular weight diols and triols of polyols (e.g., molecular weight of 2,000-10,000) along with other thermosetting isocyanate reactants and plasticizers at the appropriate reaction media amounts. Useful polyether diols herein characteristically comprise a straight polyether molecular chain having two terminal hydroxyl groups. In contrast, the polyether triols characteristically have two terminal cross-linking reactive hydroxyl groups and one additional hydroxyl group leading to more polyfunctional cross-linking sites in the thermosetting reaction media.

Suitable polyether diols and triols are available at various chain lengths, typically ranging from about 1000 to about 20,000 molecular weight. More preferably, the polyether diols and triols utilized herein will have a molecular weight of less than about 15,000, such as a molecular weight of less than about 10,000. Since there exists definitive advantages in maintaining fluidity during the initial mixing and optional prefabrication steps (i.e. forming a viscoelastic polymer 30 into a substrate 32 form), the more fluid polyethers tend to be more desirable for most such applications. Examples of suitable diol and triol reactants applicable herein can include the polyoxyethylene and polyoxypropylene diols and triols thereof having a molecular weight generally ranging from about 1000 and about 8000. In some desirable aspects, the polyether diols having a molecular weight ranging from about 2000 to about 6000, and the polyether triols having a molecular weight ranging from about 2000 to about 8000, more particularly the polyether triols having a molecular weight ranging from about 3000 to about 5000, can be particularly effective for use herein.

Care needs to be exercised as to the extent of cross-linkage and intervening polyoxyalkylene linkage separating the cross-linking site. In some aspects, this can be accomplished via a diol to triol content weight ratio from about 7:13 to about 13:7, more particularly from about 2:3 to about 3:2, to provide the desired straight chain polyether linkage and cross-linkage density.

The triols within the reaction media cause cross-linking at the three available hydroxyl groups, whereas the diols provide an uncrossed-linkage or straight chain linkage within the thermoset polymeric structure. In order to achieve a highly effective stable adhesive and cohesive viscoelastic polymer 30, a proper proportional amount of cross-linkage and straight chain linkages is necessary. The thermoset polymeric structure necessitates somewhat of a lessened cross-linked structure along with a more pronounced presence of intervening straight chain polar attracting linkages to provide a more flexible viscoelastomeric backbone chain of an appropriate polarity for the hosting of polarized plasticizers therein. This creates an intertwining backbone chain providing an excellent attractive force and cohesive polar alignment of plasticizing agent throughout the entire viscoelastomeric mass. As noted above, exemplary useful triols and diols have repetitive oxygen groups of the higher molecular chains such as the polyethers and polyesters containing the polymerizable terminal hydroxyl groupings. Since, in some preferred aspects, it is desirable to utilize polymerizable reactants which provide a lower workable viscosity, such as for prefabrication of the curing reaction media into a desired manufactured form (e.g., a viscoelastic polymer 30 in the form of a substrate 32), the more fluid diols and triols (as well as plasticizers) provide a more easily workable viscosity range.

Accordingly, a resultant reaction product having balanced cross-linkage and straight chain polarized linkages with a balanced plasticizer content homogeneously distributed within the polymeric network has been found to unexpectedly exhibit superior adhesiveness and cohesiveness, rendering it particularly useful as a viscoelastic polymer 30 for the inventive lighting apparatus 10 herein. When cured, the reaction media creates a thermoset chain, which when properly loaded with an effective amount of a plasticizer, becomes homogeneously distributed within the thermosetting reaction media to provide the desired adhesive and cohesive characteristics.

The adhesive and cohesive stability of the resultant thermoset viscoelastomeric reaction product requires a delicate balance between molecular cross-linkage and polar aligning straight chain thermoset moieties bridging structure (e.g., diol to triol ratio), as well as the type and amount of plasticizer within the thermosetting reaction media. For example, as the diol to triol ratio of the reaction media is increased, the resulting thermoset reaction product tends to form a more permanent (i.e., less releasable) bond when placed in contact with an element. In another example, as the plasticizer content of the reaction media is decreased, the resulting thermoset reaction product tends towards an increasingly firm and decreasingly tacky form. By an atypical reduced plasticizer content and a judicious control of the diol to triol ratio, a viscoelastomeric thermoset reaction product ideal for use as the viscoelastic polymer 30 of the lighting apparatus 10 is possible.

In some preferred embodiments, the viscoelastic polymer 30 can comprises a hardener. Such hardeners are typically combined with the thermoset resins (i.e., the cross-linking and straight chain linkage structures). Suitable hardeners include, but are not limited to amines, amides, mercaptans, anhydrides, polycyanates such as a diisocyanate, an isocyanate prepolymer hardener, such as the aliphatic, aromatic, heterocyclic, etc. polyisocyanates, cycloaliphatic, arylaliphatic, isocyanates, etc.

In preferred embodiments, the viscoelastic polymer 30 can comprise a plasticizer. It has been found herein that the appropriate plasticizer content in combination with an increased polyether diol concentration within the thermosetting reaction media increases adhesiveness stability, cohesiveness and tensile strength, as well as thermoset softness. For example, an increase in the proportionate amount of polyether diol to polyether triol ratio, in combination with the plasticizer, provides improved adhesive stability, which effectively permits the viscoelastic polymer 30 formed from the resulting reaction product to functionally possess a sufficient releasable adhesion of an element, even when the lighting apparatus 10 is used over a prolonged period of time. It has also been found herein that a loading of the reaction media with a lower molecular weight polar plasticizer permits a reduction in the total required plasticizer content, which in combination with an increased polyether straight chain linkage, provides a viscoelastic polymer 30 possessing an unexpected adhesiveness and releasability efficacy when used in the inventive lighting apparatus 10. Indeed, such lower molecular weight plasticizers tend to contribute to a more fluid curing reaction media, which can then more easily spread out onto an object 60 or be fabricated into a substrate 32, if desired.

In some preferred aspects, the viscoelastic polymer 30 can be derived from a unique thermosetting reaction media containing a cohesive mass of plasticizing agents structurally supported by a thermoset polymerization which provides an appropriate polarized level of molecular cross linkage and bridging of straight chain linkages within the resulting thermoset viscoelastomeric reaction product. The subsequently cured viscoelastic polymer 30 formed from such unique reaction media possesses a uniquely superior adhesive ability to cling onto contacting elements with an intrinsic cohesive property when properly fabricated to selectively release an adhered element therefrom by applying an outwardly pulling force sufficient to overcome the tenacious adhesive forces bonding the element to the viscoelastic polymer 30. In addition, the adhesive separation breaks cleanly from the adhered element, leaving substantially no residue, since the viscoelastic polymer 30 inherently possesses sufficient internal cohesiveness to tenaciously retain its structural integrity.

Although the thermoset viscoelastomeric structure is especially adapted to loading with a host of plasticizers, plasticizers having a polar attraction to the viscoelastomeric polymeric structure are particularly applicable. It is believed that the molecular electronic attraction contributes to the unique adhesive and cohesive properties within the resulting thermoset viscoelastomeric reaction product. Since the plasticizers are not effectively loadable into a cured thermoset viscoelastomer, the plasticizing reagents are necessarily uniformly incorporated into the thermosetting viscoelastomeric reaction media to achieve the desired uniform and homogeneous distribution thereof throughout its entire uncured composition. It is believed that the thermosetting conditions uniformly align the polymerizate reactants with an effective synergistic polar positioning and alignment of the polar attracting molecular chain sections of the thermoset reactants with the plasticizer to provide for a highly effective polarized plasticizer loading and alignment therewithin. This permits a tenacious and cohesive loading of plasticizer without any evidence of plasticizer seepage or separation from its hosting thermoset viscoelastomeric polymeric structure.

In general, plasticizers which are suitable as plasticizing agents for polyvinyl chlorides are generally applicable for use as reaction media plasticizers herein. Plasticizers of a higher dipole moment (e.g., dibutyl sebacate-DBS-dipolar moment 2.48D) will tend to impart certain desired properties to the polymerizate. Illustrative of plasticizing agents which may be combined with the thermosetting reaction media include the ester plasticizers such as sebacates, adipates, terephthalates, dibenzoates, gluterates, phthalates, azelates, etc. of the C1-C18 chain ester type adhesiveness. However, different blends of the ester plasticizers may be co-blended into the thermosetting reaction media to create or modify the effective working viscosity as in the curing or cured form. For unexpectedly superior adhesiveness, cohesiveness and workability, plasticizers of a dipolar moment of more than 1.5 D, such as more than 2.0 D, may be utilized for this purpose. Epoxidized triglycerides such as the epoxidized animal and vegetable oils are especially effective as a plasticizer component in the thermosetting viscoelastomeric reaction media and especially at levels typically less than about fifty-percent by weight (50 wt %) of the total reaction media weight, such as less than about forty-percent by weight (40 wt %), or less than about thirty-five-percent by weight (35 wt %), or less than about thirty-percent by weight (30 wt %) of the total reaction media weight, for improved performance. The incorporation of a lower molecular weight ester plasticizer (e.g., less than 400 MW), such as an polyalkylene ester plasticizer for example, in combination with epoxidized triglyceride plasticizer can be utilized to provide a better flowing or easier fabricating form of the reaction media without adversely affecting its desirable thermoset properties.

Illustrative ester plasticizing agents of a high dipole moment include the dibutyl, dimethyl, diethyl, and dibutyl esters of sebacates, the adipates, the isophthalates, the phathalates, the maleates, the azelates, the gluterates, etc. The total plasticizer concentration will most suitably range from about 20% by weight (20 wt %) to about 45% by weight (45 wt %), such as from about 25% weight percent (25 wt %) to about 40% by weight (40 wt %), with the weight ratio of epoxidized triglyceride to non-epoxidized plasticizer typically ranging from about 1:0 to about 1:3, such as from about 1:1 to about 3:1.

In some desirable aspects, the reaction media can comprise plastic plasticizer, such as a triglyceride plasticizer (e.g., epoxidized vegetable oil). Desirably, such a plasticizer will be present in the reaction media in an amount of less than about 50-percent by weight (50 wt %) of the total reaction media weight (although such amount of oil may still constitute the predominant reactant reaction media ingredient). In such embodiments, it has been found herein that an increase in the polymerizate level of straight chain elastomeric constituents (e.g., polyether diols) within the thermosetting media may also be desirable. Surprisingly, it has been discovered herein that reducing the triglyceride oil (e.g., epoxidized vegetable oil) content and increasing the proportion of straight chain forming thermoset polymerizable reactants, the cured tackiness of the viscoelastic polymer 30 derived from the resulting thermoset viscoelastomeric reaction product will dramatically increase, even though the reaction media may still contain a triglyceride component as a predominant reaction media constituent. In other words, it has been found herein that increasing the compositional adhesiveness and cohesiveness of the thermoset viscoelastomeric reaction product generally can entail decreasing the epoxidized oil content, as well as decreasing the cross-linking triol reactant, resulting in a substantially reduced cross-linkage in the polymeric structure with a concomitant increase in the straight chain producing diol reactant level which increases the intervening straight chain bridging structure within the thermoset viscoelastomeric molecule. It is believed that this polymerizate molecular change (with or without the use of other conventional plastic plasticizers besides the epoxidized triglyceride) creates a localized polymeric polarity charge effectively expressed by the unique oxygen containing viscoelastomeric polyether backbone structure intertwined within the cured thermoset viscoelastomeric reaction product, leading to an effective polarized plasticizer loading, ultimately resulting in outstanding adhesiveness and cohesiveness coupled with desired release properties. Accordingly, an effective cohesive and adhesive efficacy for the viscoelastic polymer 30 may be achieved with a triglyceride content ranging from about 15-percent by weight (15 wt %) to less than about 50-percent by weight (50 wt %) of the total reaction media weight.

As a reaction media constituent, the epoxidized triglycerides, such as those provided by epoxidized vegetable oils, are compositionally effective in providing adhesiveness, cohesiveness and plasticization to the viscoelastic polymer 30. Such epoxidized triglycerides of epoxidized vegetable oils also uniquely contribute towards desired prerequisite viscoelastic properties while further imparting desired cohesive attributes adaptable for use in combination with the lighting apparatus 10 and the elements adhered to the interfacing surfaces (e.g., first surface 30A, second surface 30B, etc.) of the viscoelastic polymer 30 thereof. As may be observed from the aforementioned formulations, the epoxidized vegetable oil may suitably constitute the predominant ingredient of the reaction media, but at a level of less than about 50-percent by weight (50 wt %) of the total weight of the uncured reaction media. In some desirable aspects, the uncured reaction media may initially be formulated so as to possess sufficient flow characteristics to allow the uncured reactants to optionally be pre-formed into a desirable cured shape for use as the viscoelastic polymer 30 herein, such as in the form of a substrate 32. In such aspects, the total plasticizer content will most typically fall within about 25-percent by weight (25 wt %) to about 45-percent by weight (45 wt %) of the total reaction media weight, such as within about 30-percent by weight (30 wt %) to about 40-percent by weight (40 wt %) of the total reaction media weight, to achieve superior adhesiveness and cohesiveness properties.

The epoxidized vegetable oils may effectively serve as a plasticizer in combination with the bridging straight chain polyether diol polymerizate to create the desired cured flexibility, plasticization, releasability, adhesiveness and cohesiveness efficacy for the cured viscoelastic polymer 30. Particularly effective cohesive and adhesive properties arise when the epoxidized vegetable oil concentration range is less than about 50-percent by weight (50 wt %), such as an amount less than about 45-percent (45 wt %) of the total reaction media weight, to provide further enhanced adhesive, cohesive and stability efficacy.

By establishing a viscoelastomeric molecular structure loaded with properly oriented and entrained plasticizers, surprisingly superior adhesive and cohesive properties with stable release attributes are thereby achieved. It is believed that countless enclaves of negatively charged straight and cross-linked diols and triols form a thermoset labyrinth loaded with polarized plasticizer uniformly distributed throughout the curing reaction media and the cured reaction product. It is further believed that this unique polarized polymerizate infrastructure and massive polarized plasticizer stacking within the polymerizate labyrinth creates a synergistic adhesive and cohesive reaction product effect. The thermoset viscoelastomeric reaction products, and the viscoelastic polymers 30 components formed therefrom, possess a surprisingly high tensile strength and softness, indicative that its cohesive thermoset viscoelastomeric structure, coupled with its plasticizer content, significantly contributes towards a superior compositional adhesiveness and cohesiveness. Along with its high tensile strength, the reaction product and the viscoelastic polymer 30 components formed therefrom possess a high degree of elasticity.

In general, the thermosetting reaction media is accordingly formulated with the appropriate level of cross-linkage and straight chain reactants containing a sufficient amount of a plasticizer to create the unique highly adhesive and cohesive viscoelastic polymer 30 of the inventive lighting apparatus 10. A reaction media favoring a substantially lesser cross-linked viscoelastomer loaded with a lesser amount of epoxidized triglyceride plasticizer, such as from epoxidized vegetable oils, have been unexpectedly found to dramatically increase the adhesiveness and cohesiveness of the resulting thermoset viscoelastomeric reaction product. It has been discovered herein that other commonly used plasticizing agents for plastics which are unreactive with the reaction media reactants may also be effectively utilized to impart a high degree of adhesiveness and cohesiveness to the reaction product. In some aspects, such plasticizing agents, in conjunction with epoxidized triglyceride plasticizers, such as those derived from epoxidized vegetable oils (e.g., particularly ESO) may be effectively used to impart enhanced tensile strength and softness to the viscoelastic polymer 30 while also providing a thermosetting reaction media of an exceptional viscosity and workability in the manufacture of the viscoelastic polymer 30.

Indeed, it has been discovered herein that substitution or replacement of the epoxidized triglycerides with polar ester plasticizers (especially those of a substantially lower molecular weight) can actually maintain a desired level of adhesiveness and cohesiveness while still retaining excellent releasability and stability properties. Such suitable polar ester plasticizers of a more fluid consistency at room temperatures (ambient temperature of between about 18° C. and about 24° C., such as about 21° C.) and typically of a relatively low molecular weight will contribute to ideal working viscosities during the initial curing stages, particularly if it is desired to prefabricate the thermoset viscoelastomeric reaction product into a substrate 32. Typically, such more fluid ester plasticizers will have a molecular weight of 500 or less.

In some aspects, such lower molecular weight plasticizers (e.g., particularly the less than 500 MW ester plasticizers) may be effectively used to replace the epoxidized vegetable oil plasticizer (i.e., epoxidized triglycerides). Substitution of the epoxidized triglycerides with ester plasticizers of lower molecular weight will significantly increase fluidity and workability of the thermosetting reactants while still retaining the other desirable thermoset viscoelastomeric reaction product and viscoelastic polymer 30 attributes. Plasticizer (particularly the lower weight esters described above), coupled with a generally balanced diol to triol ratio, can be effectively utilized to provide a thermoset viscoelastomeric reaction product and viscoelastic polymer 30 which will cure and tenaciously bond to an element.

In some desirable aspects, where ester plasticizer is present, the weight ratio of epoxidized triglyceride (e.g., epoxidized vegetable oil) to ester plasticizer can range from about 1:3 to about 3:1, such as between about 1:1 to about 3:1 epoxidized triglyceride to ester plasticizer. The epoxidized triglyceride plasticizer (e.g., epoxidized vegetable oil, such as epoxidized soybean oil (ESO)) can typically comprise a predominant weight portion of the total reaction media, with amounts of epoxidized triglyceride plasticizer ranging from about 20-percent by weight (20 wt %) to less than about 30-percent by weight (30 wt %) of the total reaction media weight being highly effective for certain applications. The molecular size and configuration, polarity, functional molecular groups, etc. of the thermosetting polymeric reactants, along with a combination of lower molecular weight ester plasticizer and epoxidized triglyceride plasticizer in measured amounts can be utilized to effectively contribute towards the creation of a viscoelastic polymer 30 possessing the desired unique adhesiveness and cohesiveness properties of the invention herein. Although the epoxidized triglyceride plasticizer may include a variety of epoxidized vegetable oils (e.g., castor, corn, cottonseed, perilla, safflower, linseed, soybean, tall, etc.), epoxidized soybean oils have been found to be particularly effective as the epoxidized triglyceride plasticizer component for preparing the reaction product and the viscoelastic polymer 30 formed therefrom.

In some preferred embodiments, the viscoelastic polymer 30 can also comprise a catalyst. Illustrative catalysts include the tertiary amines, the tertiary phosphines, strong bases (e.g., alkali and alkaline earth metal hydroxides, alkoxides and phenoxides), the acidic metal salts of strong acids, metal chelates, metal alcholates and phenolates, organic acid salts, organo metallic derivatives, etc. Under the most desirable thermosetting and fabricating conditions, the polymerizate precursors and the plasticizers are provided in the reaction media at room temperature (i.e., ambient temperature of about 18° C. to about 24° C., such as about 21° C.) liquids without necessitating any solvents, other chemical dispersion aids or elevated temperatures to homogeneously disperse the reaction media components.

Since relatively greater exothermic, elevated curing temperatures are more conducive to creating a more rigid thermoset; the reactants and reaction media selection, slower reaction rate catalysts, relatively lower curing temperatures, controlled curing times and triol cross-linking to diol straight chain producing reactants, in combination with an effective plasticizer, are precisely controlled in order to impart the desired viscoelastic polymer 30 characteristics. Carefully controlled reaction media conditions coupled with the proper reactants and plasticizers will accordingly result in a lower degree of cross-linkage and a lower glass transition temperature to yield a more flexible thermoset viscoelastomeric reaction product that is a highly adhesive and cohesive. It is believed that the particular thermoset molecular configuration created by a proper balance between the cross-linkage precursors and the straight chain polymerizates configures the thermoset viscoelastomeric polymerizate to a form that is highly susceptible to effective plasticization with the appropriate polar plasticizer orientation being created within the thermoset viscoelastomeric labyrinth polymerizate structure to yield the desired unexpectedly superior adhesive and cohesive properties. In some desirable aspects, the viscoelastic polymer 30 can be further characterized as being a thermoset viscoelastomeric polymer exhibiting low rebound velocity and hysteresis properties, in addition to unexpectedly superior adhesiveness and cohesiveness. In further aspects, the resulting viscoelastic polymer 30 can characteristically exhibit excellent energy and attenuating properties capable of withstanding repetitive and prolonged shock stress without structural damage or any substantive sag or rebound loss.

Procedurally, the thermoset viscoelastomeric reaction product preparation may illustratively involve thermosetting a reaction media comprising:

a) a carefully measured molar ratio of cross-linking polyols to straight chain producing polyether diols to reduce overall cross-linkages to create a desired bridging thereof with straight chain linkages;

b) an isocyanate prepolymer hardener, such as the aliphatic, aromatic, heterocyclic, etc. polyisocyanates, cycloaliphatic, arylaliphatic, isocyanates;

c) a homogeneous loading with plasticizers, which may include an epoxidized vegetable oil reaction media constituent as a predominant media weight but not as a major media constituent (e.g., epoxidized vegetable oil plasticizer amount of more than about 15-percent by weight (15 wt %), but less than about 50-percent by weight (50 wt %), of the total media weight), as well as other desired plasticizers;

d) a catalytic amount of an appropriate catalyst (e.g., slow acting catalyst), and e) optional ingredients, such as UV stabilizers, pigments, fragrances, etc., as may be desired.

The reaction media contains an appropriate plasticizer loading specifically adapted to provide a curable reaction media, which upon curing, produces a viscoelastomeric reaction product having a unique polymerizate structure effectively loaded with polar oriented plasticizers uniformly or homogeneously distributed throughout its entire mass intertwined and supported by the thermoset polymerizate structure.

The preparation of the superior inventive adhesive and cohesive viscoelastomeric thermoset reaction product and the viscoelastic polymer 30 formed therefrom necessitates controlling the cross-linkage at a level sufficient to retain its thermoset viscoelastomeric polymeric structure. For example, excessive molecular chain cross-linkage caused by the triol and higher polyhydroxyl components, along with the isocyanate thermosetting reactants, results in a viscoelastomeric structure that cannot be effectively loaded with an effective polarized orientation of the plasticizing component, which is functionally essential to impart the superior adhesiveness and cohesiveness to the thermoset viscoelastomeric reaction product. Likewise, if the viscoelastomeric cross-linkage is reduced too much, the polymeric structure is converted into a non-functional viscoelastomer or non-homogenous thermoplastic mass which is molecularly and structurally incapable of retaining any adhesive and cohesive imparting components to a sufficient degree to provide a thermoset viscoelastomer possessing a desired releasable adhesive value, such as at least about 300 $g_f/cm^2$ as measured by the Adhesiveness & Cohesiveness Test. In contrast, a properly balanced negatively charged enclave formed by monitored amounts of triol and diol polymerization precursors in the presence of a heavy load of polar orientable plasticizers effectively oriented within the thermosetting reaction media and the thermoset appears to create a desirable synergistic adhesive and cohesive effect to the reaction product. In some aspects, whether or not the proper viscoelastomeric thermoset polymerizate structure and a sufficient amount of plasticizer have been achieved may be ascertained by determining whether or not the desired adhesion release strength has been achieved, such as a release strength of at least about 300 $g_f/cm^2$ as measured by the Adhesiveness and Cohesiveness Test.

In addition to carefully controlling the amount of cross-linkage in the reaction, the degree of plasticizer loading must also be carefully controlled. For example, excessive plasticizer concentration exceeding the thermoset viscoelastomeric loading capacity will typically lead to unbounded plasticizer visible upon the viscoelastic polymer 30 surface. Conversely, an inappropriate diol to triol reaction media ratio will fail to provide the necessary polymerizate structure needed to achieve a desired adhesion release strength, such as at least about 300 $g_f/cm^2$ as measured by the Adhesiveness and Cohesiveness Test. Typically, a highly functional adhesive thermoset viscoelastic polymer 30 will characteristically possess the uniquely distinctive adhesive and cohesive attributes as mentioned herein. By providing the appropriate cross-linkage sites to polyether straight chain linkage with an appropriate plasticizer loading, adhesion release strengths or separation values at least about 300 $g_f/cm^2$ as measured by the Adhesiveness and Cohesiveness Test, such as at least about 400 $g_f/cm^2$, or at least about 500 $g_f/cm^2$, or greater, may be effectively achieved.

The inventive viscoelastic polymer 30 can releasably adhere to a variety of materials. For example, in general, a cured thermoset viscoelastomeric composition prepared from uncured reactants of a high epoxidized soybean oil content can adhere to adhesively compatible polymeric materials, including but not limited to, polyurethanes and PET (e.g., polyethylene terephthalate), polyolefins (e.g., polyethylene, polypropylene), polyacrylates, etc. In contrast, other halogenated materials, such as halogenated polymers (e.g., polyvinylchloride (PVC)), will not be as adhesively compatible (except for special formulations), but nonetheless provide excellent release properties which render such polymers particularly effective for use as a mold to cure the reactants. However, as illustrated herein and in the Examples, reaction medias designed to tenaciously adhere to normally non-adherent plastics upon curing may be prepared by a properly balanced reaction media.

Since the inventive thermoset viscoelastic polymers 30 characteristically possess a flexible structure, they are readily adaptable for use in combination with elements having a flexible structure, as well as those having a rigid structure. Due to the unique and superior cohesive and adhesive efficacy of the viscoelastomer, the viscoelastic polymer 30 may be provided in any form which provides sufficient support and interfacial surface contact so as to adhere (physically and/or chemically) to a host of element surfaces, including the side surfaces, top surfaces and bottom surfaces of such elements, as well as flexible substrates, while also providing a sufficient interfacial adherence to a variety of elements so as to confine or immobilize any such element placed in contact therewith. The necessary interfacial adherence of the lighting apparatus 10 to an element may be effectuated by providing a viscoelastic polymer 30 of sufficient size to adhere such elements to the lighting apparatus 10.

The present invention may be broadly adapted to a broad range of lighting apparatus 10 and object 60 and/or article 80 combinations 90. For example, one such combination 10 can be designed for stowage of articles 80 within a container object 60. Such articles 80 can range in weight such as from a gram or less, to those weighing about one kilogram or more, wherein any such article 80 may be effectively stabilized and confined at its original stowed (adhered) placement position. Notwithstanding the exceptional adhesive properties of the unique viscoelastic polymer 30 herein, the degree of adhesive immobilization exerted upon any article 80 placed upon the viscoelastic polymer 30 will have a direct correlation to the total contacting surface area between the article 80 and the viscoelastic polymer 30. A greater interfacial surface contact area with the adhered article 80 will generally result in a greater total adhesion of such article 80 to the viscoelastic polymer 30 so as to allow a placement for larger and heavier articles 80 thereupon. Relatively heavier and bulker articles 80 may require thicker viscoelastic polymer 30 substrates 32 than those used to stow lighter articles 80. The adhesive characteristics or strength may vary over a wide range rendering it possible to match a desired degree of adhesiveness to a desired end use. The adhesive and cohesive viscoelastic polymers 30 utilized herein will characteristically possess sufficient viscoelastomeric properties which allow an adhered article 80 to be embedded or cradled by the viscoelastic polymer 30 as opposed to merely compressing without any appreciable article 80 embedding, as is the case for comparative adhesives used in container combinations 90 (such as double-sided adhesive tape, for example). In addition to providing a sufficient degree of cohesiveness and adhesiveness, the viscoelastic polymers 30 used herein can accordingly provide a relatively high degree of adhesive and cohesive stowing stability. This adhesive stability is evident in that the adhesive attraction reaches 90% of its maximum adhesive tack within one (1) minute after an adhered article 80 initial initially contacts the viscoelastic polymer 30.

The inventive lighting apparatus 10 provided herein has been found to possess an unexpectedly high order of adhesiveness so as to attach to an object 60, or restrain an adhered article 80, without dislodgement, even when the lighting apparatus 10 is placed in an inverted position. Surprisingly, such a gravity-defying phenomenon even applies to hefty adhered articles 80 such as a heavy solid stainless steel dinner knife or household scissors, which would normally be expected to be readily dislodged from such an adhesive component when placed in an inverted position. The unique adhesiveness and cohesiveness of the lighting apparatus 10 may be partly attributable to the manner in which the viscoelastic polymer 30 component inherently embeds, encapsulates and adhesively engages an object 60 and/or article 80, coupled with the extremely powerful adhesive attractive influence of the viscoelastic polymer 30 upon the object 60 and/or article 80. For example, conventional elastomers generally compress unilaterally about an impinging article and unilaterally rebound upon decompression so that the resting article tends to primarily rest tangentially upon the conventional elastomer. In complete contrast, an article 80 placed upon the inventive viscoelastic polymer 30 herein causes a displacement of the viscoelastomer while partially submerging into the surrounding viscoelastomeric mass without any substantive volumetric loss to the viscoelastic polymer 30 (as opposed to compression of a conventional rubber elastomeric mass, for example). This creates an embedded cradle for the attached article 80 while also applying an equalized pressure and adhesive attraction upon the article 80. The cradling caused by the inventive viscoelastomeric polymer 30 exerts a uniquely uniform and powerful fluidized embedded and adhesive attractive force upon the embedded article 80. It may accordingly be logically concluded that the viscoelastomeric polymer 30 inherently imparts a significantly greater adhesive attraction when objects 60 and/or articles 80 are adhesively embedded within the viscoelastomeric polymer 30 for attachment.

The initial embedding by forcible placing of the lighting apparatus 10 onto the surface of an object 60, or upon forcible placing of an article 80 onto the viscoelastomeric polymer 30 of the lighting apparatus 10, seems to create an indentation of a significantly greater surface contact area and a fluidized adhesive environment which does not normally occur in a compressive force against a conventional adhesive or conventional elastomeric mass. This initiating contact establishes a deep-seated adhesive and stabilized viscoelastomeric attraction subject to a stabilized increase in adhesion, which in combination with what appears to be a molecular polar alignment within the cured thermoset viscoelastomeric reaction product, exerts an extremely powerful adhesive attractive force upon the object 60 and/or article 80. By physical analogy, it is much easier to entrap an item by an encompassing cupping and fluid-like entrapment under superior attractive adhesive forces than to adhesively entrap and engage an item by tangential contact. It has also been further observed herein that pressure applied upon a combination 90 to more deeply embed the object 60 and/or article 80 within the inventive viscoelastic polymer 30 of the lighting apparatus 10 can cause a concomitant increase in the initial adhesive bonding force between the object 60 and/or article 80 and the viscoelastic polymer 30 by a factor of ten-percent (10%), as opposed to a quiescent placement. However, as aforementioned, the quiescent placement of the lighting apparatus 10 upon an object 60 and/or the quiescent placement of an article 80 upon the lighting apparatus 10 (more particularly the viscoelastic polymer 30 component) will ultimately stabilize to a comparable adhesive separation value (adhesiveness value as measured by the Adhesiveness & Cohesiveness Test) as when pressure has been applied during initial attachment. Evidently, there exists internal forces within the thermoset viscoelastomeric reaction product which creates this delayed increase in adhesiveness.

In some desirable aspects of the invention, the viscoelastic polymer 30 component of the lighting apparatus 10 can exhibit an adhesion release strength of at least about 300 $g_f/cm^2$ as measured by the Adhesiveness and Cohesiveness Test. In other aspects, the lighting apparatus 10 can exhibit about a three-fold (900 $g_f/cm^2$) to about a six fold (1800 $g_f/cm^2$), or more, adhesion release strength, as measured by the Adhesiveness and Cohesiveness Test. In some aspects, combinations 90 possessing the unique releasable adhesion characteristics will, for most uses, typically exhibit an adhesive bonding strength of at least about 300 $g_f/cm^2$ as measured by the Adhesiveness and Cohesiveness Test, such as at least about 400 g/cm², or at least about 500 g/cm², as measured by the Adhesiveness and Cohesiveness Test. In other aspects, combinations 90 will, for most uses, typically exhibit an adhesive bonding strength of less than about 2200 g/cm², such as less than about 1800 g/cm², or less than about 1200 g/cm² as measured by the Adhesiveness and Cohesiveness Test. In still other aspects, combinations 90 will, for most uses, typically exhibit an adhesive release or separation strength ranging from about 300 g/cm² to about 2200 g/cm², such as about 400 g/cm² to about 1800 g/cm², or about 500 g/cm² to about a 1200 g/cm², as measured by the Adhesiveness and Cohesiveness Test. Even though the thermoset viscoelastomeric reaction product from which the viscoelastic polymer 30 component of the lighting apparatus 10 is formed may be tailored too much higher releasable adhesiveness (e.g., greater than 2200 g/cm²), the excessive adhesiveness can render it particularly difficult to release from an object 60 and/or article 80. On a most practical use range, about 500 g/cm² to about 1200 g/cm², such as about 600 g/cm² to about 1000 g/cm², as measured by the Adhesiveness and Cohesiveness Test, can represent a highly effective adhesiveness range. Higher adhesiveness values become more difficult to manually separate and will tend to approach the permanent adhesive range. However, certain applications, such as using the inventive lighting apparatus 10 to securely ground a gaming apparatus to a grounded support (e.g., game play equipment, supportive posts, equipment anchoring, etc.), may make it desirable to utilize a reaction product having an adhesiveness value ranging from about 1500 g/cm² to about 2200 g/cm², or higher, as measured by the Adhesiveness and Cohesiveness Test, without departing from the scope of the invention.

Another observed unique insert feature resides in the manner in which the lighting apparatus 10 will adhesively interact with objects 60 and/or articles 80 adhesively attached thereto. This adhesive interaction is generally characterized by a slight initial increase in adhesiveness within about 5 seconds to about 10 seconds after its initial adhesive attachment to the lighting apparatus 10, which is then followed within 60 seconds by a stabilization to 90% of its maximum or ultimate adhesive attraction. This slight change in adhesiveness may be indicative of an intermolecular realignment, coordinate covalent bonding or polarization of the plasticizing components or other molecular interaction within the viscoelastomeric reaction product structure which forms the viscoelastic polymer 30 component of the lighting apparatus 10 to provide for a delayed increase in adhesive attraction.

The surface area of the viscoelastic polymer 30 component of the lighting apparatus 10 facing an object 60 and/or article 80 must also necessarily possess a releasable surface tack or adhesiveness which allows for an adhesive release from the object 60, or of the article 80 from thereupon, as opposed to a permanent or temporary adhesive bonding between the object 60 and/or article 80 and the viscoelastic polymer 30. For example, commonly stowed articles 80 weighing substantially more than conventional fishing tackle lures, such as carpentry or mechanical tools as commonly stowed in tool boxes, can also benefit from a container combination 90 appropriately fitted with the unique stabilized adhesive and cohesive lighting apparatus 10 which may be specifically tailored-made to meet its intended use (see e.g., FIGS. 7A-7B). The tailoring of the adhesiveness value involves the extent of cross-linking and polyether linkage within the thermoset polymeric structure coupled with the amount and type of plasticizer provided within the thermoset viscoelastomeric reaction product. Moreover, the viscoelastic polymer 30 derived therefrom must also provide a stable adhesive bonding without exhibiting any appreciable adhesive change over prolonged stowage conditions. Surprisingly, the viscoelastic polymer 30 component of the lighting apparatus 10 as provided by this invention retains a substantially unchanged degree of adhesive bonding after stabilization with respect to an object 60 and/or article 80 adhered upon the viscoelastic polymer 30 over prolonged storage periods (e.g., four (4) weeks, or six (6) weeks, or more). There typically exists less than a 10% adhesive change after the initial contact of the object 60 and/or article 80 with the viscoelastic polymer 30.

If desired, the adhesive character of the second surface 30B of the viscoelastic polymer 30 may be physically altered so as to more readily release an adhered article 80 while still maintaining adequate adherence to an object 60. Such surface changes may be implemented by providing a first surface 30A of a greater surface area which adheres to an object 60 as a substantially flat or smooth viscoelastic polymer 30 surface, whereas the second surface 30B may be an irregular surface containing pronounced ridges and valleys designed to substantially reduce its surface contact area with an article 80 and its concomitant cohesiveness. This is generally not needed since the viscoelastic polymer 30 interface area will typically exceed the adhered article's 80 interfacing surface contact area. Since the viscoelastic polymer 30 inherently possesses a powerful cohesiveness and tensile strength, a substantially greater separating force will be required to overcome the adhesive and cohesive bonding of the first surface 30A to the object 60

The most appropriate adhesive strength for any application will depend to a certain degree upon the particular object 60 and/or article 80 to be adhered. The cohesiveness and adhesiveness of the thermoset viscoelastomer reaction product and viscoelastic polymer 30 derived therefrom may be chemically adjusted by plasticizer type and its loading to fit the particular object 60 and/or article 80 to be adhered. Typically the adhesion release strength may be selectively predetermined prior to the thermosetting reaction product preparation so as to match its intended or desired end use. The adhesion release strength may be regulated by the amount and type of plasticizer used and the polymeric configuration of the thermoset viscoelastomer reaction product achieved by the curing of the appropriate reaction media polymerizates. The molecular polymeric structure of the thermoset viscoelastomer reaction product may be modified by the cross-linkage density and straight chain linkage present in the thermoset reaction product so as to enable the polymeric structure to house an effective cohesive and adhesive quantum of plasticizer.

The desired adhesion release strength for any inventive viscoelastic polymer 30 will depend largely upon the type of object 60 and/or article 80 to be adhered thereto. For example, the size, delicacy, configuration and weight of an article 80 will generally establish which releasable adhesive strength value is best suited for any particular end use or combination 90. Fragile articles 80, such as Christmas tree decorations, glass, medication, and the like, will normally require a lesser degree of adhesiveness (e.g., 300-400 g/cm²) which will allow for a less forceful release of the fragile article 80 without damage. Similarly, a heavier article 80 such as a screwdriver may not be adhesively matched by an excessively adhesive insert 30 (e.g., 2000-2200 g/cm²) if the force required to separate the screwdriver 80 from the viscoelastic polymer 30 would make it manually very difficult to separate the screwdriver 80 from an object 60 such as a toolbox or from the viscoelastic polymer 30. This excessive adhesiveness may cause the toolbox 60, as well as the adhesively stowed screwdriver 80, to be lifted together without any screwdriver 80 separation from the viscoelastic polymer 30. However, it should be understood that for certain applications, a viscoelastic polymer 30 having such high degree of adhesive strength may be particularly desirable. For example, pipe wrenches or certain toss games or other grounded devices necessitating a firm grounding of the gaming device would allow for the use of an extremely high adhesive release strength (e.g., 1600-1800 $g_f/cm^2$). Since the thermoset viscoelastomeric reaction product characteristically possesses an extremely high internal cohesiveness which prevents its internal separation (and thus prevents residue separation onto the article 80), the inventive thermoset viscoelastomers herein are uniquely useful for diverse needs requiring a releasable, high tensile strength adhesive which fully retains its structural integrity upon release.

As evident from the aforementioned, the most suitable adhesive strength for the inventive lighting apparatus 10 and its viscoelastic polymer 30 component ultimately depends upon its intended end usage. The adhesiveness, the cohesiveness, the thermoset reaction media attributes, the compositional uniformity, the releasability, the antimicrobial characteristics, and a host of other factors, are attributes which uniquely distinguish the inventive lighting apparatus 10 and the cured viscoelastic polymer 30 from all other adhesives. For most applications, a viscoelastic polymer 30 which is formed from the cured thermoset viscoelastomeric reaction product will normally have an adhesive release strength (i.e., adhesiveness) ranging from at least about 300 $g_f/cm^2$ to less than about 2200 $g_f/cm^2$, such as at least about 400 $g_f/cm^2$ to about 1800 $g_f/cm^2$, or at least about 500 $g_f/cm^2$ to about 1200 $g_f/cm^2$ as measured by the Adhesiveness & Cohesiveness Test. As previously mentioned, substantially higher adhesive strengths may be achieved, but may have a more limited utility.

In some aspects of the invention, the reaction media is cured in its free form, resulting in a layer of thermoplastic viscoelastomeric reaction product, which forms the viscoelastic polymer 30 component of the inventive lighting apparatus 10. Thus, injection molding, extrusion, spraying, vacuum molding, blading, spreading and other conventional thermosetting techniques may be used to apply the uncured reactants to a desired object, and then allowed to cure in its free form. In other aspects, the mixed reaction media can be cast or otherwise prefabricated into a desired form, resulting in a viscoelastic polymer 30 in the form of a substrate 32. Accordingly, the viscoelastic polymer 30 may interface onto any supportive object 60 essentially as a free form layer or as a prefabricated substrate 32, relying upon the powerful cohesive and adhesive characteristics of the viscoelastic polymer 30 to retain its desired shape. Since the adhesiveness and cohesiveness of the viscoelastic polymer 30 serves to self-confine the shape of the viscoelastic polymer 30, it can solely rely upon an open, supportive surface 60A, advantageously eliminating the need for conventional sidewalls or other conventional restraints to maintain its shape. Accordingly, open supportive surfaces 60A such as a flat tray (having no side or top walls) in combination with the viscoelastic polymer 30 uniquely provides a shaped lighting apparatus 10. Thus, in some aspects, the reaction media which forms the inventive viscoelastic polymer 30 can be mixed and prefabricated prior to setting to form a continuous or discontinuous substrate 32 (e.g., sheet, slab, pad, film, coating, etc.) such as by sheathing, molding, filming, slabbing, sheeting, casting, coating or any other prefabrication forming method as may be known by those skilled in the art, and then allowed to set and cure, prior to application to an object 60. However, it should be understood that the viscoelastic polymer 30 of the present invention need not be prefabricated, and thus can be in a free form, without departing from the scope of the invention.

Figure 5:
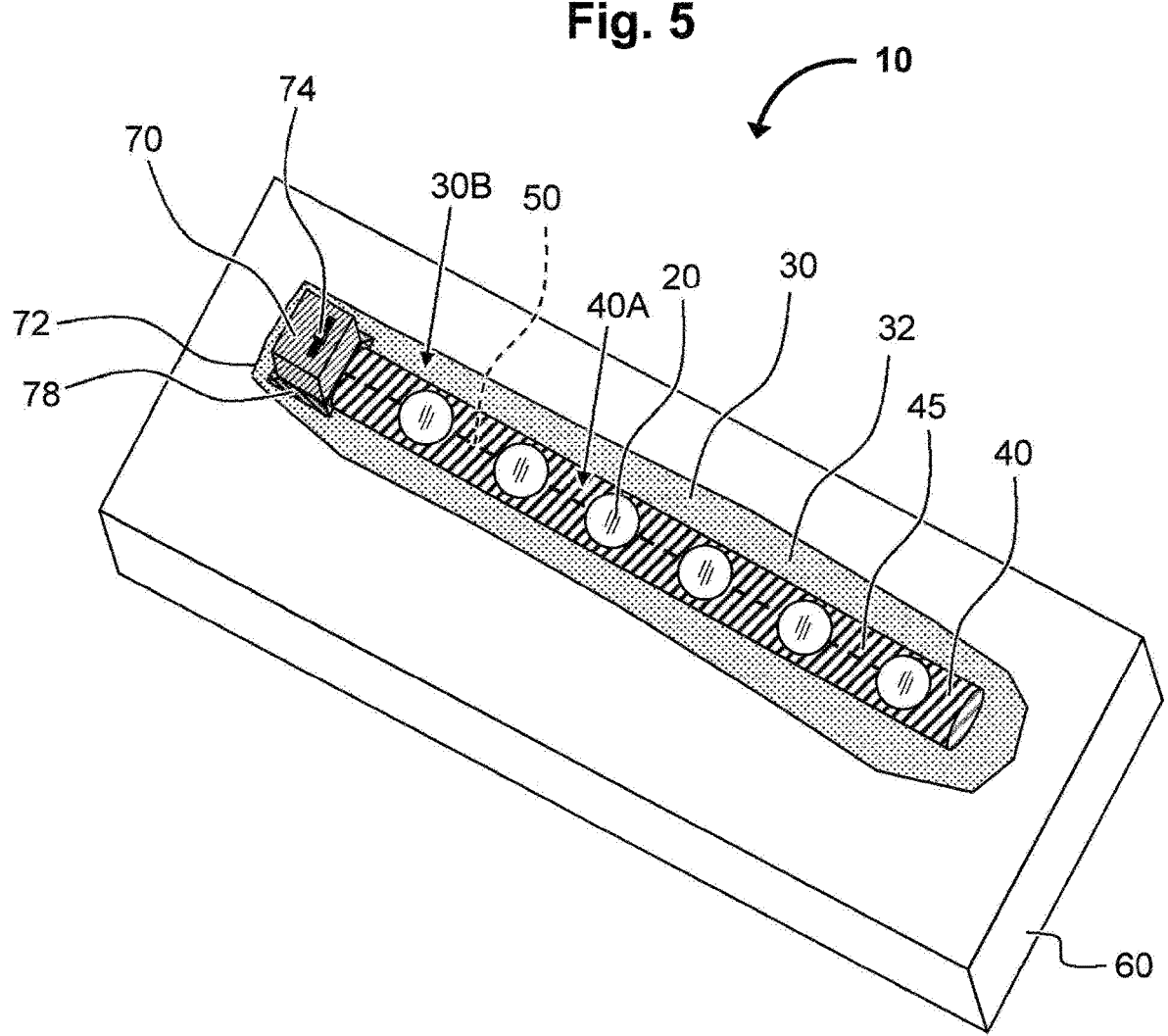
FIG. 5 is a perspective view showing a lighting apparatus of the present invention having a lighting assembly in contact with the second surface of an inventive viscoelastic polymer component, and wherein the first surface of the viscoelastic polymer component is attached to an object.
Figure 6A:
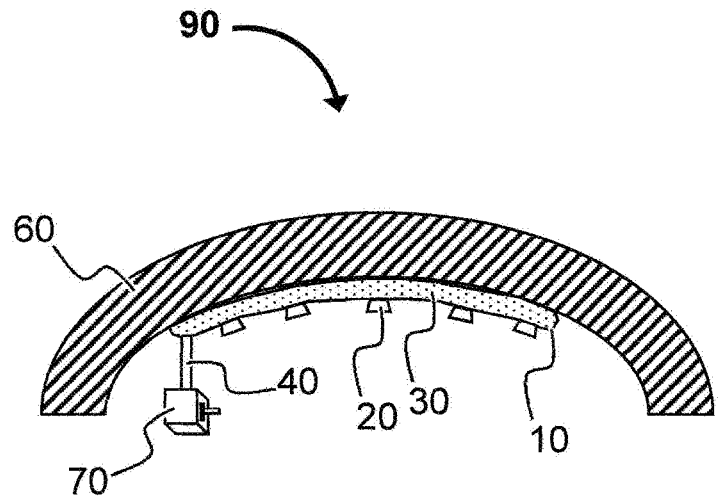
FIG. 6A is a side view showing a lighting apparatus of the present invention adhered to an object.
Figure 6B:
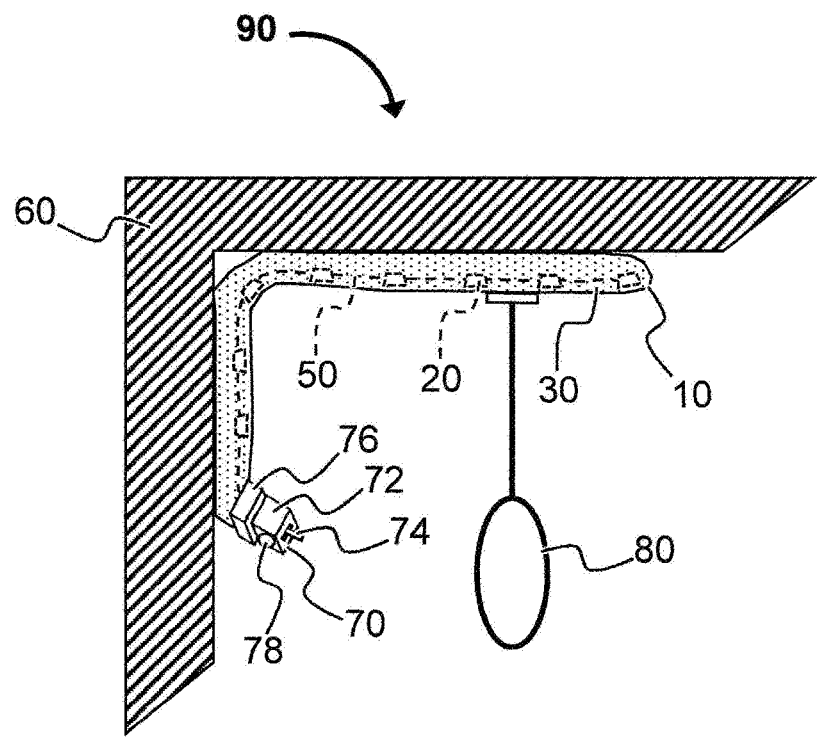
FIG. 6B is a side view showing a lighting apparatus of the present invention adhered to an object, and further having an article adhered to the second surface of the viscoelastic polymer component.
Figure 6C:
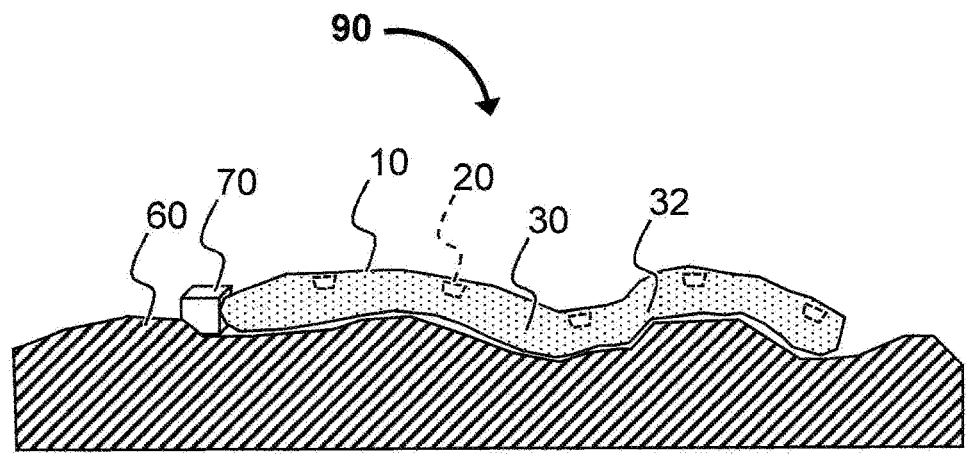
FIG. 6C is a side view showing a lighting apparatus of the present invention wherein the first surface of a viscoelastic polymer component in the form of a substrate is adhered to an object.
Figure 6D:
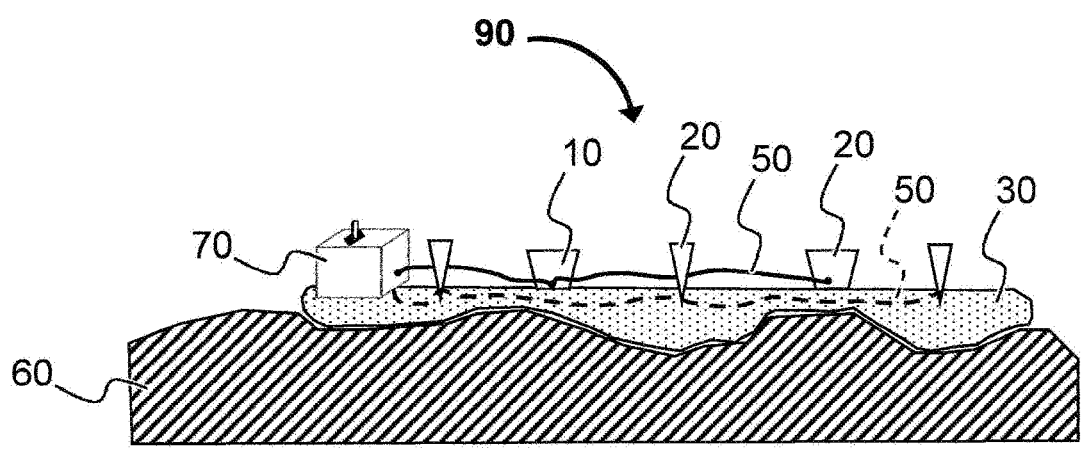
FIG. 6D is a side view showing a lighting apparatus of the present invention adhered to an object.
Figure 6E:
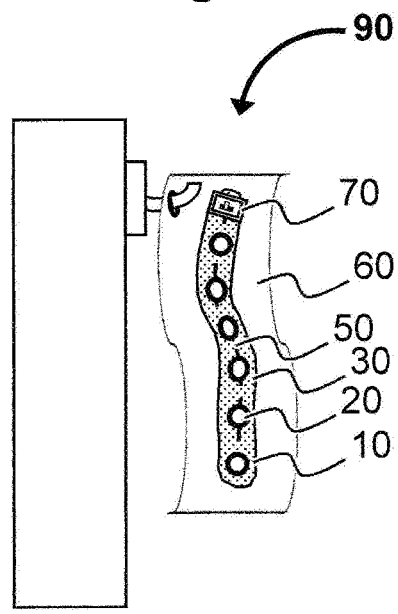
FIG. 6E is a side perspective view showing a lighting apparatus of the present invention adhered to flexible object.
Figure 6F:
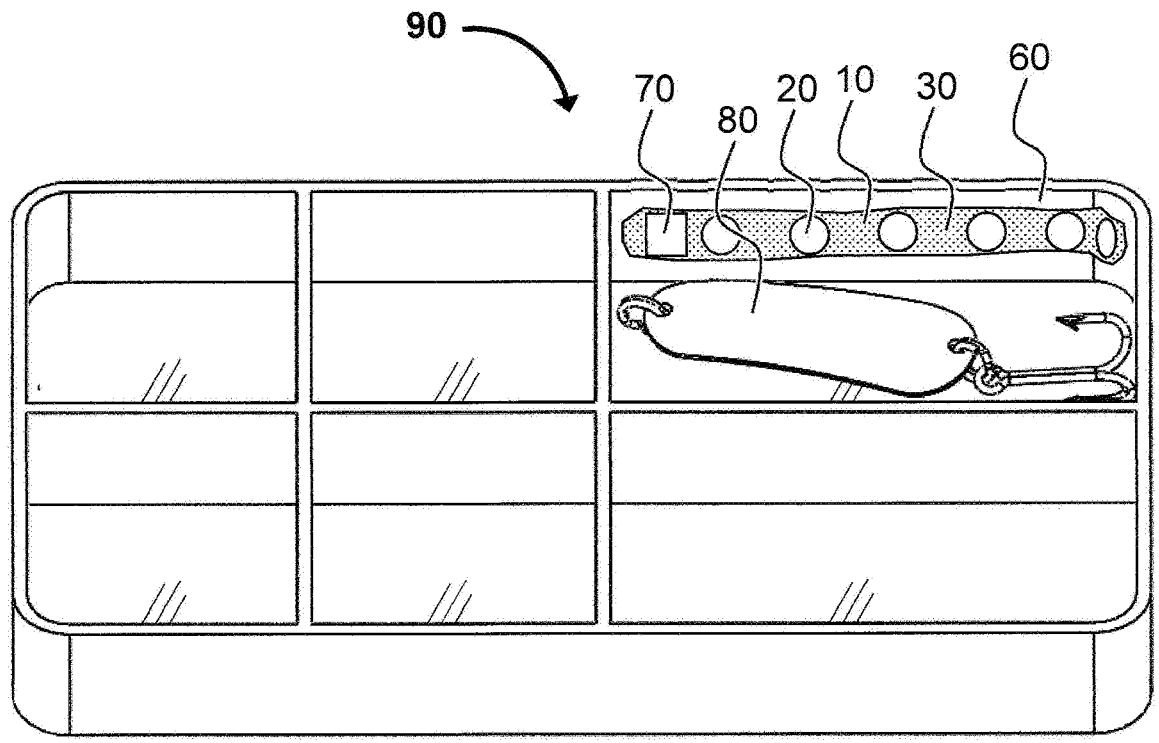
FIG. 6F is a perspective view showing a lighting apparatus of the present invention adhered to the sidewall of an object in the form of a tackle box.
Figure 6G:
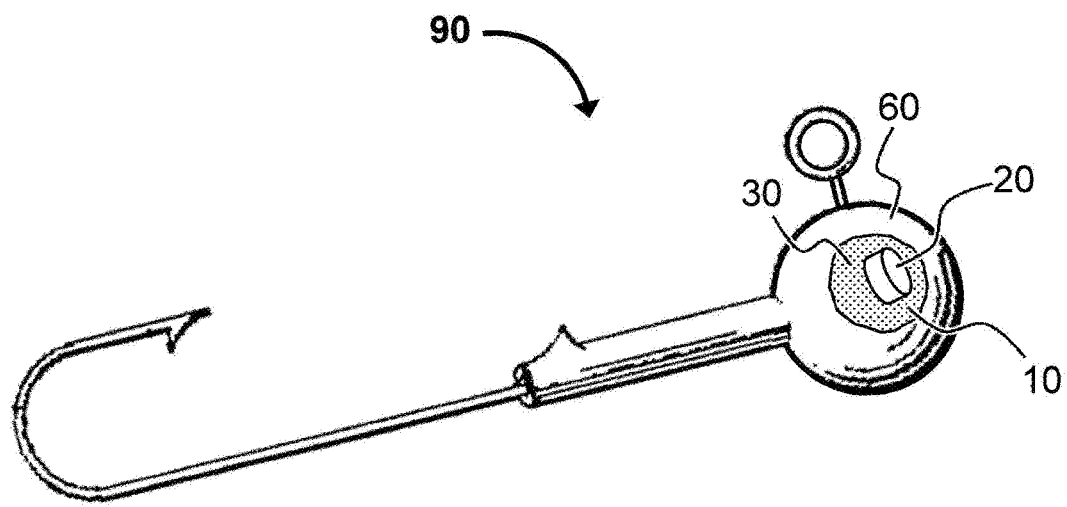
FIG. 6G is a perspective view showing a lighting apparatus of the present invention adhered to an object in the form of a fishing lure.
Figure 6H:
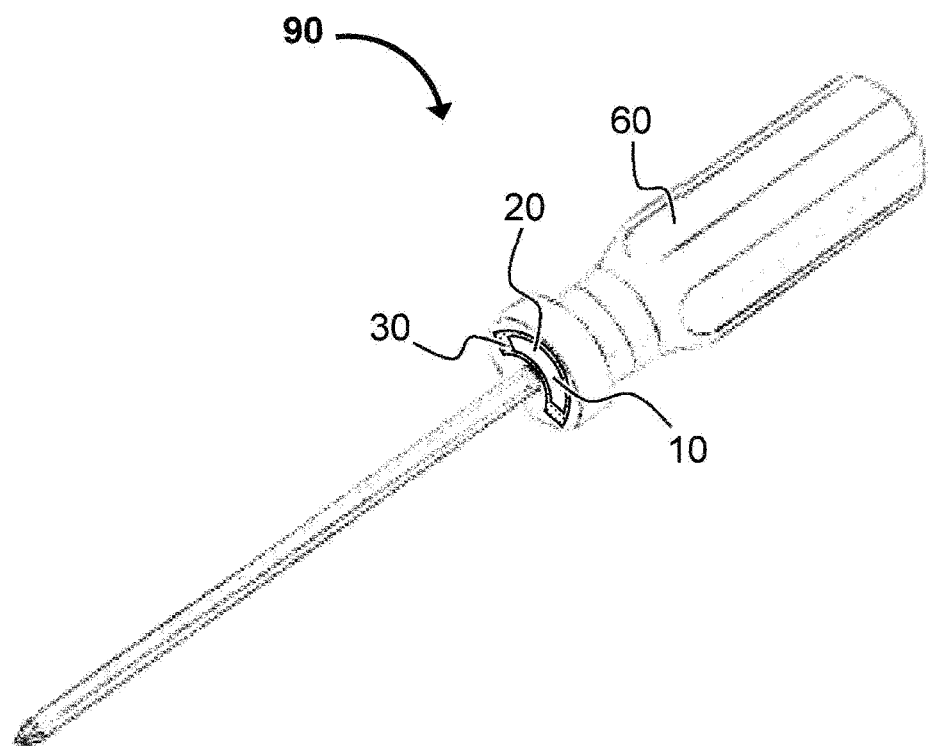
FIG. 6H is a perspective showing a lighting apparatus of the present invention adhered to an object in the form of a screwdriver tool.
Figure 6I:
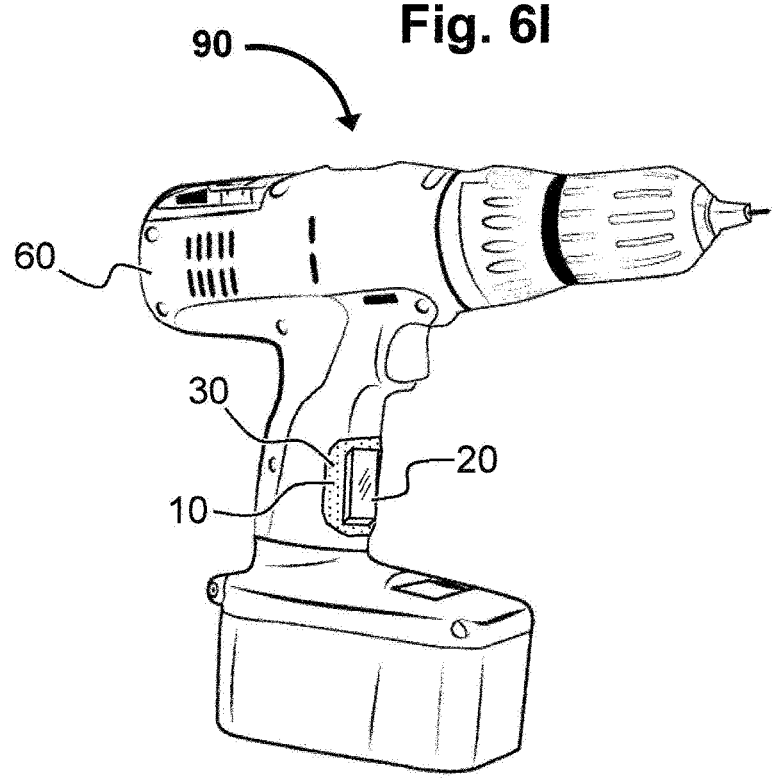
FIG. 6I is a perspective view showing a lighting apparatus of the present invention adhered to an object in the form of a power drill.
Figure 6J:
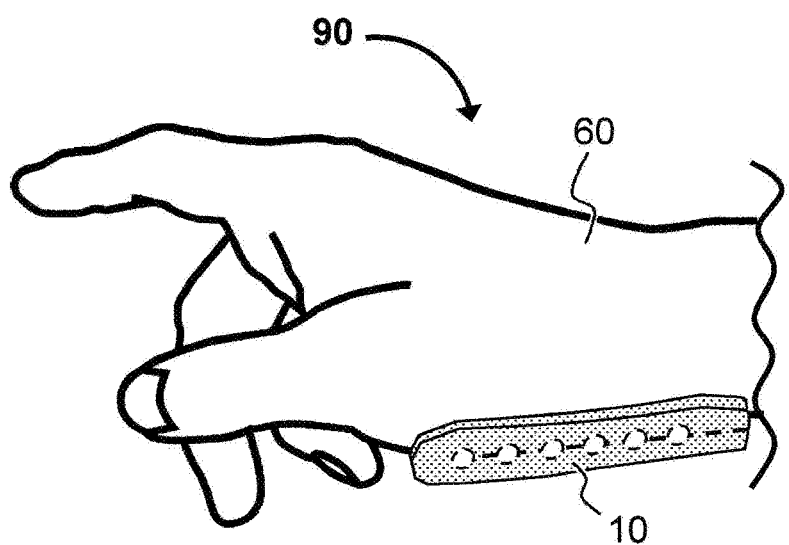
FIG. 6J is a perspective view showing a lighting apparatus of the present invention adhered to an object in the form of skin of a human hand.

As illustrated in FIG. 5, for example, upon curing a prefabricated thermoset viscoelastomeric reaction product to form a viscoelastic polymer 30 in the form of a substrate 32, a light 20 and/or optional electrical connector 50 and/or optional support structure 40 can be affixed to a surface of the substrate 32 (i.e., shown in the illustration as the second surface 30B of the viscoelastic polymer 30), wherein the adhesiveness of the viscoelastic polymer 30 can hold the light 20 and other components disposed thereupon in place, while the adhesiveness of the first surface 30A holds the lighting apparatus 10 in place upon an object 60. Preferably, the viscoelastic polymer 30 substrate 32 will hold the elements disposed thereupon in the initial placement position during use of the lighting apparatus 10, even when inverted 180° from its original orientation.

In prefabricating a substrate 32, uncured thermosetting reactants of the present invention may accordingly be directly deposited (e.g., sprayed, injected, molded, casted, etc.) onto any suitable flexible or solid (i.e., rigid) supportive base and allowed to cure into the desired viscoelastic polymer 30. Thus, the uncured thermosetting reactants may be applied and cured as coatings, strips, systematic castings (e.g., circles, spirals, etc.) or in any other fabricating form sufficient to create a viscoelastic polymer 30 substrate 32 of a sufficient size to hold or immobilize the other components of the lighting apparatus 10 to be placed thereupon. Injection molding, extrusion, spraying, vacuum molding, blading, spreading calendering, sheeting and other conventional thermosetting prefabricating techniques may be used to apply the mixed but uncured reactants in the manufacture of prefabricated substrates 32 adaptable for use as a removable viscoelastic polymer 30. The curing rate and flow characteristics (i.e., viscosity) of the mixed, uncured reactants can be effectively controlled by the type and amount of catalytic agents, reactants, thermal conditions, plasticizers, etc. used in conducting the thermosetting reaction. Excellent viscosity control during the initial mixed, uncured prefabrication stages may be achieved, for example, by increasing the level of lower molecular weight plasticizers and a decrease of higher molecular weight plasticizer (e.g., epoxidized soybean oil (ESO)) concentration.

The manufacture of the viscoelastic polymer 30 in a substrate 32 form may be prepared by initially depositing the uncured thermosetting elastomeric reactants in a suitable reaction media and prefabricating form (e.g., compartmentalized sized sections, or sheeted, etc.), such as by casting, injection molding, calendering, and the like, or by simply depositing measured amounts of the mixed, uncured flowable reactants upon a moving chemically inert belt (equipped with or without heating) etc. and thereafter allowing the uncured reactants to set and cure under manufacturing conditions adapted to form the viscoelastic polymer 30 of a desired thickness and form. Upon setting and curing in a desired calendered, strip, sheet, casted, etc. form, the cured thermoset viscoelastomeric reaction product may suitably be cut or sized to an appropriate configuration to match its desired shape. Viscoelastic polymer 30 components of a desired configuration and thickness may also be prepared by conventional molding techniques (e.g., injection molding). For certain applications, the appropriate mixed, uncured, flowable reactant dosage as needed to provide the desired viscoelastic polymer 30 component configuration and coating thickness may be directly applied to an object 60 which then upon subsequent curing and application of the other components of the lighting apparatus 10 creates a desired stabilized combination 90. In the uncured thermosetting form, the thermoset reaction media can be formulated (e.g., epoxidized soybean oil to ester plasticizer levels) so as to provide the desired flow or viscosity characteristics so as to permit the casting, molding, etc. of an interfacing viscoelastic polymer 30 of a desired configuration and thickness.

In some aspects, it may be desirable to obtain a more permanent bond to an object 60 and/or to a component of the lighting apparatus 10, which may include a light 20, an optional electrical connector 50, and/or an optional support structure 40, etc., for example. In one exemplary aspect, a plurality of lights 20 connected via an electrical connector 50 can be placed onto an object 60, and mixed, uncured reaction media can be poured onto the lighting apparatus 10 components and object 60, at a thickness substantially covering the lights 20 and electrical connector 50, etc. The combination can then be cured in situ to form a lighting apparatus comprising a viscoelastic polymer 30 component having a first surface 30A and a second surface 30B, wherein the first surface 30A is essentially permanently bonded to the object 60, wherein the lights 20 and electrical connector 50 are disposed within the viscoelastic polymer 30, and wherein the second surface 30A has a releasable adhesiveness between about 300 $g_f/cm^2$ and about 1800 $g_f/cm^2$, as measured by the Adhesiveness & Cohesiveness Test. In such aspects, the thermoset viscoelastomeric reaction product may be suitably manufactured under unique thermosetting reaction media conditions in which the necessary thermosetting precursors of polymerizable reactants are immersed in a lipophilic plasticizing media, which upon curing, provides the desired thermoset viscoelastomeric reaction product, which is especially suited for use as the viscoelastic polymer 30 component of the lighting apparatus 10 herein. In procedures which involve a reaction media thermoset bonding of an object 60 and/or a component of the lighting apparatus 10 to the viscoelastic polymer 30, the thermosetting reactants in a mixed, uncured form may be applied by spray coating, injection molding, casting, pouring, and the like, and/or combinations thereof, at a desired thickness to the desired element, and then allowing the combination to cure in situ to provide an object 60 and/or a component of the lighting apparatus 10 that is at least partially coated by the thermoset viscoelastomeric reaction product, which then may become essentially permanently bonded to the cured viscoelastic polymer 30 formed therefrom. The amount of plasticizer and the level of cross-linking precursors in the reaction media can change the cured bonding characteristics, and thus can be utilized to control the permanency (i.e., degree of adhesion) of the bond. This technology may be applied to a wide variety of materials (e.g., metallic materials, and non-metal metallic materials such as wood, cloth, plaster, latex and other paints, thermosets, thermoplastics, and the like). By applying the uncured reactants to a material, the uncured thermoset viscoelastomeric reaction product, when cured, forms a viscoelastic polymer 30 that is more firmly bonded to the material, and thus may be used to provide a more permanently bonded coating (i.e., compared to the adhesion of a material placed in contact with the viscoelastic polymer 30 after it has been cured). In some aspects, conventional flaming techniques to prepare a material's surface for coating may be applied to further improve the bonding.

By providing the proper thermosetting polymerizable precursors in the appropriate amounts, the basic thermoset viscoelastomeric chain provides a basic molecular structure especially adaptable for in situ loading with plasticizer which, depending upon type, can be used to beneficially alter the adhesive and cohesive characteristics of the cured viscoelastomer. For example, an effective amount of long chain polyether polymeric linkages coupled with the appropriate isocyanate and triol cross-linkages can provide a polymeric chain of a desired polarity having an unexpectedly high affinity for a loading of polar plasticizing components within the thermoset viscoelastomeric reaction product infrastructure. The selection of the particular plasticizing agent and its concentration can have a pronounced effect upon the adhesiveness and cohesiveness of the thermoset viscoelastomeric reaction product. This may be exemplified by the loading of the viscoelastomeric reaction product with ester plasticizing agents which are typically made by reacting an alcohol with a fatty acid. Suitable ester plasticizers include the ester condensation product of an alcohol (C1-C18) with a polycarboxylic acid(s) which esters can be used to an advantage in preparing a thermosetting reaction media and thermoset viscoelastomeric reaction product having an adhesiveness tailor-made for a particular end use. For example, certain applications will require a tenacious adhesiveness whereas other applications are best matched with milder releasable adhesive characteristics, such as for fragile items, for example. Similarly, the type of plasticizer (e.g., dibutyl sebacate) may be used to advantage in preparing an uncured reaction media having an exceptionally low initial viscosity, rendering the uncured reaction media especially suitable for reaction product prefabrication into a substrate 32. The polar strength (often referred to as "dipole moment") of these plasticizing esters depends to a certain degree upon the alcohol condensation reactant chain length which also has an effect upon the adhesive characteristic of the thermoset viscoelastomeric reaction product.

As typical with most thermosetting resins, it cannot be precisely ascertained what phenomena actually occurs when an uncured viscoelastomeric reaction media is cured and rigidly bound to a compatible material. Whether the thermosetting creates a chemical bonding or an extremely strong molecular or mechanical bonding is unclear. Nonetheless, it has been discovered that an increase in the diol to triol weight ratio coupled with a reduced plasticizer content will result in a highly tenacious cured bonding of the viscoelastomeric reaction product to a compatible material, as well as to those materials recognized as being resistant to bonding. In certain applications, a peelable or more readily releasable cured coating may be desired, whereas in others, a more tenacious bonding may be better suited to its end use. Although the curing of the reaction media having reduced cross-linking triols and plasticizers content affects the bonding characteristics of a surface of the resulting viscoelastic polymer 30 cured in situ to a material, the remaining surface area (i.e., unbounded surface) of the cured viscoelastic polymer 30 still retains all of its desired adhesive and cohesive characteristics upon curing. In addition, it has been discovered herein that the reduced triol and plasticizer content also increases the tensile strength of the viscoelastic polymer 30, while providing a more permanent bonding to the material upon which it was cured in situ.

Although the providing of the viscoelastic polymer 30 as an adhesively attachable and removable substrate 32 may be desirable for ease of cleaning, the uncured viscoelastomeric reactants, when cured in situ upon an object 60 and/or a component of the lighting apparatus 10 will create a tenacious and essentially permanent (and possibly a chemical) bonding therebetween. For lighting apparatus 10 variations, the thermoset bonded form (i.e., curing onto an object 60 and/or a component of the lighting apparatus 10) may be more desirable than a removable form. Such permanent bonding of the thermoset viscoelastomeric reaction product provides a lighting apparatus 10 which may nonetheless be readily cleansed by washing the entire combination (lighting apparatus 10 components and/or objects 60), with the viscoelastic polymer 30 being permanently bonded or thermosetting bonded thereto without any concern over viscoelastic polymer 30 disintegration. For other applications wherein the viscoelastic polymer 30 affords a sufficient flat open surface area to permit the lighting apparatus 10 to easily be washed and cleansed from air borne and other contaminants, the thermoset bonding of the viscoelastic polymer 30 to an object 60 and/or to a component of the lighting apparatus 10 may be desirable. In addition, it has been discovered herein that compositionally, the viscoelastic polymer 30 can also provide antimicrobial protection. Thus, the lighting apparatus 10 becomes particularly useful should microbial contamination become a major concern for a particular use (e.g., in relation to food, pharmaceuticals, etc.). Since the antimicrobial component exists throughout the entire viscoelastic polymer 30, it will not be removed by washing.

The lighting apparatus 10 may be appropriately tailored so as to adhesively fit a particular object 60. Thus, there are no specific limits to the size dimensions of any particular lighting apparatus 10 (see e.g., FIGS. 6A-7C for various non-limiting dimensional examples). There exist special benefits for certain combinations 90 of a lighting apparatus 10 and an object 60 provided by the removable viscoelastic polymer 30 component. This will permit a removal of the lighting apparatus 10 from the object 60 for cleaning, repositioning, etc. This constitutes a major advantage over conventional lighting apparatus.

Similarly, neither the lighting apparatus 10 not its viscoelastic polymer 30 component have any specific limits as to thickness. Typically, the thickness of the viscoelastic polymer 30 component will range between about 3 mm and about 65 cm, such as between about 4 mm and 20 cm, for example. However, it should be understood that the thickness of the viscoelastic polymer 30 component can be less than 3 mm and greater than 65 cm without departing from the scope of the invention. For example, where the viscoelastic polymer 30 component is formed in situ upon an object 60 in a coated and thermoset bonded form, a substantially lesser amount of the viscoelastic polymer 30 may be typically utilized for certain applications to provide the desired cohesiveness and adhesiveness. Typically, such an in situ viscoelastic polymer 30 component in a tightly bonded form or unbounded form will be less than about 60 mil (1.5 mm) in thickness, such as in a range of about 20 mil to about 50 mil (0.5 mm-1.3 mm). Thicker sizes may be used but may be deemed unnecessary, depending on the application. Notwithstanding, the viscoelastic polymer 30 component will generally be sized to accommodate the other components of the lighting apparatus 10, as well as the object 60 and/or any articles 80 which are desired to be attached thereto.

As illustrated in FIG. 1B, in some aspects, a light 20 and/or optional electrical connector 50, etc. can be disposed upon a second surface 30B of the viscoelastic polymer 30 and sufficiently attached thereto by virtue of the unique adhesion properties of the viscoelastic polymer 30 itself (i.e., without additional attachment means), if desired. As illustrated in FIG. 1C, in other aspects, prior to fully curing, a light 20 and/or optional electrical connector 50 can be at least partially submerged into a quantity of the inventive reaction media upon mixing, and then subsequently cured such that the resulting viscoelastic polymer 30 partially encapsulates the light 20 and/or electrical connector 50 and/or optional support structure 40, etc. The same can be achieved by at least partially submerging the light 20 and/or electrical connector 50 and/or optional support structure 40, etc., into the reaction media during the curing process (prior to fully curing), provided the thermoset resin is still in a gelatinous state (i.e., has not fully cured).

As illustrated in FIG. 1D, in still other aspects, upon mixing the reaction media, a light 20 and/or optional electrical connector 50 and/or optional support structure 40, etc., can be fully submerged into a quantity of the inventive thermoset resin and then subsequently fully cured such that the resulting viscoelastic polymer 30 completely encapsulates the light 20 and/or electrical connector 50 and/or optional support structure 40, etc. The same can be achieved by fully submerging the light 20 and/or electrical connector 50 and/or optional support structure 40, etc., into the thermoset resin during the curing process, provided the thermoset resin is still in a gelatinous state (i.e., has not fully cured).

Referring again to FIGS. 6A-7C, the viscoelastic polymer 30 component of the lighting apparatus 10 has a broad range of adhesive affinity to most materials which can form an object 60, as well as most articles 80 which may be adhered thereto, which broadly embraces a wide range of diverse materials. Accordingly, the viscoelastic polymer 30 component may be used to physically adhere, or chemically bond, to a host of objects 60 and articles 80. Such suitable materials include, but are not limited to, cellulosic materials (e.g., wood, wood composites, vegetative materials, nonwoven substrates, paperboard, cardboard, etc.), thermosets, thermoplastics, plastic composites, metals (e.g., aluminum, steel, tin, metal alloys, etc.) textiles, glass and a host of other adhesive compatible rigid supportive materials, as well as flexible supportive materials. For example, with particular reference to FIG. 6E, in addition to rigid objects 60, the viscoelastic polymer 30 component is also compatible with flexible objects 60, such as towels, clothing, textile curtains, rubber mats, plastic shower curtains, plastic wrap, metallic foil, paper, paperboard, cardboard, and the like. Flexible objects 60 such as flexible medical equipment containers, first responder tote bags, flexible photographic equipment bags, tool pouches, fishing tackle bags and a host of other flexible construction objects may benefit from the unique attributes afforded by this invention. Similarly, flexible articles 80 such as bandages, clothing, towels, hoses, photographs, paper sheets, notecards, business cards, rubber bands, erasers, fishing flies, fishing leaders, and a host of other flexible construction articles may benefit from the unique attributes afforded by the invention. Accordingly, the lighting apparatus 10 broadly applies to any material adhesively compatible with the inventive viscoelastic polymer 30 component (i.e., the viscoelastic polymer 30 adhesively bonds or chemically bonds to any adhesive compatible material from which an object 60 and/or article 80 may be comprised). However, certain of the halogen containing polymers (e.g., PVC) for certain formulations may be adhesively incompatible to the adhesive properties of the viscoelastic polymer 30 herein. This may be due to the electronegativity of the PVC and the thermoset viscoelastomeric reaction product which forms the viscoelastic polymer 30, causing a repelling of like charges. Such non-adhesive PVC materials may, however, be effectively used as continuous and non-reactive manufacturing belts for use in the curing and prefabricating of molded, sheeted, filmed, casted, etc. viscoelastic polymer 30 components.

The lighting apparatus 10 of the present disclosure differ from conventional lighting apparatus in that, inter alia, it comprises the inventive viscoelastic polymer 30 component. Compositionally, the viscoelastic polymers 30 as used herein differ from conventional adhesive members in order to satisfactorily adhere to the other components of the lighting apparatus 10, as well as to objects 60 and/or articles 80. Unlike such conventional adhesive members, the inventive viscoelastic polymers 30 as used herein possess powerful cohesiveness throughout their entire compositional structure so as to retain structural integrity upon separation from an adhered article 80 while also tenaciously adhering until released to most objects 60 comprising common metals, thermosets, thermoplastics, celluloses, textiles, and the like (both solid (i.e., rigid) or flexible). The cohesive molecular components of the viscoelastic polymer 30 are tenaciously and inherently bound throughout its entire compositional make-up, rendering it virtually impossible to leave any compositional residue when the polymer 30 is separated from an object 60 or upon removal of an article 80 from the polymer 30 component. Since the highly adhesive viscoelastic polymer 30 components (as provided herein) possess unusually high adhesive bonding efficacy comparative to any commonly known and available adhesive materials, they may be effectively used in configurations that are horizontal, vertical, inverted, and combinations thereof, including adherence to both rigid and flexible materials.

Referring now to FIGS. 6A-6J, in addition to the numerous advantages already enumerated herein, the inventive lighting apparatus 10 of the present disclosure offers yet additional significant advantages over conventional lighting apparatus. For example, the inventive lighting apparatus 10 comprises a first surface 30A capable of self-adhering to the surface of an object 60. This eliminates the need for an additional external fastener (mechanical fastener, glue, adhesive tape, etc.) and further prevents potential damage to the object 60. In addition, the lighting apparatus 10 is flexible, such that it can substantially conform to the shape of the object 60, thus maximizing the surface area for improved adhesiveness, while presenting a clean (uncluttered) look to the human eye. Furthermore, the lighting apparatus 10 is releasable such that it can be re-aligned, or even re-positioned, as desired. Moreover, the adhesiveness of the lighting apparatus 10 remains substantially constant from its initial adhesion to an object 60, such that it can be removed from an object 60 and reapplied to it (or to another object 60) repeatedly without substantial loss of the its adhesive properties. In addition, the lighting apparatus 10 exhibits a high cohesiveness, such that removal of the lighting apparatus 10 from an object 60 leaves the surface of the object 60 clean and essentially residue-free while the viscoelastic polymer 30 component substantially retains its initial shape. Indeed, the adhesive nature of the first surface 30A can actually remove debris from the surface of an object 60, thus providing an object's surface that is potentially cleaner upon removal of the lighting apparatus 10, than it was prior to application of the lighting apparatus 10 to the object 60. Accordingly, the lighting apparatus 10 can also be utilized as a lighted cleaning tool.

Other advantages relate to the position of the viscoelastic polymer 30 component with respect to the other lighting apparatus 10 components (i.e., lights 20, optional electrical connectors 50, optional support structures 40, etc.). In one example, the other lighting apparatus 10 components can first be positioned upon an object 60, and then subsequently covered with the first side 30A of the viscoelastic polymer 30, such as when the viscoelastic polymer 30 is in the form of a translucent substrate 32. In another example, the other lighting apparatus 10 components and the viscoelastic polymer 30 can be formed in situ on an object 60 (i.e., the other lighting apparatus 10 components can first be positioned upon an object 60, and then coated with mixed, liquid reaction media which is subsequently cured to form the viscoelastic polymer 30) such that the other lighting apparatus 10 components are disposed at least partially, or entirely, within the viscoelastic polymer 30 component. In both cases, the other lighting apparatus 10 components are protected against impacts or other potential damage, while also providing a clean (unobstructed) second surface 30B of the viscoelastic polymer 30 to maximize adhesiveness for an article 80 to be adhered thereto.

Further advantages of the inventive lighting apparatus 10 relate to its viscoelastic polymer 30 component. For example, the utilization of the thermoset viscoelastomeric polymer 30 provides a unique adhesive and cohesive environment creating strong adhesive and cohesive forces which lead to unexpectedly superior advantages of the thermoset viscoelastomeric polymer 30 over any other known adhesive substrates. For example, conventional double-sided adhesive tape (such as SCOTCH Permanent Double Sided Tape, available from 3M Company, having a place of business located in St. Paul, Minn., U.S.A.) merely achieves, at best, tangential contact with an object 60 or article 80, adhesively attaching to surfaces of such objects 60 or articles 80 via glue applied to its own substrate surface. Upon removal of such tape, a residue of the glue typically remains upon the surface of the object 60 or article 80. In addition, such tape has no capability of dispositioning lighting apparatus 10 components (e.g., lights 20, optional electrical connectors 50, optional support structures 40, etc.) within the interior of its substrate structure, nor does it exhibit impact insulating/shock absorbing properties, and therefore essentially provides no protection of such lighting apparatus 10 components. Furthermore, such tape is not generally re-usable, and would provide a significantly reduced adhesiveness upon an attempted re-use as compared to its initial adhesiveness (in part because the tape substrate would comprise less glue than in its initial state). Moreover, such tape cannot be cleansed of airborne and/or other contaminants which will potentially accumulate upon the tape. In addition, such tape does not exhibit antimicrobial characteristics, and is therefore not ideal for uses in which antimicrobial characteristics are desired (such as in relation to food, pharmaceuticals, clean environment labs, etc.). In contrast, when the inventive viscoelastic polymer 30 is placed upon an object 60, or when an article 80 is placed upon the inventive viscoelastic polymer 30, with a suitable amount of applied placement pressure to adhesively engage the viscoelastic polymer 30, there will arise a concomitant counteraction of a fluidized flow by the viscoelastic polymer 30 which in effect embeds the object 60 and/or article 80 within an adhesive cavity (i.e., slightly surrounds it), thus creating a substantially greater contacting interface and adhesive attraction area than would normally arise by the simple tangential surface contact of a conventional adhesive substrate, such as permanent double-sided adhesive tape. It has also been observed that the adhesive attractive forces of the viscoelastic polymer 30 can actually increase slightly after initial contact with an object 60 and/or article 80, and then stabilize. This same phenomena even applies when an object 60 or article 80 is quiescently placed in contact with the viscoelastic polymer 30, which placement may have a lesser initial adhesion release strength, but with time will ultimately become stabilized to a comparable adhesive value as with an object 60 and/or article 80 for which suitable engaging pressure was initially applied. In addition, upon removal of the lighting apparatus 10 from an object 60, or removal of an article 80 from the lighting apparatus 10, no residue of the viscoelastic polymer 30 remains upon the surface of the object 60 or article 80 due to its unique and superior cohesiveness. In addition, lighting apparatus 10 components (e.g., lights 20, electrical connectors 50, support structures 40, etc.) are capable of being partially or completely disposed within the interior of the viscoelastic polymer 30 component, which provides enhanced protection of the other lighting apparatus 10 components (e.g., lights 20, electrical connectors 50, support structures 40, etc.) while freeing-up the a surface of the viscoelastic polymer 30 for other uses (e.g., attachment of an article 80). Moreover, the inventive viscoelastic polymer 30 exhibits enhanced impact insulating/shock absorbing properties which provide further protection to the other lighting apparatus 10 components. Furthermore, upon removal of the lighting apparatus 10 from an object 60 and/or removal of an article 80 from the lighting apparatus 10, the lighting apparatus 10 is fully re-usable, typically providing adhesion characteristics equal to those exhibited during initial attachment, even after multiple removals and subsequent re-attachments. Moreover, the lighting apparatus 10 (particularly the viscoelastic polymer 30 component) can be cleansed of airborne and/or other contaminants which may accumulate upon the viscoelastic polymer 30, which thus restores its adhesive properties to a degree substantially equal to those when the lighting apparatus 10 was first adhered. In addition, the lighting apparatus 10 (more particularly the viscoelastic polymer 30) exhibits antimicrobial characteristics, making it ideal for uses in which antimicrobial characteristics are desired (such as in relation to food, pharmaceuticals, clean environment labs, etc.). Accordingly, the unique and atypical adhesive environment as provided by the viscoelastomeric polymer 30 herein, coupled with its superior adhesive and cohesive efficacy, creates an object 60 and/or article 80 combination 90 possessing unheralded releasable adhesion and cohesive characteristics which were heretofore deemed unfeasible. Such an unheralded adhesive advance allows for an uncanny use of the lighting apparatus 10 in horizontal, vertical and/or inverted positions (see e.g., FIGS. 6A-6I).

Another advantage of the inventive lighting apparatus 10 relates to the visual properties of its viscoelastic polymer 30. More particularly, the viscoelastic polymer 30 can be formulated to be translucent and/or transparent. Accordingly, as desired, the uncured viscoelastic polymer 30 reactants may be formulated so as to provide a translucent and/or transparent viscoelastic polymer 30 which permits the lights 20 to shine through the polymer 30 (i.e., clearly visible through the polymer 30), or alternatively, permits the polymer 30 itself to glow. Coloring additives such as pigments, dyes, and the like, may also be formulated into the uncured reaction media to provide a desired coloring effect. The viscoelastic polymer 30 may similarly be color coded according to certain criteria (location, type of use, type of lighting 20, type of switch 70, type of article 80 adhered thereto, etc.). Similarly, fragrances may also be formulated into the uncured reactants to provide a scented lighting apparatus 10.

As mentioned above, yet another advantage is that the inventive lighting apparatus 10 (particularly its viscoelastic polymer 30 component) is washable, allowing for removal of accumulated airborne contaminants, or other contaminants, therefrom. More particularly, since the cohesive and adhesive viscoelastic polymer 30 securely adheres to a host of objects 60 and/or articles 80 which come into direct contact therewith, the thermoset viscoelastomeric cohesive polymer 30 likewise is susceptible to potential accumulation dust, dirt, linen, and other contaminates coming in contact with its exposed surface. Excessive accumulations of such contaminants can dramatically reduce the adhesive efficacy of the exposed exterior surfaces of the viscoelastic polymer 30 to the extent it no longer possesses a desired capacity to effectively adhere to objects 60 and/or articles 80 placed upon its interfacing surface. By providing the viscoelastic polymer 30 in a removable and washable form (e.g., a layer or a substrate), any such foreign clogging matter adhering to its surface(s) may accordingly be readily removed via a solution of common dish soap and water. Consequently, the adhesiveness of the viscoelastic polymer 30 is then restored to substantially its original efficacy. For example, the viscoelastic polymer 30 may be provided in a consumer friendly substrate 32 form which allows a user to remove other lighting apparatus 10 components from the viscoelastic polymer 30 substrate 32, as well as any articles 80 which may be adhered thereto, and to subsequently remove the substrate 32 from an object 60. The substrate 32 can then be washed in a sink with a solution of dish soap and water, or even placed in a current style dishwasher, to remove any such contaminants that are attached thereto. Alternatively, a user can cleanse the lighting apparatus 10 by wiping it with cloth comprising a solution of dish soap and water. However, the viscoelastic polymer 30 need not be in the form of a substrate 32. Accordingly, the accumulation of such unwanted foreign matter upon a viscoelastic polymer 30 surface area may be effectively removed by simply washing the viscoelastic polymer 30 with common soaps and water solutions, so as to restore its adhesive efficacy. The superior cohesiveness of the viscoelastic polymer 30 allows for washing under conditions which would often cause other materials to disintegrate. Viscoelastic polymers 30 in removable forms thus provide certain useful advantages over viscoelastic polymers 30 in permanent bonded forms (i.e., formed in situ) and vice versa.

As mentioned above, yet another advantage is that the inventive lighting apparatus 10 (particularly its viscoelastic polymer 30 component) exhibits antimicrobial properties. Due to its adhesiveness, the lighting apparatus 10 is prone to adhere microbes thereto. The usefulness of the lighting apparatus 10 becomes particularly applicable within the hygienic field, such as typically arises in the common usage of medical objects 60 and articles 80, such as in medical and dental clinics, hospitals, examining rooms, surgical rooms, etc. The inherent antimicrobial or aseptic properties of the viscoelastic polymer 30 component render it highly effective for a vast array of medical and other hygienic uses. The inventive lighting apparatus 10 can afford a unique ability to attach to a variety objects 60 in order to provide portable or permanent lighting, and can additionally provide a surface for attaching surgical, medical and dental instruments, etc., placed thereupon for convenient access, while also providing a surprising and unexpected effective aseptic and sterile environment. Due to the unique antimicrobial properties of the viscoelastic polymer 30 herein, the capacity to adhesively adhere to an object 60 and then adhere medical and dental instruments thereto in a sterile and aseptic environment represents a significant advance over the current hygienic state of the art. This is particularly significant since conventional adhesive materials lacking antimicrobial attributes in an unprotected environment create an unacceptable increased health hazard, which common and unavoidable hazard is unexpectedly and effectively alleviated by the inventive lighting apparatus 10. The permanency of the thermoset bonding or its removable features and exceptional viscoelastomeric tack or adhesive efficacy, without needing further confinement, plus its antimicrobial properties, affords a significant innovative advance over the current state of the hygienic art. Indeed, in some aspects, because of its antimicrobial properties, a user can even place the lighting apparatus 10 onto one's own skin, such as a forearm, hand, forehead, etc., to provide convenient and directed lighting as desired, while further providing a convenient location to attach various articles 80 (see e.g., FIG. 6J).

Referring now to FIGS. 7A-7C, in still other aspects of the invention, the viscoelastic polymer 30 may be utilized to impart a desired aseptic effect to container combinations 90, such as a tackle box, a toolbox, or a pillbox, for example. The term "container combination 90" as used herein refers to the combination of the lighting apparatus 10 and any supportive structure 60A (e.g., container beds 62, walls 64,66 and/or top walls, etc.) which in the container combination 90 collectively provides a lighted, confining and stowing environment for an adhered article 80 contained by the container combination 90. The container combination 90 may include conventional side walls 64,66, compartments 68 and covers (not shown), but which may become unnecessary for many applications such as with objects 60 in the form of flat trays (e.g., a supportive base structure 60A only, such as a bottom wall or bed 62, for example). The advantage of eliminating the need for conventional confining sidewall structures arises because of the uniquely powerful cohesive and adhesive properties of the viscoelastic polymer 30. In addition to being lighted, the containers 60 are also effectively aseptically protected from microbes through the use of an antimicrobial viscoelastic polymer 30 which constitutes an inherent property of the thermoset viscoelastomeric reaction product from which it is formed. The viscoelastic polymer 30 inherently provides powerful aseptic properties to the container combinations 90 and adhered articles 80. Referring particularly to FIG. 7C, when the interfacing viscoelastic polymer 30 (e.g., as a layer or substrate.) is applied to a container wall 64,66 or bed 62, both the exposed outer surface and the inner container interfacing surface abutting against the viscoelastic polymer 30 will inherently benefit from its unique anti-microbial properties. The viscoelastic polymer 30 and its surrounding environment accordingly do not foster microbial growth, but rather inhibit the development of unhealthy microbial or fungal infestations. Accordingly, the use of the lighting apparatus 10 for surgical and medical uses, as well as other hygienic uses, coupled with the inherent self-cohesive and uniform antimicrobial properties throughout its entire mass opens a new vista for aseptic sterilization which uniquely distinguishes the inventive lighting apparatus 10 from any other conventional lighting apparatus. Accordingly, medical and other hygienic containers 60 for retaining hygienic articles 80 under aseptic conditions, such as those essential to the hygienic use of dental, medical or hygienist cabinet drawers and compartments, bags, kits, boxes including pill boxes, as well as flat surfaced combinations 10 such as other surgical, examining, medical and dental containers, etc. all of which will typically include a supportive base 60A interfacing onto and supporting the antimicrobial viscoelastic polymer 30. Such container combinations 90 exhibit unexpectedly superior and unique antimicrobial advantages over the current technology by maintaining an orderly, aseptic, sterile and systematic environment for a stabilized placement of sterile articles 80, such as medical instruments, devices and medicinal compositions etc. all of which fulfills a long sought medical and hygienic need. As mentioned herein, should dust, debris and other contaminants (including airborne particle contaminants sanitized by the viscoelastic polymer 30) clog the adhesive surfaces (e.g., 30A and/or 30B, etc.) of the viscoelastic polymer 30, the viscoelastic polymer 30 may be readily restored to its original or native condition by a soap and water solution wash without adversely affecting its deep seated antibacterial, antifungal, adhesive and cohesive properties which uniformly permeate throughout the entire compositional makeup of the viscoelastic polymer 30, and those articles 80 coming in contact therewith. As illustrated in FIGS. 7A-7B, similar to medicinal and dental applications, unwanted infections arising from germ infested fishing lures and/or tools may also benefit through the use of the viscoelastic polymer 30. Thus, the viscoelastic polymers 30 are particularly well suited for a host of hygienic uses. Medical, dental and other hygienic combinations 90 such as used by First Responders, ambulance personnel, dentists, dental hygienists, physicians, surgeons, nurses, fishing anglers, hunters, construction workers, mechanics, etc. are accordingly beneficially and uniquely bestowed with a lighted and superior self-sanitizing container combination 90 for adhering articles 80 in a lighted, stabilized, immobilized, sterile and orderly environment. In the case of a tackle box, the lighting apparatus 10 can not only provide antimicrobial affects to the fishing lures and equipment, but can also be useful in re-charging phosphorescent (e.g., glow in the dark) fishing lures, among other benefits.

In addition to the numerous advantages already enumerated herein, the inventive viscoelastic polymer 30 component of the lighting apparatus 10 can also be provided in a non-toxic, environmentally friendly (green) form, virtually free from residual gases or volatizing gases. In addition, the viscoelastic polymer 30 may also impart impact and vibration absorbing attributes which further serves to protect adhered objects 60 and/or articles 80 (as well as other components of the lighting apparatus 10) from impact and vibrational damage. Accordingly, fragile adhered articles 80 such as a photographic lenses, electronic equipment, circuit boards, glass items and other delicate articles, etc. may be protectively adhered and/or restrainingly immobilized against impacting damage and injury.

The present invention may be better understood with reference to the following examples.

EXAMPLES

Example 1

An object 60 in the form of a compartmentalized fishing tackle box tray was provided. An LED strip lighting assembly 45 comprising a plurality of LED lights 20 connected by first electrical connectors 50 and supported by a support structure 40. A second electrical connector 50 extended from the support structure 40 to a battery power source 78, and a switch 70 was located upon the second electrical connector 50 between the support structure 40 and the power source 78. The support structure 40 with the lights 20 and first electrical connector 50 was placed onto the bottom wall (i.e., the floor) support structure 60A of a compartment 68 within the fishing tackle box tray, with the battery power source 78 and switch 70 were positioned outside of the compartment 68. The tackle box assembly was then set aside.

A thermoset viscoelastomeric reaction product adapted to provide an inventive viscoelastic polymer 30 of the present invention having exceptional adhesive, cohesive and releasability efficacy was then prepared by uniformly admixing together a two-part thermosetting reaction media mix comprising Solution A and Solution B, as follows:

Solution A—Solution A was prepared by combining 40 parts of 4,4'-methylenediphenyl diisocyanate (MDI) based glycol prepolymer (ElastoCAST TQZP23, available from BASF Corporation) with 220 parts of plasticizer (comprising 165 parts of epoxidized soy bean oil and 55 parts of dibutal sebacate);

Solution B—Solution B was prepared by combining 175 parts of 2 functional polyether diol (ElastoCAST C-4057 available from BASF Corporation), 170 parts of 3 functional polyether triol (ElastoCAST C-4018 available from BASF Corporation), 2 parts of bismuth-based catalyst (COSCAT 83, available from Vertellus Holdings LLC), 10 parts of UV stabilizer (comprising uv blocker and antioxidant) (Tinuvin b 75, available from BASF Corporation), and 0.5 parts of a pigment.

Solution A and Solution B were then blended together and mixed well. Initial gelling began after about 45 seconds. While still in flowable form (about 1 minute after initial blending), the polymer admixture was poured into the compartment 68 of the fishing tackle box comprising the pre-positioned lighting assembly 45, and was added until a quantity sufficient to completely cover the LED lights in the compartment was reached. After about 15 minutes, the polymer began to set. The polymer was allowed to cure for 24 hours until completely cured, thus forming a viscoelastic polymer 30 component of the present invention. Accordingly, the viscoelastic polymer 30 combined with the lighting assembly 45 provided an inventive lighting apparatus 10 of the present invention. The lighting apparatus 10 was thus adhered to an object 60 in the form of a tackle box tray.

In addition to forming an inventive lighting apparatus 10 of the present invention, a substrate 32 of the viscoelastic polymer 30 was also cast. This was performed by spreading the uncured admixture evenly at a uniform 4 mm thickness upon a polyvinylchloride (PVC) apron and allowing it to cure for 24 hours until fully cured to form an inventive viscoelastic polymer 30 of the present invention. It was observed that the resultant cured substrate 32 was removable from the PVC. The viscoelastic polymer 30 substrate 32 was then cut into test platform 160 size test samples 130 for testing using the testing apparatus 100 depicted in FIG. 8 with the testing procedure being conducted in accordance with the Adhesive & Cohesive Test procedure. The results revealed that the viscoelastic polymer 30 component had an average adhesiveness of at least about 300 g/cm (i.e. about 500 g/cm$^2$), and a Cohesiveness of about 0 (i.e., the viscoelastic polymer 30 component left no residue on the testing cylinder 140 surface 145).

Example 2

A thermoset viscoelastomeric reaction product adapted to provide an inventive viscoelastic polymer 30 component of the present invention having exceptional adhesive, cohesive and releasability efficacy was prepared by uniformly admixing together a two-part thermosetting reaction media mix comprising Solution A and Solution B, as follows: *

Solution A—Solution A was prepared by combining 6.42 percent by weight (6.42 wt %) of 4,4'-methylenediphenyl diisocyanate (MDI) based glycol prepolymer (ELASTOCAST TQZP23), 26.90 wt % of epoxidized soy bean oil, and 8.97 wt % of dibutal sebacate;

Solution B—Solution B was prepared by combining 27.72 wt % of 2 functional polyether diol (ELASTOCAST C-4057), 28.53 wt % of 3 functional polyether triol (ELASTOCAST C-4018), 0.16 wt % of bismuth-based catalyst (COSCAT 83), and 1.30% of UV inhibitor (TINUVIN b 75).

* Note: Percent by weight (wt %) values are based on total weight of Solution A and Solution B.

Iteration 1—Time Sensitivity Effects

The uncured admixture was then tested using the Time Sensitivity Test procedure (described above). More particularly, Solution A and Solution B were blended together, mixed well, and then cast into a substrate 32. This was performed by spreading the uncured admixture evenly at a uniform 4 mm thickness upon a PVC apron and allowing it to cure until fully cured to form an inventive viscoelastic polymer 30 of the present invention. It was observed that the resultant cured substrate 32 was removable from the PVC. The viscoelastic polymer 30 substrate 32 was then cut into test platform 160 size test samples 130 for testing using the testing apparatus 100 depicted in FIG. 8 with the testing procedure being conducted in accordance with the Adhesive & Cohesive Test procedure (set forth above), and additionally performing the optional time dependent properties steps set forth therein.

Test samples 130 prepared from the thermoset viscoelastomeric reaction product formulation of this Example 2 consistently provided stabilized test sample 130 Adhesiveness results requiring a separation force (i.e., adhesion release strength) of more than 300 g/cm$^2$ to separate the tested samples 130 from the contact surface 145 of the testing cylinder 140 using the Adhesive & Cohesive Test procedure. Upon performing the optional time dependent properties steps, the results of the effect of time after a test sample's initial adhesion to the contact surface 145 of the testing cylinder 140 at the designated time intervals is set forth in Table 1 below:

TABLE 1

| Time Sensitive Control | |
|---|---|
| Contact Time (sec) | Removal Force (gt) |
| 5 | 557 g/cm$^2$ |
| 10 | 545 g/cm$^2$ |
| 15 | 534 g/cm$^2$ |
| 30 | 523 g/cm$^2$ |
| 60 | 591 g/cm$^2$ |
| 300 | 545 g/cm$^2$ |
| 600 | 557 g/cm$^2$ |
| 900 | 580 g/cm$^2$ |
| 6 weeks | 625 g/cm$^2$ |

It can be seen that the test sample 130 of this Example 2 reached more than 90% of its maximum adhesive release strength within one (1) minute after its initial contact with the contact surface 145 of the testing cylinder 140. It has been consistently observed that other test samples of a 300 g/cm$^2$ plus adhesion release strength will typically also reach more than 90% of their maximum adhesive release strength within one (1) minute after each sample's initial contact with the contact surface 145 of the testing cylinder 140.

Unlike many adhesives which undesirably undergo substantial increases in adhesiveness over prolonged usage intervals, rendering them generally unfit for use as a releasable adhesive, the viscoelastic polymer 30 of this Example 2 exhibited excellent stability over extended time periods. Indeed, even after a 6-week test period, the Example 2 viscoelastic polymer 30 exhibited less than a 10% change in adhesion release strength relative to the adhesion release strength tests taken 60 seconds after initial contact with the contact surface 145 of the testing cylinder 140 of the apparatus 100 illustrated in FIG. 8. As evident from the aforementioned, the tested viscoelastic polymer 30 substrate 32 (as well as in the other viscoelastic polymers disclosed herein) characteristically exhibited excellent adhesion and cohesion stability rendering it well suited for use as a viscoelastic polymer 30 component for the inventive lighting apparatus 10 herein.

Comparatively, it was observed that the dibutyl sebacate plasticizer containing reaction media of this Example 2 substantially reduced the initial uncured viscosity, whereas the 45.84 wt % epoxidized soybean oil formulation of Example 3 (discussed below) was more viscus. The more fluid thermosetting reaction media rendered the dibutyl sebacate containing reaction media better suited for many fabrication techniques commonly used to convert the reaction media and the resultant viscoelastic polymer 30 component of the lighting apparatus 10 into a fabricated commercial product. Uniform dispersal of the plasticizer within the unique thermoset polymerizate structure places constraints upon the use of diluting solvent based systems while the application of higher temperatures prematurely hasten curing. Similarly, the polyether and polyester diols and triols of an excessive molecular weight are typically a solid or are waxy, which limits their effective prefabrication usage.

Iteration 2—Effect of Pressure

In order to test the effect of an initial application of pressure and essentially a nominal pressure application by the contact surface 145 of the testing cylinder 140 of the apparatus 100 illustrated in FIG. 8 upon test samples 130, the optional pressure dependent properties of the Adhesive & Cohesive Test were performed. More particularly, an applied force of 110 grams of weight and essentially a nominal application force of comparative tests were conducted in order to ascertain the effect pressure had upon adhesion. The test samples 130 were secured to the movable test platform 160 after which a uniform pressure of 110 $g_f$ was applied to the testing cylinder 140 to test the pressurized test samples 130. Similar comparative tests were conducted using the same test apparatus 100 and procedure, except only a nominal pressure (relying solely upon the free hanging cylinder 140 weight of 20 grams) was applied to the test samples 130. The testing apparatus 100 with the test samples 130 secured to the test platform 160 were then subjected to a constant speed (2.7 cm/sec) withdrawing force using the testing apparatus 100 shown in FIG. 8. The counteracting force needed to break or separate the adhesive bond (i.e., adhesiveness) between each of the test samples 130 and the cylinder 140 was then determined.

It was observed that the application of the 110 grams of pressure by the testing cylinder 140 upon the tested samples 130 of the viscoelastic polymer 30 initially resulted in a quicker and higher adhesion release strength (adhesiveness) (e.g., within 15 seconds) than the adhesive release strength of the nominal applied pressure tests, which took a substantially longer period of time to obtain their maximum adhesive release strength. However, the nominal applied pressure to cylinder 140 tests ultimately achieved an adhesion release strength comparable to the 110 grams applied pressure sample tests. Obviously, the adhesive forces in the nominal pressure applied test caused the viscoelastic polymer 30 test sample 130 to internally undergo further adhesive attractive forces without any other extrinsic factor being attributable to its increase in adhesiveness. This subsequent increase in adhesiveness for the nominal pressurized test application tends to indicate that an internal polarity change within the tested reaction product after initial contact with the contact surface 145 of the testing cylinder 140 may have occurred, which phenomenon may be due to electron migration within the thermoset viscoelastomeric mass after the initial contact of the cylinder 140 to the sample 130. This delayed adhesive attraction may also possibly arise by reason that the sample 130 draws the cylinder 140 deeper into the sample 130 creating a greater adhesiveness, or some other unknown phenomenon may exist.

Iteration 3—Thermosetting Bonding Characteristics

An uncured admixture of this example was then spread evenly at a uniform 3 mm thickness upon a polyvinylchloride film and allowed to cure to the desired viscoelastic polymer 30, which after separation from the PVC film, was then cut into insert test panel patch sizes for testing using the testing apparatus 100 depicted in FIG. 8.

The resultant cured viscoelastic polymer 30 coating exhibited an increased bonding strength between the cured viscoelastic polymer 30 and the PVC film. The PVC film could nonetheless be manually separated from the viscoelastic polymer 30 coating. By peeling the cured viscoelastic polymer 30 from the PVC film, the entire PVC film could accordingly be removed from the viscoelastic polymer 30 coating. By covering both surfaces of the viscoelastic polymer 30 with protective plastic films (e.g., PVC films) or other plastics to sandwich the reaction product therebetween, a ready-to-use and protected viscoelastic polymer 30 component was formed. Thus, a viscoelastic polymer 30 requiring only a stripping of the overlaying protective films (useful from formation of the viscoelastic polymer 30 to its ultimate attachment with a light 20 to form a lighting apparatus 10) may be effectively provided for consumer use. The reduced plasticizer level to less than 40% by weight of the reaction media weight tends to enhance the bonding attributes of the cured viscoelastic polymer 30 coating. The outwardly and unbound surface of the viscoelastic polymer 30 test sample however possessed excellent adhering attributes. This example illustrates the versatility in preparing viscoelastic polymers 30 which can releasably or permanently bond to a diverse range of objects 60 including those which do not normally bond to urethane thermosets.

Iteration 4—Permanent Coating Bonding

A freshly mixed, uncured reaction media of this Example 2 was used to coat a high density polypropylene supportive base 60A (see e.g., FIGS. 7A-7C). Three (3) mm of coating was applied to a preflamed bed support structure 60A of an object 60 in the form of a polypropylene fishing tackle box. The mixed reaction media was allowed to cure and bond to the support structure 60A. The resulting cured viscoelastic polymer 30 first surface 30A had virtually all of the characteristics of a chemically or permanently bonded coating which could not be effectively removed from the polypropylene container support structure 60A. However, the opposite unbound second surface 30B of the viscoelastic polymer 30 retained its excellent stabilized adhesiveness rendering it particularly useful as a viscoelastic polymer 30 component for a lighting apparatus 10 that can be permanently adhered to an object 60. This reaction media is especially useful to permanently bond a lighting apparatus 10 to a host of common thermoplastic objects 60.

Iteration 5—Plasticizer Variations

Using the basic formulation of the viscoelastic polymer 30 of this Example 2, the weight amount of the plasticizer was held constant, but the weight ratio of epoxidized soybean oil (ESO) to dibutyl sebecate (DBS) was changed to 1:0 (i.e., all ESO), 1:1 (i.e., 50% ESO and 50% DBS) and 1:3 (i.e., 25% ESO and 75% DBS). (The 1-ESO to 0-DBS, the 1-ESO to 1-DBS and the 1-ESO to 3-DBS weight ratios.) Upon adhesive release strength (i.e., adhesiveness) testing, it was observed that the samples provided values of 568 $g_f/cm^2$, 420 $g_f/cm^2$ and 341 $g_f/cm^2$, respectively. It may accordingly be concluded that by altering the ratios and type of plasticizer, the adhesive character, the adhesive use and the fabricating properties may be preselected to fit any desired particular end use and purpose.

Example 3

A thermoset viscoelastomeric reaction product adapted to provide an inventive viscoelastic polymer 30 of the present invention containing 45.84 wt % epoxidized soybean oil plasticizer was prepared by uniformly admixing together a two part thermosetting reaction media mix comprising Solution A and Solution B, as follows:*

Solution A—Solution A was prepared by combining 5.56 wt % of 4,4'-methylenediphenyl diisocyanate (MDI) based glycol prepolymer (ELASTOCAST TQZP23), and 44.44 wt % of epoxidized soy bean oil;

Solution B—Solution B was prepared by combining 17.52 wt % of 2 functional polyether diol (ELASTOCAST C-4057), 28.00 wt % of 3 functional polyether triol (ELASTOCAST C-4018), 1.40 wt % of epoxidized soy bean oil, 0.52 wt % of bismuth-based catalyst (COSCAT 83), and 1.12% of UV inhibitor (TINUVIN b 75), and 1.44 wt % of a dye.

* Note: Percent by weight (wt %) values are based on total weight of Solution A and Solution B.

Iteration 1—Thermosetting Bonding Characteristics

Solution A and Solution B were blended together, mixed well, and then cast into a substrate 32. This was performed by spreading the uncured admixture evenly at a 3 mm thick coating upon a 0.3 mm PVC film, and then covered with a 0.3 mm high-density polypropylene film, and allowed to cure. It was readily apparent that the cured viscoelastic polymer 30 coatings were more loosely bound to the PVC film since the film was more easily peelable from the viscoelastic polymer 30 coatings than was the coating of Example 2. The adhesive release strength, when cured in situ with the films, was somewhat greater than the maximum adhesive release strength of 490 $g_f/cm^2$ recorded by the test samples 130 of the viscoelastic polymer 30.

The reduced plasticizer content, along with a balanced diol to triol ratio, appears to significantly contribute to the bonding strength of the cured viscoelastic polymer 30 to a host of objects 60 when cured in situ. For certain applications, a bonded but readily peelable in situ cured reaction media coating and protective film covering both surfaces of the cured viscoelastic polymer 30 may be commercially desirable. This provides a viscoelastic polymer 30 which may be transported in the channels of commerce and paired with a lighting assembly 45 to form a lighting apparatus 10 of the present invention, which can then be subsequently adhered to an object 60 by the ultimate consumer.

The in situ cured viscoelastic polymer 30 protected on both surfaces by the protective films may be most suitably formulated with about a 40-percent by weight (40 wt %) to less than 50-percent by weight (50 wt %) plasticizer. At plasticizer levels below the 40-percent (40 wt %) level, the peelablility factor becomes more difficult.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. A lighting apparatus comprising at least one light and an adhesive and cohesive thermoset viscoelastic polymer adhesively adhered to the at least one light.

2. The lighting apparatus of claim 1 wherein the viscoelastic polymer is prepared by thermosetting a reaction media comprising a substantially uniform admixture of:
   a) an isocyanate prepolymer,
   b) about 35-percent to about 55-percent by weight of polyols, and
   c) an effective amount of plasticizer containing less than about 50-percent by weight of an epoxidized triglyceride plasticizer,
   wherein the polyols comprise straight chain linking diols and cross-linking triols, each having repetitive oxygen-containing functional groups at a weight ratio of diols to triols ranging from about 7:13 to about 13:7.

3. The lighting apparatus of claim 2 wherein the effective amount of plasticizer is sufficient to provide an adhesiveness of the resultant viscoelastic polymer of at least about 300 $g_f/cm^2$ as measured by the Adhesiveness & Cohesiveness Test.

4. The lighting apparatus of claim 1 wherein the viscoelastic polymer is adhered to the at least one light either via adhesive bonding of the viscoelastic polymer to the at least one light, or via chemical bonding by thermosetting in situ onto the at least one light a reaction media which forms the viscoelastic polymer.

5. The lighting apparatus of claim 1 wherein the viscoelastic polymer compositionally possesses sufficient adhesiveness and cohesiveness to adhere the lighting apparatus to an object at a stabilized position and to release the lighting apparatus by an applied force sufficient to overcome an adhesive attraction of the viscoelastic polymer to the object.

6. The lighting apparatus of claim 1, wherein the at least one light is a low power light, a low temperature light, or combination thereof.

7. The lighting apparatus of claim 1, wherein the viscoelastic polymer at least partially encapsulates the at least one light.

8. The lighting apparatus of claim 1 further comprising an electrical connector.

9. The lighting apparatus of claim 1 further comprising a switch.

10. The lighting apparatus of claim 1 further comprising a support structure.

11. The lighting apparatus of claim 10 wherein the at least one light and the support structure form a lighting assembly.

12. The lighting apparatus of claim 1, wherein the viscoelastic polymer exhibits an adhesiveness of at least about 300 $g/cm^2$ as measured by the Adhesiveness & Cohesiveness Test.

13. The lighting apparatus of claim 12, wherein the viscoelastic polymer exhibits an adhesiveness of at least about 500 $g/cm^2$ as measured by the Adhesiveness & Cohesiveness Test.

14. The lighting apparatus of claim 12, wherein the viscoelastic polymer exhibits an adhesiveness of between about 300 $g/cm^2$ and 2200 $g/cm^2$ as measured by the Adhesiveness & Cohesiveness Test.

15. The lighting apparatus of claim 14, wherein the viscoelastic polymer exhibits an adhesiveness of between about 500 $g/cm^2$ and 1200 $g/cm^2$ as measured by the Adhesiveness & Cohesiveness Test without evidencing any substantial change in the adhesiveness after at least about four (4) weeks.

16. The lighting apparatus of claim 1, wherein the viscoelastic polymer exhibits antimicrobial properties.

17. The lighting apparatus of claim 1 wherein the viscoelastic polymer comprises a thermoset reaction product of a thermosetting reaction media comprising:
   a) a cross-linked thermoset structure obtained by reacting:
      1) about 4-percent to about 7-percent by weight of a diisocyanate prepolymer;
      2) about 10-percent to about 35-percent by weight of a straight chain producing polyether diol; and
      3) about 25-percent to about 35-percent by weight of a polyether triol;
      wherein the weight ratio of the polyether diol to the polyether triol ranges from about 7:13 to about 13:7; and
   b) from about 20-percent to about 55-percent by weight of a plasticizer uniformly and cohesively dispersed throughout the reaction product, wherein the plasticizer comprises:
      1) 0-percent to less than about 50-percent by weight of an epoxidized triglyceride and
      2) 0-percent to about 40-percent by weight of an ester plasticizer.

18. The lighting apparatus of claim 1 wherein the viscoelastic polymer comprises a cohesive and adhesive thermoset viscoelastomeric reaction product formed from a thermosetting reaction media comprising:
   a) about 10-percent to about 35-percent by weight of a polyether diol;
   b) about 25-percent to about 35-percent by weight of a polyether triol;
   c) about 4-percent to about 7-percent by weight of an diisocyanate prepolymer; and
   d) about 20-percent to less than about 50-percent by weight of an epoxidized triglyceride oil;
   wherein the weight ratio of the polyether diol to polyether triol ranges from about 7:13 to about 13:7; and
   wherein the thermosetting reaction media has been cured by a catalytic amount of a curing catalyst.

19. The lighting apparatus of claim 18 wherein the epoxidized triglyceride oil comprises an epoxidized soybean oil in an amount ranging from about 42-percent to about 48-percent by weight of the total reaction media weight.

20. The lighting apparatus of claim 18 wherein the weight ratio of polyether diol to polyether triol ranges from about 2:3 to about 3:2.

21. The lighting apparatus of claim 18 wherein the polyether diol and polyether triol each have a molecular weight ranging from about 1000 to about 8000 consisting essentially of either an ethylene or a propylene ether linkage.

22. The lighting apparatus of claim 18 wherein the polyether diol and the polyether triol comprise a sequenced oxyalkylene polyols grouping selected from a polyoxyethylene and a polyoxypropylene grouping, wherein the polyether diol and the polyether triol each have a molecular weight ranging from about 3000 to about 6000 and the epoxidized triglyceride oil consists essentially of an epoxidized soybean oil.

23. The lighting apparatus of claim 18 wherein the epoxidized triglyceride oil is epoxidized vegetable oil ranging from about 25-percent to about 45-percent by weight, and wherein the thermosetting reaction media further comprises from about 10-percent to about 40-percent by weight of a polyalkylene ester polyester.

24. The lighting apparatus of claim 18 wherein the substrate is chemically bonded to a surface area of the at least one light by thermosetting the reaction media in situ upon the surface area.

25. The lighting apparatus of claim 1, wherein the viscoelastic polymer comprises:
   a) about 3-percent to about 8-percent by weight of an isocyanate prepolymer;
   b) about 10-percent to about 35-percent by weight of a straight chain producing polyoxyalkylene diol;
   c) about 10-percent to about 40-percent by weight of a cross-linking polyoxyalkylene triol;
   d) 0-percent to less than about 50-percent by weight of an epoxidized triglyceride; and
   e) greater than about 5-percent by weight of an ester plasticizer.

26. The lighting apparatus of claim 25, wherein cross-links caused by polymerization of the cross-linking polyoxyalkylene triols are separated by intervening straight chain bridging polymerizates provided by the straight chain producing polyoxyalkylene diol, and wherein the weight ratio of polyoxyalkylene diol to polyoxyalkylene triol ranges from about 3:2 to about 2:3.

27. The lighting apparatus of claim 25, wherein the polyoxyalkylene diol and the polyoxyalkylene triol each comprise an alkylene grouping of either an ethylene group or a propylene group.

28. The lighting apparatus of claim 25, wherein the molecular weight of the polyoxyalkylene diol and the polyoxyalkylene triol range from about 3000 to about 6000.

29. The lighting apparatus of claim 1 wherein the viscoelastic polymer comprises:
   a) about 3-percent to about 10-percent by weight of an isocyanate prepolymer;
   b) about 10-percent to about 35-percent by weight of a polyether diol having a molecular weight of at least about 1000;
   c) about 10-percent to about 40-percent by weight of a polyether triol having a molecular weight of at least about 1000; and
   d) about 20-percent to less than about 50-percent by weight of a plasticizer;
   wherein the weight ratio of polyether diol to polyether triol ranges from about 7:13 to about 13:7.

30. The lighting apparatus of claim 1 wherein the viscoelastic polymer comprises:

a) about 30 parts to about 50 parts by weight of an isocyanate prepolymer;
b) about 150 parts to about 200 parts by weight of a polyether diol;
c) about 150 parts to about 200 parts by weight of a polyether triol;
d) about 200 parts to about 240 parts by weight of plasticizer;
e) about 1 part to about 3 parts by weight of a bismuth-based catalyst; and
f) 0 parts to about 20 parts by weight of a UV stabilizer;
wherein the diol to triol weight ratio ranges from about 7:13 to about 13:7; and
wherein the plasticizer comprises from about 150 parts to about 180 parts by plasticizer weight of epoxidized soybean oil and about 40 parts to about 70 parts by plasticizer weight of dibutal sebacate.

31. The lighting apparatus of claim 30 wherein the viscoelastic polymer further comprises from 0 parts to about 2 parts by weight of a pigment.

32. The lighting apparatus of claim 30 wherein the isocyanate prepolymer is 4,4-methylenediphenyl diisocyanate-based prepolymer.

33. The lighting apparatus of claim 1 wherein the viscoelastic polymer has a thickness ranging from about 1.5 mm to about 25 cm.

34. A method for making a lighting apparatus having a sufficient stable adhesiveness and cohesiveness to retain to, and to release from, an object, comprising:
a) providing a light
b) providing a power source;
c) providing a switch electrically connected to the light and the power source;
d) providing an uncured thermoset viscoelastomeric reaction product of a thermosetting reaction media comprising:
1) about 10-percent to about 35-percent by weight of a diol;
2) about 25-percent to about 35-percent by weight of a triol;
3) about 4-percent to about 7-percent by weight of an isocyanate prepolymer; and
4) about 42-percent to less than about 50-percent by weight of an epoxidized vegetable oil;
e) coating at least a portion of the light with the uncured thermoset viscoelastomeric reaction product;
f) curing the thermoset viscoelastomeric reaction product in situ to form a lighting apparatus comprising a viscoelastic polymer;
wherein the viscoelastic polymer is bonded to the light to form the lighting apparatus.

35. The method of claim 34, wherein the thermosetting reaction media further comprises an effective amount of a thermosetting catalyst for curing into the viscoelastic polymer.

36. The method of claim 34 further comprising placing the lighting apparatus in contact with an object, such that the viscoelastic polymer is adhesively engaged and releasably secured to the object.

37. The method of claim 34 further comprising placing an article in contact with the lighting apparatus.

38. A method of forming a lighting apparatus-container combination comprising:
a) providing a lighting assembly comprising a light, an electrical connector, and a switch;
b) providing a container;
c) positioning the lighting assembly in contact with a first location within the container;
d) providing a thermosetting reaction media by combining a first solution comprising about 1-percent to about 10-percent by weight of the reaction media of an isocyanate prepolymer and about 20-percent to less than about 50-percent by weight of the reaction media of a plasticizer, with a second solution comprising about 10-percent to about 40-percent by weight of the reaction media of a diol and about 10-percent to about 40-percent by weight of the reaction media of a triol;
e) mixing the first solution with the second solution to form an uncured viscoelastic polymer;
f) coating at least a portion of the of the lighting assembly and a least a portion of the first location of the container with at least a portion of the uncured viscoelastic polymer;
g) allowing the uncured viscoelastic polymer to cure to form a lighting apparatus adhered to the first location of the container, to form a lighting apparatus-container combination.

39. The method of claim 38 wherein the ester plasticizer is an ester of a sebecate plasticizer.

40. The method of claim 38 wherein the second solution further comprises about 0.5-percent to about 5.0-percent by weight of the reaction media of a UV stabilizer.

41. The method of claim 38 wherein the second solution further comprises less than about 1.0-percent by weight of the reaction media of a pigment.

42. The method of claim 38 wherein the second solution has a polydiol to polytriol weight ratio of about 3:2 to about 2:3.

43. The method of claim 38 wherein the polydiol and the polytriol are polyethers.

44. The method of claim 38 wherein the polydiol and polytriol each comprise an alkylene grouping selected from the group consisting of an ethylene group or a propylene group.

45. The method of claim 38 wherein the switch is substantially free of viscoelastic polymer.

46. The method of claim 38 wherein allowing the uncured viscoelastic polymer to cure forms a viscoelastic polymer component of the lighting apparatus having a thickness of at least about one (1) millimeter.

47. The method of claim 38 wherein the container is selected from a tackle box, a toolbox, a pillbox, an ammunition box or a cosmetic container.

* * * * *